(12) United States Patent
Rudra-Ganguly et al.

(10) Patent No.: US 10,751,422 B2
(45) Date of Patent: *Aug. 25, 2020

(54) ANTIBODY DRUG CONJUGATES (ADC) THAT BIND TO FLT3 PROTEINS

(71) Applicant: AGENSYS, INC., Santa Monica, CA (US)

(72) Inventors: Nandini Rudra-Ganguly, Santa Monica, CA (US); Christine Lowe, Northridge, CA (US); Faisal Hayat Malik, Cerritos, CA (US); Sung Ju Moon, Santa Monica, CA (US); Josh Snyder, Santa Monica, CA (US); Hector Avina, Los Angeles, CA (US); Cyrus Virata, Mission Hills, CA (US); Linnette Capo, Sherman Oaks, CA (US); Gao Liu, Culver City, CA (US)

(73) Assignee: AGENSYS, INC., Santa Monica, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/556,587

(22) PCT Filed: Mar. 9, 2016

(86) PCT No.: PCT/US2016/021592
§ 371 (c)(1),
(2) Date: Sep. 7, 2017

(87) PCT Pub. No.: WO2016/145099
PCT Pub. Date: Sep. 15, 2016

(65) Prior Publication Data
US 2018/0037657 A1    Feb. 8, 2018

Related U.S. Application Data

(60) Provisional application No. 62/130,476, filed on Mar. 9, 2015.

(51) Int. Cl.
*A61K 45/06*       (2006.01)
*A61K 47/68*       (2017.01)
*C07K 16/28*       (2006.01)
*C07K 16/30*       (2006.01)
*A61K 39/00*       (2006.01)

(52) U.S. Cl.
CPC .......... *A61K 47/6803* (2017.08); *A61K 45/06* (2013.01); *A61K 47/6811* (2017.08); *A61K 47/6849* (2017.08); *C07K 16/2863* (2013.01); *C07K 16/30* (2013.01); *A61K 2039/505* (2013.01); *C07K 2317/21* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/732* (2013.01)

(58) Field of Classification Search
CPC ............................ A61K 47/6803; A61K 45/06
USPC ........................................................ 424/179.1
See application file for complete search history.

(56) References Cited

U.S. PATENT DOCUMENTS

| | | |
|---|---|---|
| 7,534,867 B1 | 5/2009 | Hannum et al. |
| 2002/0107365 A1 | 8/2002 | Lyman et al. |
| 2003/0219827 A1 | 11/2003 | Comb et al. |
| 2004/0033491 A1 | 2/2004 | Alsobrook, II et al. |
| 2006/0018910 A1 | 1/2006 | Gualberto et al. |
| 2008/0050774 A1 | 2/2008 | Berka et al. |
| 2008/0124345 A1 | 5/2008 | Rothe et al. |
| 2009/0053226 A1 | 2/2009 | Crowley et al. |
| 2011/0177070 A1 | 7/2011 | Lofquist et al. |
| 2012/0328612 A1 | 12/2012 | Grosse-Hovest et al. |
| 2013/0095097 A1 | 4/2013 | Blankenship et al. |
| 2014/0213459 A1 | 7/2014 | Beckmann |
| 2016/0272716 A1 | 9/2016 | Lowe et al. |

FOREIGN PATENT DOCUMENTS

| | | |
|---|---|---|
| RU | 2436796 C2 | 12/2011 |
| TW | 201446806 A | 12/2014 |
| WO | WO 2001089577 A2 | 11/2001 |
| WO | WO 2005117986 A2 | 12/2005 |
| WO | WO 2005117986 A3 | 12/2005 |
| WO | WO 2006008639 A1 | 1/2006 |
| WO | WO 2006060419 A2 | 6/2006 |
| WO | WO 2007140371 A2 | 12/2007 |
| WO | WO 2007140371 A3 | 12/2007 |
| WO | WO 2009155015 A1 | 12/2009 |
| WO | WO 2013093809 A1 | 7/2013 |
| WO | WO 2014150937 A1 | 9/2014 |

OTHER PUBLICATIONS

H2ZZ60, UniProtKB/TrEMBL Accession No. H2ZZ60, Nov. 26, 2014 (online]. [Retrieved on May 19, 2016]. Retrieved from the internet <URL:http://www.uniprot.org/uniprot/H2ZZ60.txt?version=23>, 2 pages.

(Continued)

*Primary Examiner* — Sean E Aeder
(74) *Attorney, Agent, or Firm* — Jones Day

(57) ABSTRACT

Antibody drug conjugates (ADC's) that bind to FLT3 protein and variants thereof are described herein. FLT3 exhibits a distinct and limited expression pattern in normal adult tissue(s), and is aberrantly expressed in the cancers listed in Table I. Consequently, the ADC's of the invention provide a therapeutic composition for the treatment of cancer.

13 Claims, 30 Drawing Sheets
Specification includes a Sequence Listing.

(56) References Cited

OTHER PUBLICATIONS

K9EF16, UniProtKB/TrEMBL Accession No. K9EF16, Oct. 1, 2014 [online]. [Retrieved on May 19, 2016]. Retrieved from the internet <URL:http://www.uniprot.org/uniprot/K9EF16.txt?version=6>, 2 pages.
S4RPT5, UniProtKB/TrEMBL Accession No. S4RPT5, Nov. 26, 2014 (online]. [Retrieved on May 19, 2016). Retrieved from the internet <URL:http://www.uniprot.org/uniprot/S4RPT5.txt?version=10>, 2 pages.
W7STE1, UniprotKB/TrEMBL Accession No. W7STE1, Oct. 29, 2014 [online]. [Retrieved on May 19, 2016]. Retrieved from the internet <URL:http://www.uniprot.org/uniprot/W7STE1.txt?version=4>, 2 pages.
Brand et al., 2006, "Prospect for anti-HER2 receptor therapy in breast cancer," Anticancer Res., 26(1B):463-470.
Casset et al., 2003, "A peptide mimetic of an anti-CD4 monoclonal antibody by rational design," Biochem Biophys Res Commun., 307(1):198-205.
De Pascalis et al., 2002, "Grafting of "abbreviated" complementarity-determining regions containing specificity-determining residues essential for ligand contact to engineer a less immunogenic humanized monoclonal antibody," J Immunol., 169(6):3076-3084.
International Search Report and Written Opinion of PCT/US2016/021592 (Pub. No. WO 2016145099) dated Jun. 21, 2016 (10 pages).
Paul, 1993, "Fundamental Immunology, 3rd Edition," pp. 292-295.
Piloto et al., 2006, "IMC-EB10, an anti-FLT3 monoclonal antibody, prolongs survival and reduces nonobese diabetic/severe combined immunodeficient engraftment of some acute lymphoblastic leukemia cell lines and primary leukemic samples," Cancer Res., 66(9):4843-4851.
Rudikoff et al., 1982, "Single amino acid substitution altering antigen-binding specificity," Proc Natl Acad Sci USA, 79(6):1979-1983.
Strome et al., 2007, "A mechanistic perspective of monoclonal antibodies in cancer therapy beyond target-related effects," Oncologist, 12(9):1084-1095.
Williams et al., 2005, Cell-based selection of internalizing fully human antagonistic antibodies directed against FLT3 for suppression of leukemia cell growth, Leukemia, 19(8):1432-1438.

Figure 1 The cDNA (SEQ ID NO: 1) and amino acid sequence (SEQ ID NO: 2) of human FLT3. The start methionine is underlined. The open reading frame extends from nucleic acid 67-3048 including the stop codon.

```
   1 GTTTTACACGAGGCGGCATCGCAGGGCTGGGCCGGCGCGGCCTGGGGACCCCGGGCTCCG
                   M  P  A  L  A  R  D  G  G  Q  L  P  L  L  V  V  F  S
  61 GAGGCCATGCCGGCGTTGGCGCGCGACGGCGGCCAGCTGCCGCTGCTCGTTGTTTTTCT
      A  M  I  F  G  T  I  T  N  Q  D  L  P  V  I  K  C  V  L  I
 121 GCAATGATATTTGGGACTATTACAAATCAAGATCTGCCTGTGATCAAGTGTGTTTTAATC
      N  H  K  N  N  D  S  S  V  G  K  S  S  Y  P  M  V  S  E
 181 AATCATAAGAACAATGATTCATCAGTGGGGAAGTCATCATATATCCCATGGTATCAGAA
      S  P  E  D  L  G  C  A  L  R  P  Q  S  S  G  T  V  Y  E  A
 241 TCCCCGGAAGACCTCGGGTGTGCGTTGAGACCCCAGAGCTCAGGGACAGTGTACGAAGCT
      A  A  V  E  V  D  V  S  A  S  I  T  L  Q  V  L  V  D  A  P
 301 GCCGCTGTGGAAGTGGATGTATCTGCTTCCATCACACTGCAAGTGCTGGTCGATGCCCCA
      G  N  I  S  C  L  W  V  F  K  H  S  S  L  N  C  Q  P  H  F
 361 GGGAACATTTCCTGTCTCTGGGTCTTTAAGCACAGCTCCCTGAATTGCCAGCCACATTTT
      D  L  Q  N  R  G  V  V  S  M  V  I  L  K  M  T  E  T  Q  A
 421 GATTTACAAAACAGAGGAGTTGTTTCCATGGTCATTTTGAAAATGACAGAAACCCAAGCT
      G  E  Y  L  L  F  I  Q  S  E  A  T  N  Y  T  I  L  F  T  V
 481 GGAGAATACCTACTTTTTATTCAGAGTGAAGCTACCAATTACACAATATTGTTTACAGTG
      S  I  R  N  T  L  L  Y  T  L  R  R  P  Y  F  R  K  M  E  N
 541 AGTATAAGAAATACCCTGCTTTACACATTAAGAAGACCTTACTTTAGAAAAATGGAAAAC
      Q  D  A  L  V  C  I  S  E  S  V  P  E  P  I  V  E  W  V  L
 601 CAGGACGCCCTGGTCTGCATATCTGAGAGCGTTCCAGAGCCGATCGTGGAATGGGTGCTT
      C  D  S  Q  G  E  S  C  K  E  E  S  P  A  V  V  K  K  E
 661 TGCGATTCACAGGGGGAAAGCTGTAAAGAAGAAAGTCCAGCTGTTGTTAAAAAGGAGGAA
      K  V  L  H  E  L  F  G  M  D  I  R  C  C  A  R  N  E  L  G
 721 AAAGTGCTTCATGAATTATTTGGGATGGACATAAGGTGCTGTGCCAGAAATGAACTGGGC
      R  E  C  T  R  L  F  T  I  D  L  N  Q  T  P  Q  T  T  L  P
 781 AGGGAATGCACCAGGCTGTTCACAATAGATCTAAATCAAACTCCTCAGACCACATTGCCA
      Q  L  F  L  K  V  G  E  P  L  W  I  R  C  K  A  V  H  V  N
 841 CAATTATTTCTTAAAGTAGGGGAACCCTTATGGATAAGGTGCAAAGCTGTTCATGTGAAC
      H  G  F  G  L  T  W  E  L  E  N  K  A  L  E  E  G  N  Y  F
 901 CATGGATTCGGGCTCACCTGGGAATTAGAAAACAAAGCACTCGAGGAGGGCAACTACTTT
      E  M  S  T  Y  S  T  N  R  T  M  I  R  I  L  F  A  F  V  S
 961 GAGATGAGTACCTATTCAACAAACAGAACTATGATACGGATTCTGTTTGCTTTTGTATCA
      S  V  A  R  N  D  T  G  Y  Y  T  C  S  S  S  K  H  P  S  Q
1021 TCAGTGGCAAGAAACGACACCGGATACTACACTTGTTCCTCTTCAAAGCATCCCAGTCAA
      S  A  L  V  T  I  V  E  K  G  F  I  N  A  T  N  S  S  E  D
1081 TCAGCTTTGGTTACCATCGTAGAAAAGGGATTTATAAATGCTACCAATTCAAGTGAAGAT
      Y  E  I  D  Q  Y  E  E  F  C  F  S  V  R  F  K  A  Y  P  Q
1141 TATGAAATTGACCAATATGAAGAGTTTTGTTTTTCTGTCAGGTTTAAAGCCTACCCACAA
      I  R  C  T  W  T  F  S  R  K  S  F  P  C  E  Q  K  G  L  D
1201 ATCAGATGTACGTGGACCTTCTCTCGAAAATCATTTCCTTGTGAGCAAAAGGGTCTTGAT
      N  G  Y  S  I  S  K  F  C  N  H  K  H  Q  P  G  E  Y  I  F
1261 AACGGATACAGCATATCCAAGTTTTGCAATCATAAGCACCAGCCAGGAGAATATATATTC
```

Figure 1 (Continued)

```
            H  A  E  N  D  D  A  Q  F  T  K  M  F  T  L  N  I  R  R  K
1321  CATGCAGAAAATGATGATGCCCAATTTACCAAAATGTTCACGCTGAATATAAGAAGGAAA
            P  Q  V  L  A  E  A  S  A  S  Q  A  S  C  F  S  D  G  Y  P
1381  CCTCAAGTGCTCGCAGAAGCATCGGCAAGTCAGGCGTCCTGTTTCTCGGATGGATACCCA
            L  P  S  W  T  W  K  K  C  S  D  K  S  P  N  C  T  E  E  I
1441  TTACCATCTTGGACCTGGAAGAAGTGTTCAGACAAGTCTCCCAACTGCACAGAAGAGATC
            T  E  G  V  W  N  R  K  A  N  R  K  V  F  G  Q  W  V  S  S
1501  ACAGAAGGAGTCTGGAATAGAAAGGCTAACAGAAAAGTGTTTGGACAGTGGGTGTCGAGC
            S  T  L  N  M  S  E  A  I  K  G  F  L  V  K  C  C  A  Y  N
1561  AGTACTCTAAACATGAGTGAAGCCATAAAAGGGTTCCTGGTCAAGTGCTGTGCATACAAT
            S  L  G  T  S  C  E  T  I  L  L  N  S  P  G  P  F  P  F  I
1621  TCCCTTGGCACATCTTGTGAGACGATCCTTTTAAACTCTCCAGGCCCCTTCCCTTTCATC
            Q  D  N  I  S  F  Y  A  T  I  G  V  C  L  L  F  I  V  V  L
1681  CAAGACAACATCTCATTCTATGCAACAATTGGTGTTTGTCTCCTCTTCATTGTCGTTTTA
            T  L  L  I  C  H  K  Y  K  K  Q  F  R  Y  E  S  Q  L  Q  M
1741  ACCCTGCTAATTTGTCACAAGTACAAAAAGCAATTTAGGTATGAAAGCCAGCTACAGATG
            V  Q  V  T  G  S  S  D  N  E  Y  F  Y  V  D  F  R  E  Y  E
1801  GTACAGGTGACCGGCTCCTCAGATAATGAGTACTTCTACGTTGATTTCAGAGAATATGAA
            Y  D  L  K  W  E  F  P  R  E  N  L  E  F  G  K  V  L  G  S
1861  TATGATCTCAAATGGGAGTTTCCAAGAGAAAATTTAGAGTTTGGGAAGGTACTAGGATCA
            G  A  F  G  K  V  M  N  A  T  A  Y  G  I  S  K  T  G  V  S
1921  GGTGCTTTTGGAAAAGTGATGAACGCAACAGCTTATGGAATTAGCAAAACAGGAGTCTCA
            I  Q  V  A  V  K  M  L  K  E  K  A  D  S  S  E  R  E  A  L
1981  ATCCAGGTTGCCGTCAAAATGCTGAAAGAAAAAGCAGACAGCTCTGAAAGAGAGGCACTC
            M  S  E  L  K  M  M  T  Q  L  G  S  H  E  N  I  V  N  L  L
2041  ATGTCAGAACTCAAGATGATGACCCAGCTGGGAAGCCACGAGAATATTGTGAACCTGCTG
            G  A  C  T  L  S  G  P  I  Y  L  I  F  E  Y  C  C  Y  G  D
2101  GGGGCGTGCACACTGTCAGGACCAATTTACTTGATTTTTGAATACTGTTGCTATGGTGAT
            L  L  N  Y  L  R  S  K  R  E  K  F  H  R  T  W  T  E  I  F
2161  CTTCTCAACTATCTAAGAAGTAAAAGAGAAAAATTTCACAGGACTTGGACAGAGATTTTC
            K  E  H  N  F  S  F  Y  P  T  F  Q  S  H  P  N  S  S  M  P
2221  AAGGAACACAATTTCAGTTTTTACCCCACTTTCCAATCACATCCAAATTCCAGCATGCCT
            G  S  R  E  V  Q  I  H  P  D  S  D  Q  I  S  G  L  H  G  N
2281  GGTTCAAGAGAAGTTCAGATACACCCGGACTCGGATCAAATCTCAGGGCTTCATGGGAAT
            S  F  H  S  E  D  E  I  E  Y  E  N  Q  K  R  L  E  E  E  E
2341  TCATTTCACTCTGAAGATGAAATTGAATATGAAAACCAAAAAAGGCTGGAAGAAGAGGAG
            D  L  N  V  L  T  F  E  D  L  L  C  F  A  Y  Q  V  A  K  G
2401  GACTTGAATGTGCTTACATTTGAAGATCTTCTTTGCTTTGCATATCAAGTTGCCAAAGGA
            M  E  F  L  E  F  K  S  C  V  H  R  D  L  A  A  R  N  V  L
2461  ATGGAATTTCTGGAATTTAAGTCGTGTGTTCACAGAGACCTGGCCGCCAGGAACGTGCTT
            V  T  H  G  K  V  V  K  I  C  D  F  G  L  A  R  D  I  M  S
2521  GTCACCCACGGGAAAGTGGTGAAGATATGTGACTTTGGATTGGCTCGAGATATCATGAGT
            D  S  N  Y  V  V  R  G  N  A  R  L  P  V  K  W  M  A  P  E
2581  GATTCCAACTATGTTGTCAGGGGCAATGCCCGTCTGCCTGTAAAATGGATGGCCCCCGAA
            S  L  F  E  G  I  Y  T  I  K  S  D  V  W  S  Y  G  I  L  L
2641  AGCCTGTTTGAAGGCATCTACACCATTAAGAGTGATGTCTGGTCATATGGAATATTACTG
```

Figure 1 (Continued)

```
           W  E  I  F  S  L  G  V  N  P  Y  P  G  I  P  V  D  A  N  F
2701  TGGGAAATCTTCTCACTTGGTGTGAATCCTTACCCTGGCATTCCGGTTGATGCTAACTTC
           Y  K  L  I  Q  N  G  F  K  M  D  Q  P  F  Y  A  T  E  E  I
2761  TACAAACTGATTCAAAATGGATTTAAAATGGATCAGCCATTTTATGCTACAGAAGAAATA
           Y  I  I  M  Q  S  C  W  A  F  D  S  R  K  R  P  S  F  P  N
2821  TACATTATAATGCAATCCTGCTGGGCTTTTGACTCAAGGAAACGGCCATCCTTCCCTAAT
           L  T  S  F  L  G  C  Q  L  A  D  A  E  E  A  M  Y  Q  N  V
2881  TTGACTTCGTTTTTAGGATGTCAGCTGGCAGATGCAGAAGAAGCGATGTATCAGAATGTG
           D  G  R  V  S  E  C  P  H  T  Y  Q  N  R  R  P  F  S  R  E
2941  GATGGCCGTGTTTCGGAATGTCCTCACACCTACCAAAACAGGCGACCTTTCAGCAGAGAG
           M  D  L  G  L  L  S  P  Q  A  Q  V  E  D  S  *
3001  ATGGATTTGGGGCTACTCTCTCCGCAGGCTCAGGTCGAAGATTCGTAGAGGAACAATTTA
3061  GTTTTAAGGACTTCATCCCTCCACCTATCCCTAACAGGCTGTAGATTACCAAAACAAGAT
3121  TAATTTCATCACTAAAAGAAAATCTATTATCAACTGCTGCTTCACCAGACTTTTCTCTAG
3181  AAGCTGTCTGCGTTTACTCTTGTTTTCAAAGGGACTTTTGTAAAATCAAATCATCCTGTC
3241  ACAAGGCAGGAGGAGCTGATAATGAACTTTATTGGAGCATTGATCTGCATCCAAGGCCTT
3301  CTCAGGC
```

Figure 2A The cDNA (SEQ ID NO: 3) and amino acid sequence (SEQ ID NO: 4) of CHv62.21 heavy chain. Double-underlined is the heavy chain variable region, and underlined is the heavy chain human IgG1 constant region.

```
        E  V  Q  L  V  E  S  G  G  G  L  V  R  P  G  G  S  L  R  L
   1    GAGGTGCAGCTGGTGGAGTCTGGGGGAGGCTTGGTCAGGCCTGGGGGGTCCCTGAGACTC
        S  C  A  A  S  G  F  T  F  S  G  Y  S  I  N  W  V  R  Q  A
  61    TCCTGTGCAGCCTCTGGATTCACCTTCAGTGGCTATAGCATAAACTGGGTCCGCCAGGCT
        P  G  K  G  L  E  W  V  S  S  I  S  S  S  S  N  Y  I  Y  Y
 121    CCAGGGAAGGGGCTGGAATGGGTCTCATCCATTAGTAGTAGTAGTAATTACATATACTAC
        A  D  S  V  K  G  R  F  T  I  S  R  D  N  A  K  N  S  L  Y
 181    GCAGACTCAGTGAAGGGCCGATTCACCATCTCCAGAGACAACGCCAAGAACTCACTGTAT
        L  Q  M  N  S  L  R  A  E  D  T  A  V  Y  Y  C  A  R  E  G
 241    CTGCAAATGAACAGCCTGAGAGCCGAGGACACGGCTGTGTATTACTGTGCGAGAGAAGGG
        F  I  A  G  T  T  F  D  A  F  D  I  W  G  Q  G  T  M  V  T
 301    TTTATAGCTGGAACTACTTTTGATGCTTTTGATATCTGGGGCCAAGGGACAATGGTCACC
        V  S  S  A  S  T  K  G  P  S  V  F  P  L  A  P  S  S  K  S
 361    GTCTCTTCAGCATCCACCAAGGGCCCATCGGTCTTCCCCCTGGCACCCTCCTCCAAGAGC
        T  S  G  G  T  A  A  L  G  C  L  V  K  D  Y  F  P  E  P  V
 421    ACCTCTGGGGGCACAGCGGCCCTGGGCTGCCTGGTCAAGGACTACTTCCCCGAACCGGTG
        T  V  S  W  N  S  G  A  L  T  S  G  V  H  T  F  P  A  V  L
 481    ACGGTGTCGTGGAACTCAGGCGCCCTGACCAGCGGCGTGCACACCTTCCCGGCTGTCCTA
        Q  S  S  G  L  Y  S  L  S  S  V  V  T  V  P  S  S  S  L  G
 541    CAGTCCTCAGGACTCTACTCCCTCAGCAGCGTGGTGACCGTGCCCTCCAGCAGCTTGGGC
        T  Q  T  Y  I  C  N  V  N  H  K  P  S  N  T  K  V  D  K  K
 601    ACCCAGACCTACATCTGCAACGTGAATCACAAGCCCAGCAACACCAAGGTGGACAAGAAA
        V  E  P  K  S  C  D  K  T  H  T  C  P  P  C  P  A  P  E  L
 661    GTTGAGCCCAAATCTTGTGACAAAACTCACACATGCCCACCGTGCCCAGCACCTGAACTC
        L  G  G  P  S  V  F  L  F  P  P  K  P  K  D  T  L  M  I  S
 721    CTGGGGGGACCGTCAGTCTTCCTCTTCCCCCCAAAACCCAAGGACACCCTCATGATCTCC
        R  T  P  E  V  T  C  V  V  V  D  V  S  H  E  D  P  E  V  K
 781    CGGACCCCTGAGGTCACATGCGTGGTGGTGGACGTGAGCCACGAAGACCCTGAGGTCAAG
        F  N  W  Y  V  D  G  V  E  V  H  N  A  K  T  K  P  R  E  E
 841    TTCAACTGGTACGTGGACGGCGTGGAGGTGCATAATGCCAAGACAAAGCCGCGGGAGGAG
        Q  Y  N  S  T  Y  R  V  V  S  V  L  T  V  L  H  Q  D  W  L
 901    CAGTACAACAGCACGTACCGTGTGGTCAGCGTCCTCACCGTCCTGCACCAGGACTGGCTG
        N  G  K  E  Y  K  C  K  V  S  N  K  A  L  P  A  P  I  E  K
 961    AATGGCAAGGAGTACAAGTGCAAGGTCTCCAACAAAGCCCTCCCAGCCCCCATCGAGAAA
        T  I  S  K  A  K  G  Q  P  R  E  P  Q  V  Y  T  L  P  P  S
1021    ACCATCTCCAAAGCCAAAGGGCAGCCCCGAGAACCACAGGTGTACACCCTGCCCCCATCC
        R  E  E  M  T  K  N  Q  V  S  L  T  C  L  V  K  G  F  Y  P
1081    CGGGAGGAGATGACCAAGAACCAGGTCAGCCTGACCTGCCTGGTCAAAGGCTTCTATCCC
        S  D  I  A  V  E  W  E  S  N  G  Q  P  E  N  N  Y  K  T  T
1141    AGCGACATCGCCGTGGAGTGGGAGAGCAATGGGCAGCCGGAGAACAACTACAAGACCACG
        P  P  V  L  D  S  D  G  S  F  F  L  Y  S  K  L  T  V  D  K
1201    CCTCCCGTGCTGGACTCCGACGGCTCCTTCTTCCTCTATAGCAAGCTCACCGTGGACAAG
        S  R  W  Q  Q  G  N  V  F  S  C  S  V  M  H  E  A  L  H  N
```

Figure 2A (Continued)

```
1261 AGCAGGTGGCAGCAGGGGAACGTCTTCTCATGCTCCGTGATGCATGAGGCTCTGCACAAC
      H  Y  T  Q  K  S  L  S  L  S  P  G  K  *
1321 CACTACACGCAGAAGAGCCTCTCCCTGTCTCCGGGTAAATAA
```

Figure 2B  The cDNA (SEQ ID NO : 5) and amino acid sequence (SEQ ID NO: 6) of CHv62.21 light chain. Double-underlined is the light chain variable region, and underlined is the human kappa constant region.

```
         D   I   Q   M   T   Q   S   P   S   S   L   S   A   S   V   G   D   R   V   T
  1    GACATCCAGATGACCCAGTCTCCATCCTCCCTGTCTGCATCTGTAGGAGACAGAGTCACC
         I   T   C   R   A   S   Q   G   I   R   N   D   L   G   W   Y   Q   Q   K   P
 61    ATCACTTGCCGGGCAAGTCAGGGCATTAGAAATGATTTAGGCTGGTATCAGCAGAAACCA
         G   K   A   P   K   R   L   I   Y   A   A   S   S   L   Q   S   G   V   P   S
121    GGGAAAGCCCCTAAGCGCCTGATCTATGCTGCATCCAGTTTGCAAAGTGGGGTCCCATCA
         R   F   S   G   S   G   S   G   T   E   F   T   L   T   I   S   S   L   Q   P
181    AGGTTCAGCGGCAGTGGATCTGGGACAGAATTCACTCTCACAATCAGCAGCCTGCAGCCT
         E   D   F   A   T   Y   Y   C   L   Q   H   N   G   F   P   Y   T   F   G   Q
241    GAAGATTTTGCAACTTATTACTGTCTACAGCATAATGGTTTCCCGTACACTTTTGGCCAG
         G   T   K   L   E   I   K   R   T   V   A   A   P   S   V   F   I   F   P   P
301    GGGACCAAGCTGGAGATCAAACGGACTGTGGCTGCACCATCTGTCTTCATCTTCCCGCCA
         S   D   E   Q   L   K   S   G   T   A   S   V   V   C   L   L   N   N   F   Y
361    TCTGATGAGCAGTTGAAATCTGGAACTGCCTCTGTTGTGTGCCTGCTGAATAACTTCTAT
         P   R   E   A   K   V   Q   W   K   V   D   N   A   L   Q   S   G   N   S   Q
421    CCCAGAGAGGCCAAAGTACAGTGGAAGGTGGATAACGCCCTCCAATCGGGTAACTCCCAG
         E   S   V   T   E   Q   D   S   K   D   S   T   Y   S   L   S   S   T   L   T
481    GAGAGTGTCACAGAGCAGGACAGCAAGGACAGCACCTACAGCCTCAGCAGCACCCTGACG
         L   S   K   A   D   Y   E   K   H   K   V   Y   A   C   E   V   T   H   Q   G
541    CTGAGCAAAGCAGACTACGAGAAACACAAAGTCTACGCCTGCGAAGTCACCCATCAGGGC
         L   S   S   P   V   T   K   S   F   N   R   G   E   C   *
601    CTGAGCTCGCCCGTCACAAAGAGCTTCAACAGGGGAGAGTGTTAA
```

Figure 2C The cDNA (SEQ ID NO : 7) and amino acid sequence (SEQ ID NO: 8) of CHv62.21 heavy chain modified with insertion of a non-natural amino acid. Marked with an X is location of the amber codon for insertion of the non-natural amino acid *para*-acetylphenylalanine (pAF) at nucleic acid residue 371. Double-underlined is the heavy chain variable region, and underlined is the heavy chain human IgG1 constant region.

```
        E  V  Q  L  V  E  S  G  G  G  L  V  R  P  G  G  S  L  R  L
   1  GAGGTGCAGCTGGTGGAGTCTGGGGGAGGCCTGGTCAGGCCTGGGGGGTCCCTGAGACTC
        S  C  A  A  S  G  F  T  F  S  G  Y  S  I  N  W  V  R  Q  A
  61  TCCTGTGCAGCCTCTGGATTCACCTTCAGTGGCTATAGCATAAACTGGGTCCGCCAGGCT
        P  G  K  G  L  E  W  V  S  S  I  S  S  S  S  N  Y  I  Y  Y
 121  CCAGGGAAGGGGCTGGAATGGGTCTCATCCATTAGTAGTAGTAGTAATTACATATACTAC
        A  D  S  V  K  G  R  F  T  I  S  R  D  N  A  K  N  S  L  Y
 181  GCAGACTCAGTGAAGGGCCGATTCACCATCTCCAGAGACAACGCCAAGAACTCACTGTAT
        L  Q  M  N  S  L  R  A  E  D  T  A  V  Y  Y  C  A  R  E  G
 241  CTGCAAATGAACAGCCTGAGAGCCGAGGACACGGCTGTGTATTACTGTGCGAGAGAAGGG
        F  I  A  G  T  T  F  D  A  F  D  I  W  G  Q  G  T  M  V  T
 301  TTTATAGCTGGAACTACTTTTGATGCTTTTGATATCTGGGGCCAAGGGACAATGGTCACC
        V  S  S  X  S  T  K  G  P  S  V  F  P  L  A  P  S  S  K  S
 361  GTCTCTTCATAGTCCACCAAGGGCCCATCGGTCTTCCCCCTGGCACCCTCCTCCAAGAGC
        T  S  G  G  T  A  A  L  G  C  L  V  K  D  Y  F  P  E  P  V
 421  ACCTCTGGGGGCACAGCGGCCCTGGGCTGCCTGGTCAAGGACTACTTCCCCGAACCGGTG
        T  V  S  W  N  S  G  A  L  T  S  G  V  H  T  F  P  A  V  L
 481  ACGGTGTCGTGGAACTCAGGCGCCCTGACCAGCGGCGTGCACACCTTCCCGGCTGTCCTA
        Q  S  S  G  L  Y  S  L  S  S  V  V  T  V  P  S  S  S  L  G
 541  CAGTCCTCAGGACTCTACTCCCTCAGCAGCGTGGTGACCGTGCCCTCCAGCAGCTTGGGC
        T  Q  T  Y  I  C  N  V  N  H  K  P  S  N  T  K  V  D  K  K
 601  ACCCAGACCTACATCTGCAACGTGAATCACAAGCCCAGCAACACCAAGGTGGACAAGAAA
        V  E  P  K  S  C  D  K  T  H  T  C  P  P  C  P  A  P  E  L
 661  GTTGAGCCCAAATCTTGTGACAAAACTCACACATGCCCACCGTGCCCAGCACCTGAACTC
        L  G  G  P  S  V  F  L  F  P  P  K  P  K  D  T  L  M  I  S
 721  CTGGGGGGACCGTCAGTCTTCCTCTTCCCCCCAAAACCCAAGGACACCCTCATGATCTCC
        R  T  P  E  V  T  C  V  V  V  D  V  S  H  E  D  P  E  V  K
 781  CGGACCCCTGAGGTCACATGCGTGGTGGTGGACGTGAGCCACGAAGACCCTGAGGTCAAG
        F  N  W  Y  V  D  G  V  E  V  H  N  A  K  T  K  P  R  E  E
 841  TTCAACTGGTACGTGGACGGCGTGGAGGTGCATAATGCCAAGACAAAGCCGCGGGAGGAG
        Q  Y  N  S  T  Y  R  V  V  S  V  L  T  V  L  H  Q  D  W  L
 901  CAGTACAACAGCACGTACCGTGTGGTCAGCGTCCTCACCGTCCTGCACCAGGACTGGCTG
        N  G  K  E  Y  K  C  K  V  S  N  K  A  L  P  A  P  I  E  K
 961  AATGGCAAGGAGTACAAGTGCAAGGTCTCCAACAAAGCCCTCCCAGCCCCCATCGAGAAA
        T  I  S  K  A  K  G  Q  P  R  E  P  Q  V  Y  T  L  P  P  S
1021  ACCATCTCCAAAGCCAAAGGGCAGCCCCGAGAACCACAGGTGTACACCCTGCCCCCATCC
        R  E  E  M  T  K  N  Q  V  S  L  T  C  L  V  K  G  F  Y  P
1081  CGGGAGGAGATGACCAAGAACCAGGTCAGCCTGACCTGCCTGGTCAAAGGCTTCTATCCC
        S  D  I  A  V  E  W  E  S  N  G  Q  P  E  N  N  Y  K  T  T
1141  AGCGACATCGCCGTGGAGTGGGAGAGCAATGGGCAGCCGGAGAACAACTACAAGACCACG
```

Figure 2C (Continued)

```
        P   P   V   L   D   S   D   G   S   F   F   L   Y   S   K   L   T   V   D   K
1201  CCTCCCGTGCTGGACTCCGACGGCTCCTTCTTCCTCTATAGCAAGCTCACCGTGGACAAG
        S   R   W   Q   Q   G   N   V   F   S   C   S   V   M   H   E   A   L   H   N
1261  AGCAGGTGGCAGCAGGGGAACGTCTTCTCATGCTCCGTGATGCATGAGGCTCTGCACAAC
        H   Y   T   Q   K   S   L   S   L   S   P   G   K   *
1321  CACTACACGCAGAAGAGCCTCTCCCTGTCTCCGGGTAAATAA
```

Figure 3A The amino acid sequence (SEQ ID NO: 9) of CHv62.21 heavy chain. Double-underlined is the heavy chain variable region, and underlined is the human IgG1 constant region.

```
  1  EVQLVESGGGLVRPGGSLRLSCAASGFTFSGYSINWVRQAPGKGLEWVSS
 51  ISSSSNYIYYADSVKGRFTISRDNAKNSLYLQMNSLRAEDTAVYYCAREG
101  FIAGTTFDAFDIWGQGTMVTVSSASTKGPSVFPLAPSSKSTSGGTAALGC
151  LVKDYFPEPVTVSWNSGALTSGVHTFPAVLQSSGLYSLSSVVTVPSSSLG
201  TQTYICNVNHKPSNTKVDKKVEPKSCDKTHTCPPCPAPELLGGPSVFLFP
251  PKPKDTLMISRTPEVTCVVVDVSHEDPEVKFNWYVDGVEVHNAKTKPREE
301  QYNSTYRVVSVLTVLHQDWLNGKEYKCKVSNKALPAPIEKTISKAKGQPR
351  EPQVYTLPPSREEMTKNQVSLTCLVKGFYPSDIAVEWESNGQPENNYKTT
401  PPVLDSDGSFFLYSKLTVDKSRWQQGNVFSCSVMHEALHNHYTQKSLSLS
451  PGK
```

Figure 3B The amino acid sequence (SEQ ID NO: 10) of CHv62.21 light chain. Double-underlined is the light chain variable region, and underlined is the human kappa constant region.

```
  1  DIQMTQSPSSLSASVGDRVTITCRASQGIRNDLGWYQQKPGKAPKRLIYA
 51  ASSLQSGVPSRFSGSGSGTEFTLTISSLQPEDFATYYCLQHNGFPYTFGQ
101  GTKLEIKRTVAAPSVFIFPPSDEQLKSGTASVVCLLNNFYPREAKVQWKV
151  DNALQSGNSQESVTEQDSKDSTYSLSSTLTLSKADYEKHKVYACEVTHQG
201  LSSPVTKSFNRGEC
```

Figure 3C The amino acid sequence (SEQ ID NO: 11) of CHv62.21 heavy chain. Amino acid position 124, marked with an X is location of the amber codon for insertion of the non-natural amino acid ("nnAA") *para*-acetylphenylalanine (pAF). Double-underlined is the heavy chain variable region, and underlined is the human IgG1 constant region.

```
  1  EVQLVESGGGLVRPGGSLRLSCAASGFTFSGYSINWVRQAPGKGLEWVSS
 51  ISSSSNYIYYADSVKGRFTISRDNAKNSLYLQMNSLRAEDTAVYYCAREG
101  FIAGTTFDAFDIWGQGTMVTVSSXSTKGPSVFPLAPSSKSTSGGTAALGC
151  LVKDYFPEPVTVSWNSGALTSGVHTFPAVLQSSGLYSLSSVVTVPSSSLG
201  TQTYICNVNHKPSNTKVDKKVEPKSCDKTHTCPPCPAPELLGGPSVFLFP
251  PKPKDTLMISRTPEVTCVVVDVSHEDPEVKFNWYVDGVEVHNAKTKPREE
301  QYNSTYRVVSVLTVLHQDWLNGKEYKCKVSNKALPAPIEKTISKAKGQPR
351  EPQVYTLPPSREEMTKNQVSLTCLVKGFYPSDIAVEWESNGQPENNYKTT
401  PPVLDSDGSFFLYSKLTVDKSRWQQGNVFSCSVMHEALHNHYTQKSLSLS
451  PGK
```

Figure 4A

Alignment of CHv62.21 heavy chain to human Ig germline.

Figure 4B

Alignment of CHv62.21 light chain to human Ig germline.

SQ 14-019

SQ 14-056

Figure 10
Cytotoxic activity of a 1b37.1 ligand blocking Mab is reduced in the presence of FL.
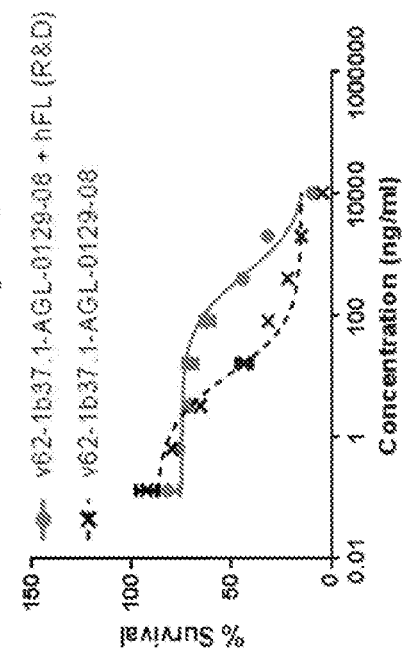
Figure 10A
CHv62.2.1 (Non ligand blocker)
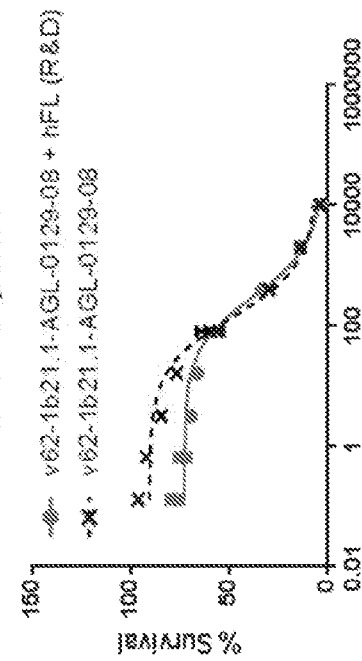
Figure 10B
1b37.1 (Ligand blocker)

Figure 11 - FLT3 Ligand does not interfere with CHv62.21pAF-AGL-0182-30 mediated cytotoxicity in MOLM-13 cells

*In vitro* Stability Comparison of CHv62.21pAF-AGL-0182-30 compared to FLT3 ADC CHv62-1b21-AGL-0301-20

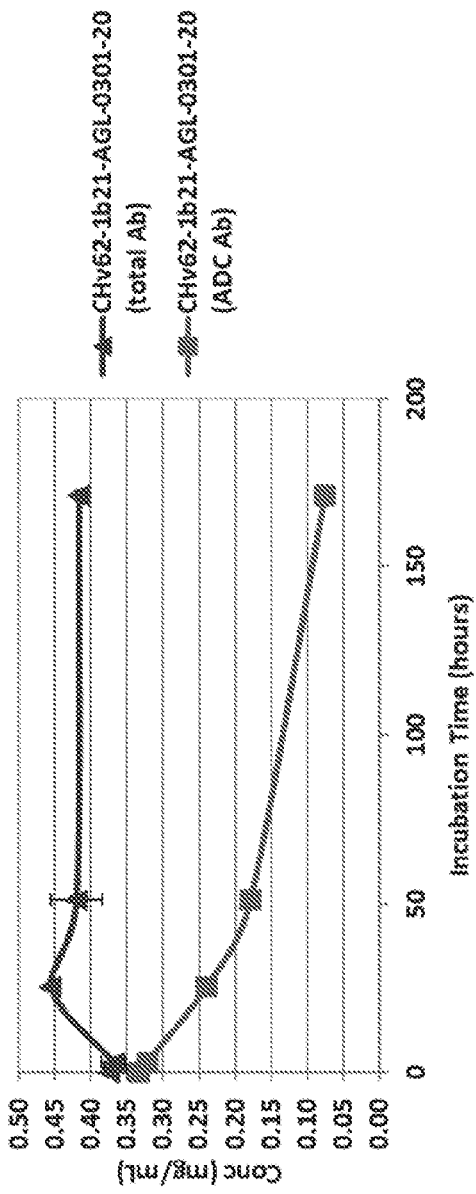
Figure 12B  Stability of cHv62-1b21-AGL-0301-20 in Human Serum

SEQUENCE LISTING

<160> NUMBER OF SEQ ID NOS: 34

<210> SEQ ID NO 1
<211> LENGTH: 3307
<212> TYPE: DNA
<213> ORGANISM: Homo sapiens
<220> FEATURE:
<223> OTHER INFORMATION: human FLT3

<400> SEQUENCE: 1

```
gttttacacg aggcggcatc gcagggctgg gccggcgcgg cctggggacc ccgggctccg      60
gaggccatgc cggcgttggc gcgcgacggc ggccagctgc cgctgctcgt tgttttttct     120
gcaatgatat ttgggactat tacaaatcaa gatctgcctg tgatcaagtg tgttttaatc     180
aatcataaga acaatgattc atcagtgggg aagtcatcat catatcccat ggtatcagaa     240
tccccggaag acctcgggtg tgcgttgaga ccccagagct cagggacagt gtacgaagct     300
gccgctgtgg aagtggatgt atctgcttcc atcacactgc aagtgctggt cgatgcccca     360
gggaacattt cctgtctctg ggtctttaag cacagctccc tgaattgcca gccacatttt     420
gatttacaaa acagaggagt tgtttccatg gtcattttga aaatgacaga acccaagct     480
ggagaatacc tactttttat tcagagtgaa gctaccaatt acacaatatt gtttacagtg     540
agtataagaa ataccctgct ttacacatta agaagacctt actttagaaa atggaaaac     600
caggacgccc tggtctgcat atctgagagc gttccagagc cgatcgtgga atgggtgctt     660
tgcgattcac aggggaaag ctgtaaagaa gaaagtccag ctgttgttaa aaaggaggaa     720
aaagtgcttc atgaattatt tgggatggac ataaggtgct gtgccagaaa tgaactgggc     780
agggaatgca ccaggctgtt cacaaatagat ctaaatcaaa ctcctcagac cacattgcca     840
caattatttc ttaaagtagg ggaacccta tggataaggt gcaaagctgt tcatgtgaac     900
catggattcg ggctcacctg ggaattagaa acaaagcac tcgaggaggg caactacttt     960
```

```
gagatgagta cctattcaac aaacagaact atgatacgga ttctgtttgc ttttgtatca    1020
tcagtggcaa gaaacgacac cggatactac acttgttcct cttcaaagca tcccagtcaa    1080
tcagctttgg ttaccatcgt agaaaaggga tttataaatg ctaccaattc aagtgaagat    1140
tatgaaattg accaatatga agagttttgt ttttctgtca ggtttaaagc ctacccacaa    1200
atcagatgta cgtggacctt ctctcgaaaa tcatttcctt gtgagcaaaa gggtcttgat    1260
aacggataca gcatatccaa gttttgcaat cataagcacc agccaggaga atatatattc    1320
catgcagaaa atgatgatgc ccaatttacc aaaatgttca cgctgaatat aagaaggaaa    1380
cctcaagtgc tcgcagaagc atcggcaagt caggcgtcct gtttctcgga tggatacccca   1440 ttaccatctt ggacctggaa gaagtgttca gacaagtctc ccaactgcac agaagagatc    1500
acagaaggag tctggaatag aaaggctaac agaaaagtgt ttggacagtg ggtgtcgagc    1560
agtactctaa acatgagtga agccataaaa gggttcctgg tcaagtgctg tgcatacaat    1620
tcccttggca catcttgtga gacgatcctt ttaaactctc caggcccctt ccctttcatc    1680
caagacaaca tctcattcta tgcaacaatt ggtgtttgtc tcctcttcat tgtcgtttta    1740
accctgctaa tttgtcacaa gtacaaaaag caatttaggt atgaaagcca gctacagatg    1800
gtacaggtga ccggctcctc agataatgag tacttctacg ttgatttcag agaatatgaa    1860
tatgatctca atgggagtt tccaagagaa aatttagagt ttgggaaggt actaggatca    1920
ggtgcttttg gaaagtgat gaacgcaaca gcttatggaa ttagcaaaac aggagtctca    1980
atccaggttg ccgtcaaaat gctgaaagaa aaagcagaca gctctgaaag agaggcactc    2040
atgtcagaac tcaagatgat gacccagctg ggaagccacg agaatattgt gaacctgctg    2100
ggggcgtgca cactgtcagg accaatttac ttgatttttg aatactgttg ctatggtgat    2160
cttctcaact atctcaagaag taaaagagaa aaatttcaca ggacttggac agagattttc    2220
aaggaacaca atttcagttt ttaccccact ttccaatcac atccaaattc cagcatgcct    2280
ggttcaagag aagttcagat acacccggac tcggatcaaa tctcagggct tcatgggaat    2340
tcatttcact ctgaagatga aattgaatat gaaaaccaaa aaaggctgga agaagaggag    2400
gacttgaatg tgcttacatt tgaagatctt ctttgctttg catatcaagt tgccaaagga    2460
atggaatttc tggaatttaa gtcgtgtgtt cacagagacc tggccgccag gaacgtgctt    2520
gtcacccacg ggaaagtggt gaagatatgt gactttggat tggctcgaga tatcatgagt    2580
gattccaact atgttgtcag gggcaatgcc cgtctgcctg taaaatggat ggccccgaa    2640 agcctgtttg aaggcatcta caccattaag agtgatgtct ggtcatatgg aatattactg    2700
tgggaaatct tctcacttgg tgtgaatcct taccctggca ttccggttga tgctaacttc    2760
tacaaactga ttcaaaatgg atttaaaatg gatcagccat tttatgctac agaagaaata    2820
tacattataa tgcaatcctg ctgggctttt gactcaagga acggccatc cttccctaat    2880 ttgacttcgt ttttaggatg tcagctggca gatgcagaag aagcgatgta tcagaatgtg    2940
gatggccgtg tttcggaatg tcctcacacc taccaaaaca ggcgaccttt cagcagagag    3000
atggatttgg ggctactctc tccgcaggct caggtcgaag attcgtagag gaacaattta    3060
gtttaaggga cttcatccct ccacctatcc ctaacaggct gtagattacc aaaacaagat    3120
taatttcatc actaaaagaa aatctattat caactgctgc ttcaccagac ttttctctag    3180
aagctgtctg cgtttactct tgttttcaaa gggacttttg taaaatcaaa tcatcctgtc    3240
acaaggcagg aggagctgat aatgaacttt attggagcat tgatctgcat ccaaggcctt    3300
ctcaggc                                                             3307
```

<210> SEQ ID NO 2
<211> LENGTH: 993
<212> TYPE: PRT
<213> ORGANISM: Homo sapiens
<220> FEATURE:
<223> OTHER INFORMATION: human FLT3

<400> SEQUENCE: 2

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Met Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365
```

```
Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Glu Asp Leu Asn Val Leu Thr
    770                 775                 780
```

```
Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
            805                 810                 815

Val Leu Val Thr His Gly Lys Val Lys Ile Cys Asp Phe Gly Leu
        820                 825                 830

Ala Arg Asp Ile Met Ser Asp Ser Asn Tyr Val Val Arg Gly Asn Ala
            835                 840                 845

Arg Leu Pro Val Lys Trp Met Ala Pro Glu Ser Leu Phe Glu Gly Ile
        850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
            885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
        930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 3
<211> LENGTH: 1362
<212> TYPE: DNA
<213> ORGANISM: Homo sapiens
<220> FEATURE:
<223> OTHER INFORMATION: CHv62.21 heavy chain

<400> SEQUENCE: 3
gaggtgcagc tggtggagtc tgggggaggc ctggtcaggc ctggggggtc cctgagactc      60
tcctgtgcag cctctggatt caccttcagt ggctatagca taaactgggt ccgccaggct     120
ccagggaagg ggctggaatg ggtctcatcc attagtagta gtagtaatta catatactac     180
gcagactcag tgaagggccg attcaccatc tccagagaca cgccaagaa ctcactgtat      240 ctgcaaatga acagcctgag agccgaggac acggctgtgt attactgtgc gagagaaggg     300
tttatagctg gaactacttt tgatgctttt gatatctggg gccaagggac aatggtcacc     360
gtctcttcag catccaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa      660 gttgagccca atcttgtga caaaactcac acatgcccac cgtgcccagc acctgaactc      720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
```

-continued

```
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat aa                      1362
```

<210> SEQ ID NO 4
<211> LENGTH: 453
<212> TYPE: PRT
<213> ORGANISM: Homo sapiens
<220> FEATURE:
<223> OTHER INFORMATION: CHv62.21 heavy chain

<400> SEQUENCE: 4

```
Glu Val Gln Leu Val Glu Ser Gly Gly Gly Leu Val Arg Pro Gly Gly
  1               5                  10                  15

Ser Leu Arg Leu Ser Cys Ala Ala Ser Gly Phe Thr Phe Ser Gly Tyr
             20                  25                  30

Ser Ile Asn Trp Val Arg Gln Ala Pro Gly Lys Gly Leu Glu Trp Val
         35                  40                  45

Ser Ser Ile Ser Ser Ser Ser Asn Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Phe Ile Ala Gly Thr Thr Phe Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
     290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
         355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
         435                 440                 445

Leu Ser Pro Gly Lys
    450

<210> SEQ ID NO 5
<211> LENGTH: 645
<212> TYPE: DNA
<213> ORGANISM: Homo sapiens
<220> FEATURE:
<223> OTHER INFORMATION: CHv62.21 light chain

<400> SEQUENCE: 5
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt tcccgtacac ttttggccag   300
gggaccaagc tggagatcaa acggactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttaa              645

<210> SEQ ID NO 6
<211> LENGTH: 214
<212> TYPE: PRT
<213> ORGANISM: Homo sapiens
<220> FEATURE:
<223> OTHER INFORMATION: CHv62.21 light chain

<400> SEQUENCE: 6

Asp Ile Gln Met Thr Gln Ser Pro Ser Ser Leu Ser Ala Ser Val Gly

```
            1               5                  10                 15
Asp Arg Val Thr Ile Thr Cys Arg Ala Ser Gln Gly Ile Arg Asn Asp
               20                  25                 30

Leu Gly Trp Tyr Gln Gln Lys Pro Gly Lys Ala Pro Lys Arg Leu Ile
            35                  40                 45

Tyr Ala Ala Ser Ser Leu Gln Ser Gly Val Pro Ser Arg Phe Ser Gly
            50                  55                 60

Ser Gly Ser Gly Thr Glu Phe Thr Leu Thr Ile Ser Ser Leu Gln Pro
65                  70                  75                 80

Glu Asp Phe Ala Thr Tyr Tyr Cys Leu Gln His Asn Gly Phe Pro Tyr
                     85                 90                  95

Thr Phe Gly Gln Gly Thr Lys Leu Glu Ile Lys Arg Thr Val Ala Ala
                100                 105                110

Pro Ser Val Phe Ile Phe Pro Pro Ser Asp Glu Gln Leu Lys Ser Gly
               115                 120                125

Thr Ala Ser Val Val Cys Leu Leu Asn Asn Phe Tyr Pro Arg Glu Ala
            130                 135                140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
            180                 185                190

Ala Cys Glu Val Thr His Gln Gly Leu Ser Ser Pro Val Thr Lys Ser
               195                 200                205

Phe Asn Arg Gly Glu Cys
   210

<210> SEQ ID NO 7
<211> LENGTH: 1362
<212> TYPE: DNA
<213> ORGANISM: Homo sapiens
<220> FEATURE:
<223> OTHER INFORMATION: CHv62.21 heavy chain

<400> SEQUENCE: 7
gaggtgcagc tggtggagtc tgggggaggc ctggtcaggc ctggggggtc cctgagactc      60
tcctgtgcag cctctggatt caccttcagt ggctatagca taaactgggt ccgccaggct     120
ccagggaagg ggctggaatg ggtctcatcc attagtagta gtagtaatta catatactac     180
gcagactcag tgaagggccg attcaccatc tccagagaca cgccaagaa ctcactgtat      240 ctgcaaatga acagcctgag agccgaggac acggctgtgt attactgtgc gagagaaggg     300
tttatagctg gaactacttt tgatgctttt gatatctggg gccaagggac aatggtcacc     360
gtctcttcat agtccaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa      660 gttgagccca atcttgtgac aaaactcac acatgcccac cgtgcccagc acctgaactc      720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
```

-continued

```
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagcccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat aa                      1362
```

<210> SEQ ID NO 8
<211> LENGTH: 453
<212> TYPE: PRT
<213> ORGANISM: Homo sapiens
<220> FEATURE:
<223> OTHER INFORMATION: CHv62.21 heavy chain
<220> FEATURE:
<221> NAME/KEY: VARIANT
<222> LOCATION: 124
<223> OTHER INFORMATION: Xaa = para-acetylphenylalanine (pAF)

<400> SEQUENCE: 8

```
Glu Val Gln Leu Val Glu Ser Gly Gly Gly Leu Val Arg Pro Gly Gly
1               5                  10                  15

Ser Leu Arg Leu Ser Cys Ala Ala Ser Gly Phe Thr Phe Ser Gly Tyr
            20                  25                  30

Ser Ile Asn Trp Val Arg Gln Ala Pro Gly Lys Gly Leu Glu Trp Val
        35                  40                  45

Ser Ser Ile Ser Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Phe Ile Ala Gly Thr Thr Phe Asp Ala Phe Asp Ile
            100                 105                 110

Trp Gly Gln Gly Thr Met Val Thr Val Ser Ser Xaa Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 9
<211> LENGTH: 453
<212> TYPE: PRT
<213> ORGANISM: Homo sapiens
<220> FEATURE:
<223> OTHER INFORMATION: CHv62.21 heavy chain

<400> SEQUENCE: 9

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Gly Tyr
            20                  25                  30

Ser Ile Asn Trp Val Arg Gln Ala Pro Gly Lys Gly Leu Glu Trp Val
        35                  40                  45

Ser Ser Ile Ser Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Phe Ile Ala Gly Thr Thr Phe Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 10
<211> LENGTH: 214
<212> TYPE: PRT
<213> ORGANISM: Homo sapiens
<220> FEATURE:
<223> OTHER INFORMATION: CHv62.21 light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Gly Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 453
<212> TYPE: PRT
<213> ORGANISM: homo sapiens
<220> FEATURE:
<223> OTHER INFORMATION: CHv62.21 heavy chain
<220> FEATURE:
<221> NAME/KEY: VARIANT
<222> LOCATION: 124
<223> OTHER INFORMATION: Xaa = para-acetylphenylalanine (pAF)

<400> SEQUENCE: 11

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Ser Gly Tyr
                20                  25                  30

Ser Ile Asn Trp Val Arg Gln Ala Pro Gly Lys Gly Leu Glu Trp Val
             35                  40                  45

Ser Ser Ile Ser Ser Ser Ser Asn Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Phe Ile Ala Gly Thr Thr Phe Asp Ala Phe Asp Ile
            100                 105                 110

Trp Gly Gln Gly Thr Met Val Thr Val Ser Ser Xaa Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
              180                 185                 190
Thr Val Pro Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
            210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
            290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
        450

<210> SEQ ID NO 12
<211> LENGTH: 449
<212> TYPE: PRT
<213> ORGANISM: Homo sapiens
<220> FEATURE:
<223> OTHER INFORMATION: v62-1b37.1 heavy chain

<400> SEQUENCE: 12

Glu Val Gln Leu Val Glu Ser Gly Gly Gly Val Val Arg Pro Gly Gly
1               5                   10                  15
Ser Leu Arg Leu Ser Cys Ala Ala Ser Gly Phe Thr Phe Asp Asp Tyr
                20                  25                  30
Gly Met Ser Trp Val Arg Gln Ala Pro Gly Lys Gly Leu Glu Trp Val
            35                  40                  45
Ser Gly Ile Asn Trp Asn Gly Ser Thr Gly Tyr Ala Asp Ser Val
            50                  55                  60
Lys Gly Arg Phe Thr Ile Ser Arg Asp Asp Ala Lys Asn Ser Leu Tyr
65                  70                  75                  80
Leu Gln Met Asn Ser Leu Arg Ala Glu Asp Thr Ala Leu Tyr His Cys
```

85                  90                  95
Ala Arg Asp Gly Tyr Thr Tyr Gly Pro Phe Asp Asn Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 214
<212> TYPE: PRT
<213> ORGANISM: Homo sapiens
<220> FEATURE:
<223> OTHER INFORMATION: v62-1b37.1 light chain

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Arg Asn Asp Leu Gly
1               5                   10

<210> SEQ ID NO 15
<211> LENGTH: 11
<212> TYPE: PRT
<213> ORGANISM: Homo sapiens

<400> SEQUENCE: 15

Arg Ala Ser Gln Gly Ile Arg Asn Asp Leu Gly
1               5                   10

<210> SEQ ID NO 16
<211> LENGTH: 7
<212> TYPE: PRT
<213> ORGANISM: Homo sapiens

<400> SEQUENCE: 16

Arg Asn Asp Leu Gly Trp Tyr
1               5

<210> SEQ ID NO 17
<211> LENGTH: 7
```

```
<212> TYPE: PRT
<213> ORGANISM: Homo sapiens

<400> SEQUENCE: 17

Ala Ala Ser Ser Leu Gln Ser
1               5

<210> SEQ ID NO 18
<211> LENGTH: 7
<212> TYPE: PRT
<213> ORGANISM: Homo sapiens

<400> SEQUENCE: 18

Ala Ala Ser Ser Leu Gln Ser
1               5

<210> SEQ ID NO 19
<211> LENGTH: 10
<212> TYPE: PRT
<213> ORGANISM: Homo sapiens

<400> SEQUENCE: 19

Arg Leu Ile Tyr Ala Ala Ser Ser Leu Gln
1               5                   10

<210> SEQ ID NO 20
<211> LENGTH: 9
<212> TYPE: PRT
<213> ORGANISM: Homo sapiens

<400> SEQUENCE: 20

Leu Gln His Asn Gly Phe Pro Tyr Thr
1               5

<210> SEQ ID NO 21
<211> LENGTH: 9
<212> TYPE: PRT
<213> ORGANISM: Homo sapiens

<400> SEQUENCE: 21

Leu Gln His Asn Gly Phe Pro Tyr Thr
1               5

<210> SEQ ID NO 22
<211> LENGTH: 9
<212> TYPE: PRT
<213> ORGANISM: Homo sapiens

<400> SEQUENCE: 22

Leu Gln His Asn Gly Phe Pro Tyr Thr
1               5

<210> SEQ ID NO 23
<211> LENGTH: 5
<212> TYPE: PRT
<213> ORGANISM: Homo sapiens

<400> SEQUENCE: 23

Gly Tyr Ser Ile Asn
1               5

<210> SEQ ID NO 24
<211> LENGTH: 7
<212> TYPE: PRT
<213> ORGANISM: Homo sapiens
```

<400> SEQUENCE: 24

Gly Phe Thr Phe Ser Gly Tyr
1               5

<210> SEQ ID NO 25
<211> LENGTH: 6
<212> TYPE: PRT
<213> ORGANISM: Homo sapiens

<400> SEQUENCE: 25

Ser Gly Tyr Ser Ile Asn
1               5

<210> SEQ ID NO 26
<211> LENGTH: 5
<212> TYPE: PRT
<213> ORGANISM: Homo sapiens

<400> SEQUENCE: 26

Gly Tyr Ser Ile Asn
1               5

<210> SEQ ID NO 27
<211> LENGTH: 7
<212> TYPE: PRT
<213> ORGANISM: Homo sapiens

<400> SEQUENCE: 27

Gly Phe Thr Phe Ser Gly Tyr
1               5

<210> SEQ ID NO 28
<211> LENGTH: 6
<212> TYPE: PRT
<213> ORGANISM: Homo sapiens

<400> SEQUENCE: 28

Ser Gly Tyr Ser Ile Asn
1               5

<210> SEQ ID NO 29
<211> LENGTH: 17
<212> TYPE: PRT
<213> ORGANISM: Homo sapiens

<400> SEQUENCE: 29

Ser Ile Ser Ser Ser Ser Asn Tyr Ile Tyr Tyr Ala Asp Ser Val Lys
1               5                   10                  15

Gly

<210> SEQ ID NO 30
<211> LENGTH: 5
<212> TYPE: PRT
<213> ORGANISM: Homo sapiens

<400> SEQUENCE: 30

Ser Ser Ser Ser Asn
1               5

<210> SEQ ID NO 31
<211> LENGTH: 12
<212> TYPE: PRT
<213> ORGANISM: Homo sapiens

```
<400> SEQUENCE: 31

Trp Val Ser Ser Ile Ser Ser Ser Asn Tyr Ile
1               5                   10

<210> SEQ ID NO 32
<211> LENGTH: 14
<212> TYPE: PRT
<213> ORGANISM: Homo sapiens

<400> SEQUENCE: 32

Glu Gly Phe Ile Ala Gly Thr Thr Phe Asp Ala Phe Asp Ile
1               5                   10

<210> SEQ ID NO 33
<211> LENGTH: 14
<212> TYPE: PRT
<213> ORGANISM: Homo saiens

<400> SEQUENCE: 33

Glu Gly Phe Ile Ala Gly Thr Thr Phe Asp Ala Phe Asp Ile
1               5                   10

<210> SEQ ID NO 34
<211> LENGTH: 15
<212> TYPE: PRT
<213> ORGANISM: Homo sapiens

<400> SEQUENCE: 34

Ala Arg Glu Gly Phe Ile Ala Gly Thr Thr Phe Asp Ala Phe Asp
1               5                   10                  15
```

ANTIBODY DRUG CONJUGATES (ADC) THAT BIND TO FLT3 PROTEINS

CROSS-REFERENCE TO RELATED APPLICATIONS

This application claims priority to U.S. Provisional Patent Application No. 62/130,476, filed 9 Mar. 2015. The contents of which are incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 511582009240SeqList.txt, date recorded: Mar. 7, 2016, size: 44,847 bytes).

STATEMENT OF RIGHTS TO INVENTIONS MADE UNDER FEDERALLY SPONSORED RESEARCH

Not applicable.

FIELD OF THE INVENTION

The invention described herein relates to antibodies, antigen-binding fragments thereof, and antibody drug conjugates (ADCs) thereof, that bind proteins, termed FLT3. The invention further relates to prognostic, prophylactic and therapeutic methods and compositions useful in the treatment of cancers that express FLT3.

BACKGROUND OF THE INVENTION

It is estimated that 1,660,290 men and women (854,790 men and 805,500 women) were diagnosed with and 580,350 men and women died of cancer of all sites in 2013. From 2006-2010, the median age at diagnosis for cancer of all sites was 66 years of age. The age-adjusted incidence rate was 463.0 per 100,000 men and women per year. These rates are based on cases diagnosed in 2006-2010 from 18 SEER geographic areas (N.B. SEER=Surveillance, Epidemiology, and End Results Program, NCI). From 2006-2010, the median age at death for cancer of all sites was 72 years of age. The age-adjusted death rate was 176.4 per 100,000 men and women per year. These rates are based on patients who died in 2006-2010 in the US. The overall 5-year relative survival for 2003-2009 from 18 SEER geographic areas was 65.8%.

Leukemias are cancers that start in blood-forming tissue such as the bone marrow and causes abnormally large numbers of blood cells to be produced and enter the bloodstream. The major leukemias are comprised of Acute Lymphoblastic (ALL), Acute Myeloid (AML), Chronic Lymphocytic (CLL), Chronic Myelogenous (CML), and Hairy Cell (CLL) Leukemia.

For these leukemias as a group, it is estimated that 48,610 men and women (27,880 men and 20,730 women) will be diagnosed with and 23,720 men and women will die of leukemia in 2013. From 2006-2010, the median age at diagnosis for leukemia was 66 years of age. The age-adjusted incidence rate was 12.8 per 100,000 men and women per year. These rates are based on cases diagnosed in 2006-2010 from 18 SEER geographic areas. From 2006-2010, the median age at death for leukemia was 75 years of age. The age-adjusted death rate was 7.1 per 100,000 men and women per year. These rates are based on patients who died in 2006-2010 in the US. The overall 5-year relative survival for 2003-2009 from 18 SEER geographic areas was 56.0%.

CLL is the second most common type of leukemia in adults and it usually gets worse slowly. It often occurs during or after middle age and it rarely occurs in children. Patients with early-stage CLL are not treated with chemotherapy until they become symptomatic or display evidence of rapid progression of disease. Early initiation of chemotherapy has failed to show benefit in CLL and may even increase mortality. When chemotherapy is initiated, the nucleoside analogue fludarabine is the most commonly used first-line therapy in CLL. Combination regimens have shown improved response rates in several clinical trials and include the following: Fludarabine, cyclophosphamide, and rituximab (FCR); Pentostatin, cyclophosphamide, and rituximab (PCR); Fludarabine, cyclophosphamide, and mitoxantrone (FCM); Cyclophosphamide, vincristine, and prednisone (CVP); Cyclophosphamide, doxorubicin, vincristine, and prednisone (CHOP). It is estimated that 15,680 men and women (9,720 men and 5,960 women) will be diagnosed with and 4,580 men and women will die of chronic lymphocytic leukemia in 2013. From 2006-2010, the median age at diagnosis for chronic lymphocytic leukemia was 71 years of age. The age-adjusted incidence rate was 4.3 per 100,000 men and women per year. These rates are based on cases diagnosed in 2006-2010 from 18 SEER geographic areas. From 2006-2010, the median age at death for chronic lymphocytic leukemia was 79 years of age. The age-adjusted death rate was 1.4 per 100,000 men and women per year. These rates are based on patients who died in 2006-2010 in the US. The overall 5-year relative survival for 2003-2009 from 18 SEER geographic areas was 79.2%.

Acute myeloid leukemia (AML) is the most common type of acute leukemia among adults. Current treatment of AML should be sufficiently aggressive to achieve complete remission (CR) because partial remission offers no substantial survival benefit. Remission rates in adult AML are inversely related to age, with an expected remission rate of more than 65% for those younger than 60 years. Data suggest that once attained, duration of remission may be shorter in older patients. Patients that express the progenitor cell antigen CD34 and/or the P-glycoprotein (MDR1 gene product) have an inferior outcome. Cytogenetic analysis provides some of the strongest prognostic information available, predicting outcome of both remission induction and post remission therapy. Cytogenetic abnormalities that indicate a good prognosis include t(8; 21), inv(16) or t(16;16), and t(15;17). Normal cytogenetics portends average-risk AML. Patients with AML that is characterized by deletions of the long arms or monosomies of chromosomes 5 or 7; by translocations or inversions of chromosome 3, t(6; 9), t(9; 22); or by abnormalities of chromosome 11q23 have particularly poor prognoses with chemotherapy. It is estimated that 14,590 men and women (7,820 men and 6,770 women) will be diagnosed with and 10,370 men and women will die of acute myeloid leukemia in 2013. From 2006-2010, the median age at diagnosis for acute myeloid leukemia was 67 years of age. The age-adjusted incidence rate was 3.7 per 100,000 men and women per year. These rates are based on cases diagnosed in 2006-2010 from 18 SEER geographic areas. From 2006-2010, the median age at death for acute myeloid leukemia was 72 years of age. The age-adjusted death rate was 2.8 per 100,000 men and women per year. These rates are based on patients who died in 2006-2010 in the US. The overall 5-year relative survival for 2003-2009 from 18 SEER geographic areas was 24.2%. Note, all general cancer information was obtained from the NCI website (www.cancer.gov) and all statistics are based on SEER incidence and NCHS mortality statistics found within: Howlader N., et. al., SEER Cancer Statistics Review, 1975-2010, National Cancer Institute. Bethesda, Md., http://seer.cancer.gov/csr/1975_2010/, based on November 2012 SEER data submission, posted to the SEER web site, 2013.

Acute lymphblastic leukemia ("ALL") represents a group of B/T-precursor-stage lymphoid cell malignancies arising from genetic alterations that block lymphoid differentiation and drive aberrant cell proliferation and survival. Remarkable strides have been made in the past several decades in treating childhood ALL, with five (5) year survival rates now approaching 90%. However up to 20% of children will be refractory to treatment or relapse following treatment and the event free survival rate for these patients remains poor. It also remains challenging to treat adult patients with ALL, with a high relapse rate even after significant progress in modern chemotherapy. In recent decades rapid improvements in the results of treatment of ALL have been achieved, which is mainly based on intensification and optimization of chemotherapy, risk-adapted use of stem-cell transplantation, as well as individualized and targeted therapy including monoclonal antibodies. Using next-generation sequencing, additional mutations affecting normal lymphopoiesis and the significance of cooperating mutations, as well as epigenetic alterations are being evaluated. The data obtained in this way will aid in the evaluation of prognosis in the individual patient but, importantly, also in incorporating targeted therapy appropriate for the mutational abnormality.

Further, the therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., Proc. Nat'l. Acad. Sci. USA 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.), formerly Abgenix, Inc.

Additionally, antibodies can be prepared using VelocImmune transgenic mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638,768, and 6,528,314.

SUMMARY OF THE INVENTION

The invention provides antibodies, antigen-binding fragments, and antibody drug conjugates (ADCs) thereof that bind to FLT3 proteins and polypeptide fragments of FLT3 proteins. In some embodiments, the invention comprises fully human antibodies conjugated with a therapeutic agent. In certain embodiments, there is a proviso that the entire nucleic acid sequence of FIGS. 2A and/or 2B is not encoded and/or the entire amino acid sequence of FIGS. 3A and/or 3B is not prepared. In certain embodiments, the entire nucleic acid sequence of FIGS. 2A and/or 2B is encoded and/or the entire amino acid sequence of FIGS. 3A and/or 3B is prepared, either of which are in respective human unit dose forms.

The invention further provides various immunogenic or therapeutic compositions, such as antibody drug conjugates, and strategies for treating cancers that express FLT3 such as cancers of tissues listed in Table I (e.g., AML, ALL, including B-cell lymphoblastic leukemia and precursor B-cell lymphoblastic leukemia).

BRIEF DESCRIPTION OF THE FIGURES

FIG. 1. The cDNA and amino acid sequence of FLT3 is shown in FIG. 1. The start methionine is underlined. The open reading frame extends from nucleic acid 67-3048 including the stop codon.

FIG. 2A. The cDNA and amino acid sequence of CHv62.21 heavy chain. Double-underlined is the heavy chain variable region, and underlined is the heavy chain human IgG1 constant region.

FIG. 2B. The cDNA and amino acid sequence of CHv62.21 light chain and CHv62.21pAF light chain. Double-underlined is the light chain variable region, underlined is the human kappa constant region.

FIG. 2C. The cDNA and amino acid sequence of CHv62.21 heavy chain modified with insertion of a non-natural amino acid. Marked with a X is the location of the amber codon for insertion of the non-natural amino acid ("nnAA") para-acetylphenylalanine (pAF) at nucleic acid residue 371. Double-underlined is the heavy chain variable region, and underlined is the heavy chain human IgG1 constant region.

FIG. 3A. The amino acid sequence of CHv62.21 heavy chain. Double-underlined is the heavy chain variable region, and underlined is the human IgG1 constant region.

FIG. 3B. The amino acid sequence of CHv62.21 light chain and CHv62.21pAF light chain. Double-underlined is the light chain variable region, and underlined is the human kappa constant region.

FIG. 3C. The amino acid sequence of CHv62.21 heavy chain. Amino acid position 124, marked with an X is location of the amber codon for insertion of the non-natural amino acid ("nnAA") para-acetylphenylalanine (pAF). Double-underlined is the heavy chain variable region, and underlined is the human IgG1 constant region.

FIG. 4A. Alignment of CHv62.21 heavy chain to human Ig germline.

FIG. 4B. Alignment of CHv62.21 light chain to human Ig germline.

FIG. 10. Cytotoxic Activity of a 1 b37.1 FLT3 Ligand Blocking Mab is reduced in the presence of FL. FIG. 10(A). Evaluation of the In-vitro cytotoxicity of v62-1b21.1-AGL-0129-08 with and without human FLT3 ligand (hFL) on RS-4-11 cells. FIG. 10(B). Evaluation of the In-vitro cytotoxicity of v62-1b37.1-AGL-0129-08 with and without human FLT3 ligand (hFL) on RS-4-11 cells.

FIG. 11. FLT3 Ligand Does Not Interfere with CHv62.21pAF-AGL-0182-30 Mediated Cytotoxicity in MOLM-13 cells.

FIG. 12(B). Evaluation of Stability of CHv62-AGL-0301-20 in Human Serum.

FIGS. 16A-15B. FLT3 expression in primary AML and normal samples.

DETAILED DESCRIPTION OF THE INVENTION

Figure 5:
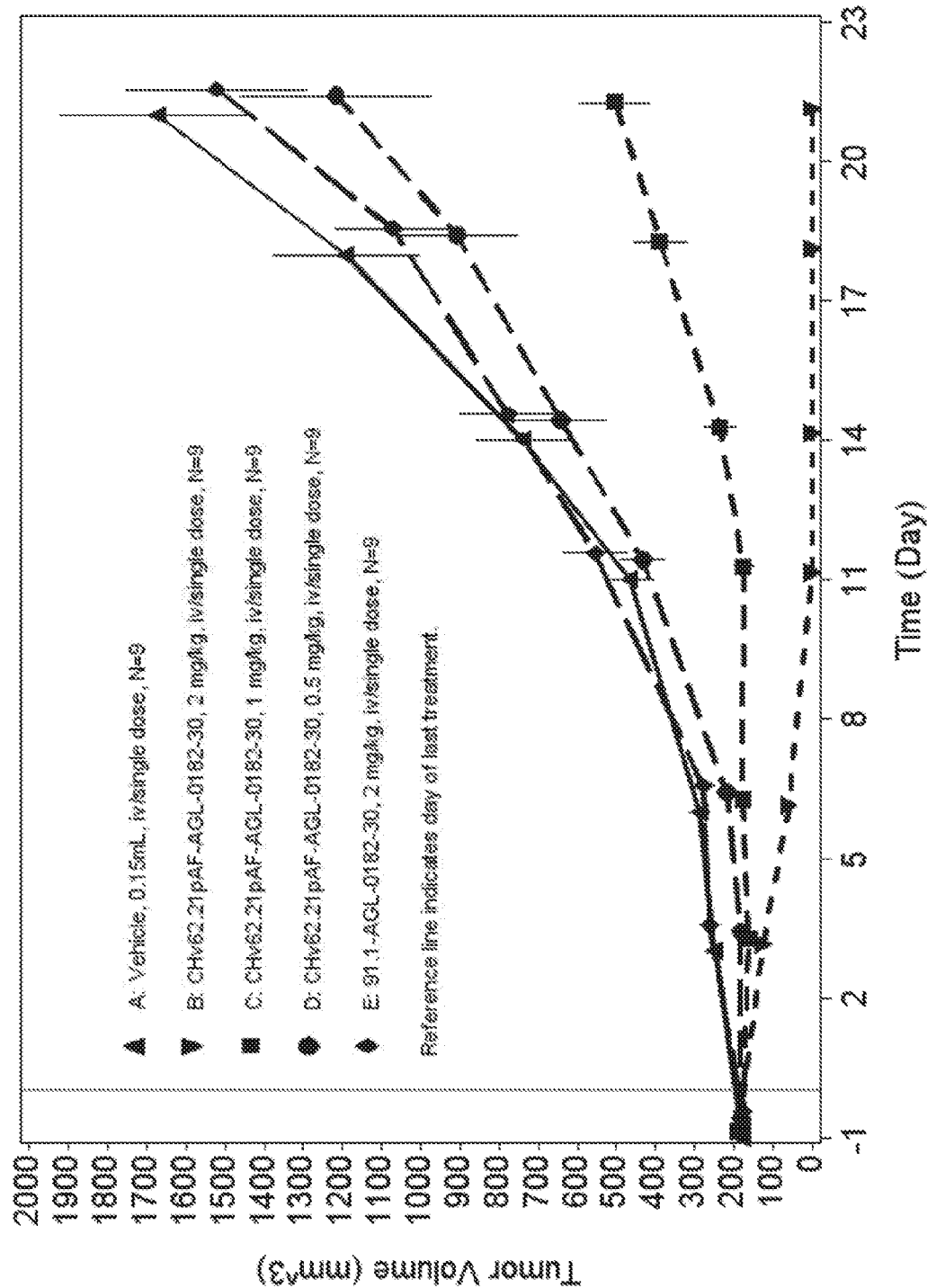
FIG. 5. Efficacy and Dose Titration Study of CHv62.21pAF-AGL-0182-30 in the subcutaneously established xenograft model of human B myelomonocytic leukemia cell line MV4-11 implanted in CB17/SCID mice.

Outline of Sections
I.) Definitions
II.) FLT3 Antibodies
III.) Antibody Drug Conjugates Generally
III(A). Maytansinoids
III(B). Auristatins and dolostatins
III(C). Calicheamicin
III(D). Other Cytotoxic Agents
IV.) Antibody Drug Conjugates which Bind FLT3
V.) Linker Units
VI.) The Stretcher Unit
VII.) The Amino Acid Unit
VIII.) The Spacer Unit
IX.) The Drug Unit
X.) Drug Loading
XI.) Methods of Determining Cytotoxic effect of ADCs
XII.) Treatment of Cancer(s) Expressing FLT3
XIII.) FLT3 as a Target for Antibody-based Therapy
XIV.) FLT3 ADC Cocktails
XV.) Combination Therapy
XVI.) Kits/Articles of Manufacture

I.) Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. Edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The term "alkyl," by itself or as part of another term, refers to a saturated $C_1$-$C_{12}$ hydrocarbon containing normal, secondary, tertiary or cyclic carbon atoms. Particular alkyl groups are those having 1 to 8 carbon atoms, 1 to 6 carbon atoms, or 1 to 4 carbon atoms. Examples of alkyl groups include, but are not limited to: methyl (Me), ethyl (Et), n-propyl, isopropyl, butyl, isobutyl, sec-butyl, tert-butyl (tBu), n-pentyl, isopentyl, tert-pentyl, and n-hexyl, isohexyl. In some embodiments, an alkyl group has normal, secondary, or tertiary carbon atoms and does not have cyclic carbon atoms.

The term "alkenyl," by itself or as part of another term, refers to a $C_2$-$C_{12}$ hydrocarbon containing normal, secondary, tertiary or cyclic carbon atoms with at least one site of unsaturation, i.e., a carbon-carbon, $sp^2$ double bond. Particular alkenyl groups are those having 2 to 8 carbon atoms, 2 to 6 carbon atoms, or 2 to 4 carbon atoms. Examples include, but are not limited to: vinyl (—CH═$CH_2$), allyl (—$CH_2CH_2$═$CH_2$), cyclopentenyl (—$C_5H_7$), and 5-hexenyl (—$CH_2CH_2CH_2CH_2CH$═$CH_2$). In some embodiments, an alkenyl group has normal, secondary, or tertiary carbon atoms and does not have cyclic carbon atoms.

The term "alkynyl," by itself or as part of another term, refers to a $C_2$-$C_{12}$ hydrocarbon containing normal, secondary, tertiary or cyclic carbon atoms with at least one site of unsaturation, i.e., a carbon-carbon, sp triple bond. Particular alkynyl groups are those having 2 to 8 carbon atoms, 2 to 6 carbon atoms, or 2 to 4 carbon atoms. Examples include, but are not limited to: ethynyl (—C≡CH) and 2-propynyl (—$CH_2$C≡CH). In some embodiments, an alkynyl group has normal, secondary, or tertiary carbon atoms and does not have cyclic carbon atoms.

The term "alkoxy" refers to an —O-alkyl group, where the O is the point of attachment to the rest of the molecule, and alkyl is as defined above.

The term "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. Particular heterocycloalkyl groups are those having from 3 to 8 ring atoms or from 5 to 7 ring atoms per ring structure. The ring structure may optionally contain up to two oxo groups on carbon or sulfur ring members. Illustrative entities, in the form of properly bonded moieties, include:

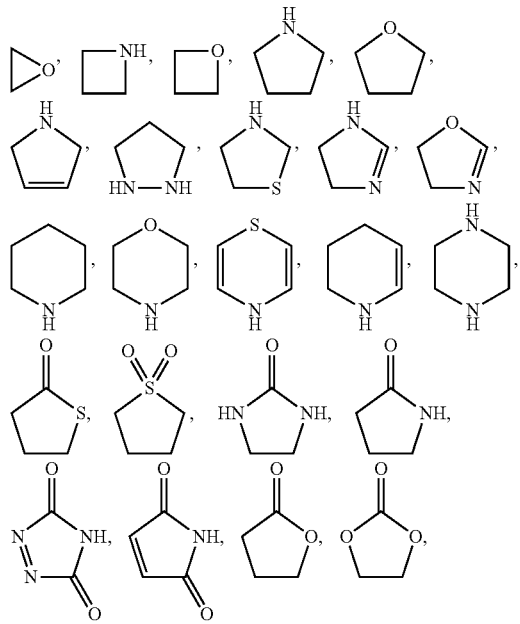

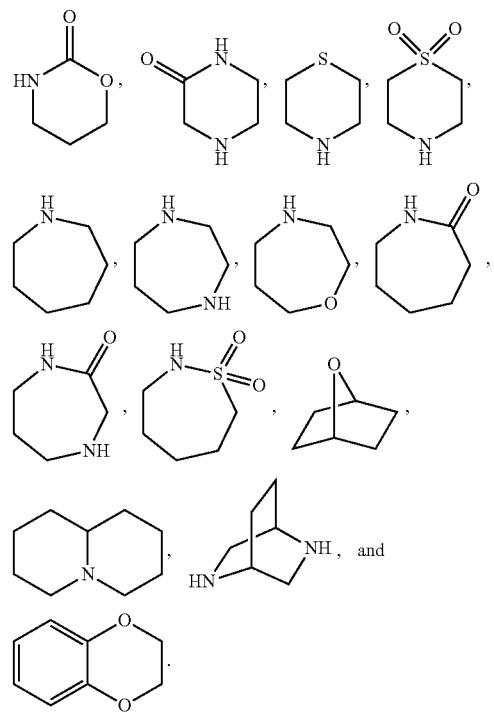

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Particular heteroaryl groups are those having from 3 to 8 ring atoms or from 5 to 7 ring atoms per ring structure. Illustrative examples of heteroaryl groups include the following entities, in the form of properly bonded moieties:

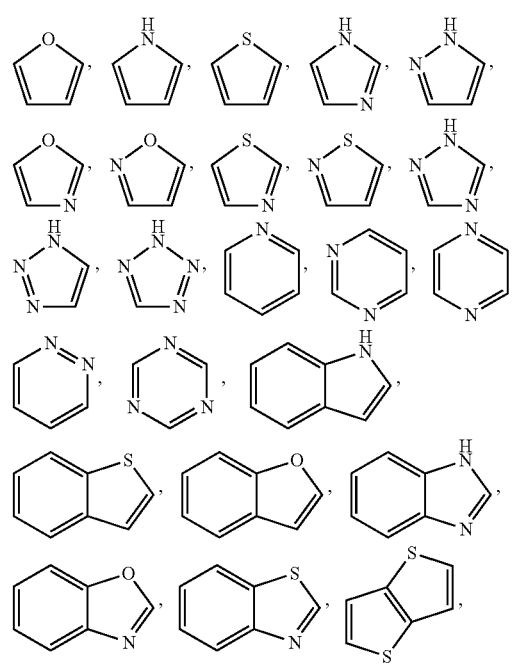

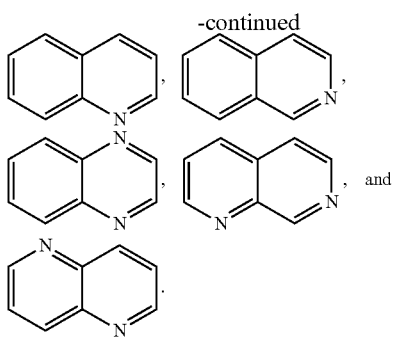
, and

The terms "heterocycle," "heterocyclic," or "heterocyclyl" as used herein encompass both the "heterocycloalkyl" and "heteroaryl" moieties as defined above.

Those skilled in the art will recognize that the species of heterocyclyl, heteroaryl and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, chlorine, and iodine, such as $^2H$, $^3H$, $^{11}C$, $^{13}C_1$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

The nomenclature "$C_{i\text{-}j}$" with j>i, when applied herein to a class of substituents, is meant to refer to embodiments of any of the compositions, uses, or methods described herein for which each and every one of the number of carbon members, from i to j including i and j, is independently realized. By way of example, the term $C_{1\text{-}3}$ refers independently to embodiments that have one carbon member ($C_1$), embodiments that have two carbon members ($C_2$), and embodiments that have three carbon members ($C_3$).

The term $C_{n\text{-}m}$alkyl refers to an aliphatic chain, whether straight or branched, with a total number N of carbon members in the chain that satisfies n≤N≤m, with m>n.

Chemical names listed herein were generated using AutoNOM™ software. If there is a discrepancy between a chemical structure and the name listed for that structure, the structure prevails.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

"Altering the native glycosylation pattern" is intended for purposes herein to mean deleting one or more carbohydrate moieties found in native sequence FLT3 (either by removing the underlying glycosylation site or by deleting the glycosylation by chemical and/or enzymatic means), and/or adding one or more glycosylation sites that are not present in the native sequence FLT3, wherein the "native glycosylation pattern" refers to the natural post-translational glycosylation pattern resulting from a particular combination of FLT-3 sequence, cell type, and growth conditions used. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a FLT3-related protein). For example, an analog of a FLT3 protein can be specifically bound by an antibody or T cell that specifically binds to FLT3.

The term "antibody" is used in the broadest sense unless clearly indicated otherwise. Therefore, an "antibody" can be naturally occurring or man-made such as monoclonal antibodies produced by conventional hybridoma or transgenic mice technology. FLT3 antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds FLT3 and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind FLT3 and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and at least one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective FLT3. See e.g., ANTIBODY ENGINEERING: A PRACTICAL APPROACH (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the FLT3 or its receptor.

The term "antigen-binding fragment" or "antibody fragment" of an antibody (or simply "antibody portion"), as used herein, refers to one or more fragments of a FLT3 antibody that retain the ability to specifically bind to an antigen (e.g., FLT3 and variants; see, FIG. 1). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "Fc", as used herein, refers to a region comprising a hinge region, $CH_2$ and/or $CH_3$ domains.

As used herein, any form of the "antigen" can be used to generate an antibody that is specific for FLT3. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion", in the context of an antigen, refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the FLT3 of interest.

The antibodies or antigen binding fragments thereof provided herein may constitute or be part of a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to, the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

The binding affinity of the antigen binding protein is determined by the association constant (Ka) and the dissociation constant (Kd) (KD=Kd/Ka). The binding affinity may be measured by BIACORE for example, by capture of the test antibody onto a protein-A coated sensor surface and flowing FLT3 over this surface. Alternatively, the binding affinity can be measured by FORTEBIO for example, with the test antibody receptor captured onto a protein-A coated needle and flowing FLT3 over this surface. One of skill in the art can identify other suitable assays known in the art to measure binding affinity.

The term "specifically binds", as used herein in relation to antigen binding, proteins means that the antigen binding protein binds to the FLT3 as well as a discrete domain, or discrete amino acid sequence, within FLT3 with no or insignificant binding to other (for example, unrelated) proteins. This term, however, does not exclude the fact that the antibodies or binding fragments thereof may also be cross-reactive with closely related molecules. The antibodies and fragments thereof as well as antibody drug conjugates comprising these described herein may specifically bind to FLT3, with at least 2, 5, 10, 50, 100, or 1000-fold greater affinity than they bind to closely related molecules.

The binding of any of the antibodies disclosed herein, in whatever form, e.g. in an antibody drug conjugate, to FLT3 could be expected to block some or all of FL binding to FLT3. However, herein are anti-FLT3 antibodies that do not substantially inihibit FL binding to FLT3. In order to "substantially inhibit" binding, one would expect a detectable amount of a decrease in binding beyond a de minimus change; a small change in binding that is equivalent to no more than a de minimus amount of binding as would be expected in random protein protein interactions or in non-specific antibody-antigen interactions is not encompassed. Measuring whether an antibody substantially inhibits binding of another molecule to the target antigen can be accomplished using a biophysical measurement or a functional measurement by methods that are known in the art. For example, the interaction of the two proteins can be measured directly in a physical binding assay (for example, see Example 14, infra), or indirectly via a functional assay that measures downstream effects of the protein interactions, such as signaling through a receptor or the subsequent cellular effects such as growth or inhibition of growth of a cell. Thus, the anti-FLT3 antibodies disclosed herein that do not substantially inhibit binding of FL to FLT3 do not cause a significant reduction in FL binding to FLT3, and signaling of FL binding through FLT3 is detectable.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

The monoclonal antibodies described herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison et al., Proc. Natl. Acad. Sci. USA 81: 6851-6855 (1984)).

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Tumors may be hematopoietic tumor, for example, tumors of blood cells or the like, meaning liquid tumors. Specific examples of clinical conditions based on such a tumor include leukemia such as chronic myelocytic leukemia or acute myelocytic leukemia; myeloma such as multiple myeloma; lymphoma and the like.

The term "therapeutic agent" refers to all agents that provide a therapeutic benefit and/or are therapeutically effective as defined herein. A therapeutic agent may, for example, reverse, ameliorate, alleviate, inhibit or limit the progress of, or lessen the severity of, a disease, disorder, or condition, or affect or improve or ameliorate one or more symptoms of disease, such as cancer. Such an agent may be cytotoxic or cytostatic. The term includes, but is not limited to, chemotherapeutic agents, anti-neoplastic agents and "Drug Unit" agents as defined herein.

The term "anti-neoplastic agent" refers to all agents that provide a therapeutic benefit and/or are therapeutically effective, as defined herein, in the treatment of a neoplasm or cancer.

In some embodiments employing any of the antibody drug conjugates and pharmaceutical compositions thereof as disclosed herein, the antibody drug conjugate comprising a therapeutic agent, and pharmaceutical compositions thereof, are also effective at treating a precancer or at least one pre-neoplastic cell, for example preventing malignant transformation to a cancerous cell. In other embodiments, the one or more anti-neoplastic agents are also effective at treating a precancer or at least one pre-neoplastic cell, for example preventing malignant transformation to a cancerous cell.

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., *J. Mol. Biol.* 262:732-745 (1996), "Antibody-antigen interactions: Contact analysis and binding site topography," *J. Mol. Biol.* 262, 732-745." ("Contact" numbering scheme), Lefranc M P et al., "IMGT unique numbering for immunoglobulin and T cell receptor variable domains and Ig superfamily V-like domains," *Dev Comp Immunol,* 2003 January; 27(1):55-77 ("IMGT" numbering scheme), and Honegger A and Plickthun A, "Yet another numbering scheme for immunoglobulin variable domains: an automatic modeling and analysis tool," *J Mol Biol,* 2001 Jun. 8; 309(3):657-70, (AHo numbering scheme).

The boundaries of a given CDR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. Table V, infra, lists the positions of CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given. See, for example Table V.

As used herein, the term "conservative substitution" refers to substitutions of amino acids and/or amino acid sequences that are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those set forth in Table II and Table(s) III(a-b). For example, such changes include substituting any of isoleucine (I), valine (V), and leucine (L) for any other of these hydrophobic amino acids;

aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III(a) herein; pages 13-15 "Biochemistry" 2nd ED. Lubert Stryer ed (Stanford University); Henikoff et al., PNAS 1992 Vol 89 10915-10919; Lei et al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins (e.g., auristatin E, auristatin F, MMAE and MMAF), auromycins, maytansinoids, ricin, ricin A-chain, combrestatin, duocarmycins, dolastatins, doxorubicin, daunorubicin, taxols, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$, radioactive isotopes of Lu including $Lu^{177}$, and toxins of the instant invention denoted AGD-0182.

Antibodies, including antibodies of the invention, may also be conjugated to any of the aforementioned cytotoxic agents and also to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90:6444-48 (1993).

The term "deplete," in the context of the effect of a FLT3 binding agent on FLT3-expressing cells, refers to a reduction in the number of or elimination of the FLT3-expressing cells. For the purposes of the present invention, FLT3, a.k.a., Fms like tyrosine kinase 3 receptor, also known as Flk2 (fetal liver kinase 2), STK1 (stem cell tyrosine kinase 1) and CD135, is a member of the type III receptor tyrosine kinases (RTKs). Human FLT3 encodes an RTK of 993 amino acids in length, which comprises membrane-bound receptor with five immunoglobulin-like extracellular domains and two intracellular tyrosine kinase domains (TKD) linked by a kinase-insert domain (Stirewalt D L et al; Nat Rev Cancer; 650-665(2003). Human FLT3 gene (Gene ID No.: 2322 (National Center for Biotechnology Information)) is located on chromosome 13q12 and share 85% amino acid sequence homology with mouse FLT3 (Rosnet O et al; Oncogene 8:173-179 (1993). FLT3 is expressed in normal myeloid and lymphoid progenitor cells and by the leukemic cells of 70-90% of AML patients (Carow, C. E et al; Blood 87: 1089-1096 (1996); Rosnet O et al; Leukemia 10:238-248 (1996) and also in ALL.

The term "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

The term "homolog" refers to a molecule which exhibits homology to another molecule, by for example, having sequences of chemical residues that are the same or similar at corresponding positions.

The term "identical" or "sequence identity" indicates the degree of identity between two nucleic acid or two amino acid sequences when optimally aligned and compared with appropriate insertions or deletions.

The "percent identity" between two sequences is a function of the number of identical positions shared by the sequences (i.e., % identity=number of identical positions/ total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers, et al., Comput. Appi. Biosci., 4:11-17 (1988), which has been incorporated into the ALIGN program (version 2.0), using a PAM120 weight residue table, a gap length penalty of 12 and a gap penalty of 4. In addition, the percent identity between two amino acid sequences can be determined using the Needleman, et al., J. Mol. Biol. 48:444-453 (1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence that is 100% identical to the reference sequence, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein by the numerical percent of the respective percent identity (divided by 100) and subtracting that product from said total number of nucleotides in the reference polynucleotide sequence, or: $n_n \leq x_n - (x_n \cdot y)$, wherein $n_n$ is the number of nucleotide alterations, $x_n$ is the total number of nucleotides in the reference polynucleotide sequence as described herein (see the nucleic acid sequences in the "Sequence Listing" for exemplary reference polynucleotides sequences), and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein (see the amino acid sequences in the "Sequence Listing" for exemplary reference polypeptide sequences), that is 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence by the numerical percent of the respective percent identity (divided by 100) and then subtracting that product from said total number of amino acids in the polypeptide reference sequence as described herein (see, for example SEQ ID NOs:1-21), or: $n_a \leq x_a - (x_a \cdot y)$, wherein $n_a$ is the number of amino acid alterations, $x_a$ is the total number of amino acids in the reference polypeptide sequence, and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, is the symbol for the multiplication operator, and wherein any non-integer product of $x_a$ and y is rounded down to the nearest integer prior to subtracting it from $x_a$.

The percent identity may be determined across the length of the sequence. As defined herein the term "over 75% identical" includes over 75%, 80%, 85%, 95% and 99% identity as well as all discrete values, and discrete subranges, with in this range.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., Immunol. Today 4: 72 (1983), EBV transformation technique (see, e.g., Cole et al. MONOCLONAL ANTIBODIES AND CANCER THERAPY 77-96 (1985)), or using phage display (see, e.g., Marks et al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, Adv. Drug Del. Rev. 31:33-42 (1998); Green, et al., J. Exp. Med. 188:483-95 (1998).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

The terms "inhibit" or "inhibition of" as used herein means to reduce by a measurable amount, or to prevent entirely.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the FLT3 genes or that encode polypeptides other than FLT3 gene product or fragments thereof. A skilled artisan can readily employ nucleic acid isolation procedures to obtain an isolated FLT3 polynucleotide. A protein is said to be "isolated," for example, when physical, mechanical or chemical methods are employed to remove the FLT3 proteins from cellular constituents that are normally associated with the protein. A skilled artisan can readily employ standard purification methods to obtain an isolated FLT3 protein. Alternatively, an isolated protein can be prepared by chemical means.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun et al., Nat. Biotechnol. 21:1473-79 (2003).

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage TxNxM+ under the TNM system.

The term "modified", as used herein refers to the presence of a change to a natural amino acid, a non-natural amino acid, a natural amino acid polypepetide or a non-natural amino acid polypeptide. Such changes, or modifications, may be obtained by post synthesis modifications of natural amino acids, non-natural amino acids, natural amino acid polypepetide or a non-natural amino acid polypeptide, or by co-translation, or by post-translational modifications of a natural amino acid, a non-natural amino acid, a natural amino acid polypepetide or a non-natural amino acid polypeptide.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates, or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "non-natural amino acid" or otherwise written as "nnAA" refers to an amino acid that is not one of the twenty (20) common amino acids or pyrolysine or selenocysteine. Other terms that may by used synonymously with the term nnAA is "non-natural encoded amino acid", "unnatural amino acid", "non-naturally occurring amino acid". Additionally, the term nnAA includes, but is not limited to, amino acids which do not occur naturally and may be obtained synthetically or may be obtained by modification of non-natural amino acids. For example, for the purposes of this invention, para-acetylphenylalanine is considered a nnAA.

The term "para-acetylphenylalanine" or "pAF" means 3-(4-acetylphenyl)-2-aminopropanoic acid as denoted by the following chemical structure:

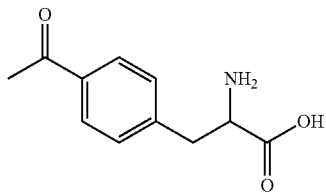

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter (See, Table III) or single letter designations for amino acids are used. In the art, this term is often used interchangeably with "peptide" or "protein".

A "recombinant" DNA or RNA molecule is a DNA or RNA molecule that has been subjected to molecular manipulation in vitro.

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the FLT3 antigen, but does not bind to the irrelevant antigen. In another embodiment, a specific antibody is one that binds human FLT3 antigen but does not bind a non-human FLT3 antigen with 70%, 75%, 80%, 85%, 90%, 91%, 92%, 93%, 94%, 95%, 96%, 97%, 98%, 99% or greater amino acid homology with the FLT3 antigen. In another embodiment, a specific antibody is one that binds human FLT3 antigen but does not bind a non-human FLT3 antigen with 70%, 75%, 80%, 85%, 90%, 91%, 92%, 93%, 94%, 95%, 96%, 97%, 98%, 99% or greater percent identity with the amino acid sequence of the FLT3 antigen. In another embodiment, a specific antibody is one that binds human FLT3 antigen and binds murine FLT3 antigen, but with a higher degree of binding the human antigen. In another embodiment, a specific antibody is one that binds human FLT3 antigen and binds primate FLT3 antigen, but with a higher degree of binding the human antigen. In another embodiment, the specific antibody binds to human FLT3 antigen and any non-human FLT3 antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "variant" refers to a molecule that exhibits a variation from a described type or norm, such as a protein that has one or more different amino acid residues in the corresponding position(s) of a specifically described protein (e.g. the FLT3 protein shown in FIG. 1.) An analog is an example of a variant protein. Splice isoforms and single nucleotides polymorphisms (SNPs) are further examples of variants.

The "FLT3 proteins" and/or "FLT3 related proteins" of the invention include those specifically identified herein (see, FIG. 1), as well as allelic variants, conservative substitution variants, analogs and homologs that can be isolated/ generated and characterized without undue experimentation following the methods outlined herein or readily available in the art. Fusion proteins that combine parts of different FLT3 proteins or fragments thereof, as well as fusion proteins of a FLT3 protein and a heterologous polypeptide are also included. Such FLT3 proteins are collectively referred to as the FLT3-related proteins, the proteins of the invention, or FLT3. The term "FLT3-related protein" refers to a polypeptide fragment or a FLT3 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 930, 935, 940, 945, 950, 955, 960, 965, 970, 975, 980, 985, 990, 991, 992, or 993 or more amino acids.

II.) FLT3 Antibodies

Another aspect of the invention provides antibodies that bind to FLT3-related proteins (See FIG. 1). In one embodiment, the antibody that binds to FLT3-related proteins is an antibody that specifically binds to FLT3 protein comprising amino acid sequence of SEQ ID NO.: 2. The antibody that specifically binds to FLT3 protein comprising amino acid sequence of SEQ ID NO.: 2 includes antibodies that can bind to other FLT3-related proteins. For example, antibodies that bind FLT3 protein comprising amino acid sequence of SEQ ID NO.: 2 can bind FLT3-related proteins such as FLT3 variants and the homologs or analogs thereof.

FLT3 antibodies of the invention are particularly useful in cancer (see, e.g., Table I), for prognostic assays, imaging, diagnostic, and therapeutic methodologies. In one embodiment is a FLT3 binding assay disclosed herein for use in detection of cancer, for example, in an immunoassay. Similarly, such antibodies are useful (e.g. when combined with a therapeutic agent, in an ADC, in the treatment, and/or prognosis of acute myeloid leukemia ("AML") and acute lymphoblastic leukemia (ALL), and other cancers, to the extent FLT3 is also expressed or overexpressed in these other cancers. Moreover, intracellularly expressed antibodies (e.g., single chain antibodies) are therapeutically useful in treating cancers in which the expression of FLT3 is involved, such as advanced or metastatic AML or ALL cancers or other advanced or metastatic cancers.

Various methods for the preparation of antibodies, specifically monoclonal antibodies, are well known in the art. For example, antibodies can be prepared by immunizing a suitable mammalian host using a FLT3-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of FLT3 can also be used, such as a FLT3 GST-fusion protein. In a particular embodiment, a GST fusion protein comprising all or most of the amino acid sequence of FIG. 1 is produced, and then used as an immunogen to generate appropriate antibodies. In another embodiment, a FLT3-related protein is synthesized and used as an immunogen.

In addition, naked DNA immunization techniques known in the art are used (with or without purified FLT3-related protein or FLT3 expressing cells) to generate an immune response to the encoded immunogen (for review, see Donnelly et al., 1997, Ann. Rev. Immunol. 15: 617-648).

The amino acid sequence of a FLT3 protein as shown in FIG. 1 can be analyzed to select specific regions of the FLT3 protein for generating antibodies. For example, hydrophobicity and hydrophilicity analyses of a FLT3 amino acid sequence are used to identify hydrophilic regions in the FLT3 structure. Regions of a FLT3 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of FLT3 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a FLT3 immunogen is often conducted by injection over a suitable time period and with use of a suitable adjuvant, as is understood in the art. During the immunization schedule, titers of antibodies can be taken to determine adequacy of antibody formation.

FLT3 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a FLT3-related protein. When the appropriate immortalized cell culture is identified, the cells can be expanded and antibodies produced either from in vitro cultures or from ascites fluid.

The antibodies or fragments of the invention can also be produced by recombinant means. Regions that bind specifically to the desired regions of a FLT3 protein can also be produced in the context of chimeric or complementarity-determining region (CDR) grafted antibodies of multiple species origin. Humanized or human FLT3 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

In a preferred embodiment, human monoclonal antibodies of the invention can be prepared using VelocImmune mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586,251, 6,596,541, 7,105,348, 6,528,313, 6,638, 768, and 6,528,314.

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859).

In another embodiment, fully human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and PCT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson, et al.

Additionally, human antibodies of the present invention can be made with techniques using transgenic mice, inactivated for antibody production, engineered with human heavy and light chains loci referred to as Xenomouse (Amgen Fremont, Inc., formerly Abgenix, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A. & Green, L. L., Curr. Opin. Biotechnol 13, 593-597 (2002).

Any of the methods of production above result in antibodies that have a certain ability to bind FLT3, or homologs or fragments or polypeptide sequences having 85, 90, 91, 92, 93, 94, 95, 96, 9, 98, or 99% sequence identity to FLT3. The binding affinity ($K_D$) of the antibodies, binding fragments thereof, and antibody drug conjugates comprising the same for FLT3 may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 micromolar and 500 micromolar or between 500 micromolar and 1 nM.

The binding affinity of the antigen binding protein is determined by the association constant (Ka) and the dissociation constant (Kd) (KD=Kd/Ka). The binding affinity may be measured by BIACORE for example, by capture of the test antibody onto a protein-A coated sensor surface and flowing FLT3 over this surface. Alternatively, the binding affinity can be measured by FORTEBIO for example, with the test antibody receptor captured onto a protein-A coated needle and flowing FLT3 over this surface. One of skill in the art can identify other suitable assays known in the art to measure binding affinity.

The term "specifically binds", as used herein in relation to antigen binding, proteins means that the antigen binding protein binds to the FLT3 as well as a discrete domain, or discrete amino acid sequence, within FLT3 with no or insignificant binding to other (for example, unrelated) proteins. This term, however, does not exclude the fact that the antibodies or binding fragments thereof may also be cross-reactive with closely related molecules. The antibodies and fragments thereof as well as antibody drug conjugates comprising these described herein may specifically bind to FLT3, with at least 2, 5, 10, 50, 100, or 1000-fold greater affinity than they bind to closely related molecules.

In a preferred embodiment, an FLT3 MAbs of the invention comprises heavy and light chain variable regions of an antibody designated CHv62.21 produced by a Chinese Hamster Ovary (CHO) cell deposited under the American Type Culture Collection (ATCC) Accession No.: PTA-121831 (See, FIGS. 3A and/or 3B), or heavy and light variable regions comprising amino acid sequences that are homologous to the amino acid sequences of the heavy and light chain variable regions of CHv62.21, and wherein the antibodies retain the desired functional properties of the FLT3 MAbs of the invention. The heavy chain variable region of CHv62.21 consists of the amino acid sequence ranging from $1^{st}$ residue (E) to the $123^{th}$ residue (S) residue of SEQ ID NO: 9, and the light chain variable region of CHv62.21 consists of the amino acid sequence ranging from $1^{st}$ residue (D) to the $108^{th}$ residue (R) residue of SEQ ID NO: 10. The CDR1-3 (Kabat) of heavy chain variable region of CHv62.21 consists of the amino acid sequence ranging from 31-35, from 50-65, and from 95-102 of SEQ ID NO: 9 respectively, and the CDR1-3 (Kabat or Chothia) of the light chain variable region of CHv62.21 consists of the amino acid sequence ranging from 24-34, from 50-56, and from 89-97 of SEQ ID NO: 10 respectively (See, FIG. 4 and Table V). As the constant region of the antibody of the invention, any subclass of constant region can be chosen. In one embodiment, human IgG1 constant region as the heavy chain constant region and human Ig kappa constant region as the light chain constant region can be used.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% identical to heavy chain variable region amino acid sequence set forth in FIGS. 3A and/or 3B; and (b) the light chain variable region comprises an amino acid sequence that is at least 80% identical to the light chain variable region amino acid sequence set forth in FIGS. 3A and/or 3B.

In other embodiments, the $V_H$ and/or $V_L$ amino acid sequences are 85%, 86%, 87%, 88%, 89%, 90%, 91%, 92%, 93%, 94%, 95%, 96%, 97%, 98% or 99% identical to the $V_H$ and $V_L$ sequences set forth in FIGS. 3A and/or 3B. The disclosure herein also provides for polynucleotides or nucleic acids encoding a or b, or the VH or VL sequences set forth in FIGS. 3A and/or 3B, as well as polynucleotides or nucleic acids that are 85%, 86%, 87%, 88%, 89%, 90%, 91%, 92%, 93%, 94%, 95%, 96%, 97%, 98% or 99% percent identical to these.

In another embodiment, the invention provides an isolated monoclonal antibody, or antigen binding portion thereof, comprising a humanized heavy chain variable region and a humanized light chain variable region, wherein:

(a) the heavy chain variable region comprises complementarity determining regions (CDRs) having the amino acid sequences of the heavy chain variable region CDRs set forth in FIGS. 3A and/or 3B;

(b) the light chain variable region comprises CDRs having the amino acid sequences of the light chain variable region CDRs set forth in FIGS. 3A and/or 3B.

Engineered antibodies of the invention include those in which modifications have been made to framework residues within $V_H$ and/or $V_L$ (e.g. to improve the properties of the antibody). Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr, et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a FLT3 MAb of the invention may be chemically modified (e.g., one or more chemical moieties can be attached to the antibody) or be modified to alter its glycosylation, again to alter one or more functional properties of the MAb. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer, et al. The number of cysteine residues in the hinge region of CH1 is altered to, for example, facilitate assembly of the light and heavy chains or to increase or decrease the stability of the FLT3 MAb.

In another embodiment, the Fc hinge region of an antibody is mutated to decrease the biological half life of the FLT3 MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward, et al.

In another embodiment, the FLT3 MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the FLT3 MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter, et al.

In another embodiment, heavy chain is altered by replacing at least one amino acid residue with non-natural amino acid through the ReCODE technology developed by Ambrx (La Jolla, Calif.). One example of non-natural amino acid is para-acetylphenylalanine.

Reactivity of FLT3 antibodies with a FLT3-related protein can be established by a number of well known means, including Western blot, immunoprecipitation, ELISA, and FACS analyses using, as appropriate, FLT3-related proteins, FLT3-expressing cells or extracts thereof. A FLT3 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more FLT3 epitopes are generated using methods generally known in the art. Homodimeric antibodies can also be generated by cross-linking techniques known in the art (e.g., Wolff et al., Cancer Res. 53: 2560-2565).

In yet another preferred embodiment, the FLT3 MAb of the invention is an antibody comprising heavy and light chain of an antibody designated CHv62.21. The heavy chain of CHv62.21 consists of the amino acid sequence ranging from $1^{st}$ residue (E) to the $453^{rd}$ residue (K) of SEQ ID NO: 9 and the light chain of CHv62.21 consists of amino acid sequence ranging from $1^{st}$ residue (D) to the $214^{th}$ residue (C) of SEQ ID NO: 10 sequence. The sequence of which is set forth in FIGS. 2A and/or 2B and FIGS. 3A and/or 3B. In a preferred embodiment, CHv62.21 is modified with a non-natural amino acid ("nnAA") and conjugated to a cytotoxic agent. In one embodiment, the nnAA is pAF. In a preferred embodiment, the cytotoxic agent is specifically conjugated at the nnAA.

In yet another embodiment, the FLT3 MAb of the invention is produced by the method of producing an antibody or antigen binding fragment comprising culturing a host cell to allow expression of antibody or antigen binding fragment, wherein the host cell is selected from the group consisting of the following (a) to (c):

(a) a host cell transfected with an expression vector comprising a polynucleotide comprising a base sequence encoding a heavy chain variable region consisting of the amino acid sequence ranging from the 1st E to the 123$^{rd}$ S of SEQ ID NO: 9 and a polynucleotide comprising a base sequence encoding a light chain variable region consisting of the amino acid sequence ranging from the 1st D to the 108th R of SEQ ID NO: 10;

(b) a host cell transfected with an expression vector comprising a polynucleotide comprising a base sequence encoding a heavy chain variable region consisting of the amino acid sequence ranging from the 1st E to the 123$^{rd}$ S of SEQ ID NO: 9 and an expression vector comprising a polynucleotide comprising a base sequence encoding a light chain variable region consisting of the amino acid sequence ranging from the 1st D to the 108th R SEQ ID NO: 10; and (c) a host cell transfected with an expression vector comprising a polynucleotide comprising a base sequence encoding a heavy chain variable region consisting of the amino acid sequence ranging from the 1st E to the 123$^{rd}$ S of SEQ ID NO: 9 and a host cell transfected with an expression vector comprising a polynucleotide comprising a base sequence encoding a light chain variable region consisting of the amino acid sequence ranging from the 1st D to the 108th R of SEQ ID NO: 10.

In yet another embodiment, the FLT3 MAb of the invention is produced by the method of producing an antibody comprising culturing a host cell to allow expression of antibody, wherein the host cell is selected from the group consisting of the following (a) to (c):

(a) a host cell transformed with an expression vector comprising a polynucleotide comprising a base sequence encoding a heavy chain consisting of the amino acid sequence ranging from the 1st E to the 453$^{rd}$ K of SEQ ID NO: 9 and a polynucleotide comprising a base sequence encoding a light chain consisting of the amino acid sequence ranging from the 1st D to the 214th C of SEQ ID NO: 10;

(b) a host cell transformed with an expression vector comprising a polynucleotide comprising a base sequence encoding a heavy chain consisting of the amino acid sequence ranging from the 1st E to the 453$^{rd}$ K of SEQ ID NO: 9 and an expression vector comprising a polynucleotide comprising a base sequence encoding a light chain consisting of the amino acid sequence ranging from the 1st D to the 214th C of SEQ ID NO: 10; and (c) a host cell transformed with an expression vector comprising a polynucleotide comprising a base sequence encoding a heavy chain consisting of the amino acid sequence ranging from the 1st E to the 453th K of SEQ ID NO: 9 and a host cell transformed with an expression vector comprising a polynucleotide comprising a base sequence encoding a light chain consisting of the amino acid sequence ranging from the 1st D to the 214th C of SEQ ID NO: 10.

The Chinese Hamster Ovary (CHO) cell producing the antibody designated CHv62.21 was sent (via Federal Express) to the American Type Culture Collection (ATCC), P.O. Box 1549, Manassas, Va. 20108 on 9 Dec. 2014 and assigned Accession number PTA-121831.

Alternatively, or additionally, in another embodiment of the invention, the MAbs which bind FLT3, in this case, the MAb CHv62.21 may undergo post-translational modifications as known in the art. Examples of post-translational modifications include, but are not limited to, chemical modifications, such as disulfide bonds, oligosaccharides, N-terminal pyroglutamate formation, C-terminal lysine processing, deamidation, isomerization, oxidation, glycation, peptide bond cleavage, non-reductible cross-linking, truncation and others known in the art. See, Liu, et. al., Heterogeneity of Monoclonal Antibodies, J. Pharma. Sci. vol. 97, no. 7, pp. 2426-2447 (July 2008). Other types of modifications include noncovalent interaction, conformational heterogeneity, and aggregation. Id.

In a further embodiment, the CHv62.21 MAb comprises a cyclization of the N-terminal heavy chain Glutamate at residue 1 to Pyro-Glutamate. One of skill in the art will understand and appreciate that such cyclization is understood to occur spontaneously. See, Dick, et. al., Determination of the Origin of the N-Terminal Pyro-Glutamtate Variation in Monoclonal Antibodies Using Model Peptides, Biotechnology and Bioengineering, vol. 97, no. 3, pp 544-553 (Jun. 15, 2007).

Additionally or alternatively, amino acids of the CHv62.21 MAb may undergo further post-translational modifications including, but not limited to, deamidation, isomerization, glycation, and/or oxidation. The polypeptides of the invention, or the fragments thereof, may undergo additional post-translational modifications, including glycosylation, for example N-linked or O-linked glycosylation sites that are well known in the art. As previous described, changes may be made in the amino acid sequence of the polypeptide or process conditions (such as changes in culture, purification, and/or storage conditions) to preclude or minimize such alterations, or to facilitate them in circumstances where such processing is beneficial. Moreover, such preparations may comprise polypeptides that have varying levels of more than one type of processing related modification(s), for example, a polypeptide may have some, most, or substantially all of a C-terminal lysine removed and/or some, most, or substantially all of an N-terminal amino acid converted to pyroglutamatic acid (for example, the polypeptides shown in FIGS. 2A and/or 2B or FIGS. 3A and/or 3B or in the consensus sequences or antigen-binding fragments). Process conditions such as varying buffer composition and temperature can have significant effects on the extent of such modifications.

In a further embodiment, the CHv62.21 MAb comprises a truncation of the C-terminal heavy chain Lysine at residue 453 of SEQ ID NO: 9.

In a further embodiment, the CHv62.21 MAb comprises an addition of glycosylation(s) to the heavy chain Asparagine at residue 303 including, but not limited to, G0 (Asialo-, agalacto, afucosylated bi-antennary complex-type N-glycan; G0F (Asialo-, agalacto, core-fucosylated bi-antennary complex-type N-glycan); Mannose-5 (N-linked Oligomannose-5); G1F (Asialo-, monogalacto, core-fucosylated bi-antennary complex-type N-glycan); G2 (Asialo-, bigalacto, afucosylated bi-antennary complex-type N-glycan); G2F (Asialo-. bigalacto, core-fucosylated bi-antennary complex-type N-glycan); A1 (monosialylated, biantennary N-linked oligosaccharide, Neu5Acid); and/or A2 (Disialylated, biantennary N-linked oligosaccharaide Neu5Acid).

Additionally, or alternatively in another embodiment, the CHv62.21 MAb comprises the addition of glycation(s) to one or more Serine residues of the light chain. Generally, glycation results from the nonenzymatic reaction between reducing sugars and the N-terminal primary amine or the amine group of lysine side chains. One of skill in the art will understand and appreciate that glycation can mask the positive charge on the N-terminal primary amino acid group or the side chain of lysine residues, which will make the antibody more acidic.

The amino acid sequence of the polypeptides of the invention may be verified by any means known in the art (for example, mass spectrometry) and may be identical to the sequences disclosed herein (See, FIGS. 2A and/or 2B and FIGS. 3A and/or 3B) or may differ from those sequences at one or more amino acid residues as a result of post-translational modification processing. By way of non-limiting example, on all or a portion of the substantially homogenous polypeptides, a C-terminal amino acid from either the light chain or heavy chain may be removed, by proteolytic processing or other processing that occurs during culture. Similarly, N-terminal amino acids may be absent, for example, one (1), two (2), three (3), four (4), or five (5) N-terminal amino acids may be absent.

In another embodiment, the heavy chain variable region of CHv62.21 MAb is selected from the group consisting of an amino acid sequence ranging from residue 1 (E) to residue 123 (S) of SEQ ID NO: 9 and an amino acid sequence ranging from residue 1 (E) to residue 123 (S) of SEQ ID NO: 9 wherein the N-terminal residue 1 (E) is converted to pyroglutamic acid.

In another embodiment, the heavy chain of CHv62.21 MAb is selected from the group consisting of an amino acid sequence ranging from residue 1 (E) to residue 453 (K) of SEQ ID NO: 9, an amino acid sequence ranging from residue 1 (E) to residue 453 (K) of SEQ ID NO: 9 wherein the N-terminal residue 1 (E) is converted to pyroglutamic acid, an amino acid sequence ranging from residue 1 (E) to residue 453 (K) of SEQ ID NO: 9 wherein the C-terminal residue 453 (K) is removed, and an amino acid sequence ranging from residue 1 (E) to residue 453 (K) of SEQ ID NO: 9 wherein the N-terminal residue 1 (E) is converted to pyroglutamic acid and the C-terminal residue 453 (K) is removed.

In another embodiment, the CHv62.21 MAb or antigen-binding fragment thereof is a recombinantly-produced mixture of proteins obtained by expression in a host cell, wherein the heavy chain variable region of the antibody or antigen-binding fragment thereof is selected from the group consisting of an amino acid sequence ranging from residue 1 (E) to residue 123 (S) of SEQ ID NO: 9 and an amino acid sequence ranging from residue 1 (E) to residue 123 (S) of SEQ ID NO: 9 wherein the N-terminal residue 1 (E) is converted to pyroglutamic acid.

In another embodiment, the CHv62.21 MAb is a recombinantly-produced mixture of proteins obtained by expression in a host cell, wherein the heavy chain of the antibody is selected from the group consisting of an amino acid sequence ranging from residue 1 (E) to residue 453 (K) of SEQ ID NO: 9, an amino acid sequence ranging from residue 1 (E) to residue 453 (K) of SEQ ID NO: 9 wherein the N-terminal residue 1 (E) is converted to pyroglutamic acid, an amino acid sequence ranging from residue 1 (E) to residue 453 (K) of SEQ ID NO: 9 wherein the C-terminal residue 453 (K) is removed, and an amino acid sequence ranging from residue 1 (E) to residue 453 (K) of SEQ ID NO: 9 wherein the N-terminal residue 1 (E) is converted to pyroglutamic acid and the C-terminal residue 453 (K) is removed.

In another embodiment, the CHv62.21 MAb comprises the heavy chain consisting of the amino acid sequence ranging from the 1st E to the $453^{rd}$ K of SEQ ID NO: 9 wherein 1st E is modified to pyro-glutamate and the light chain consisting of the amino acid sequence ranging from the 1st D to the 214th C of SEQ ID NO: 10.

In another embodiment, the CHv62.21 MAb comprises the heavy chain consisting of the amino acid sequence ranging from the 1st E to the $453^{rd}$ K of SEQ ID NO: 9 and the light chain consisting of the amino acid sequence ranging from the 1st D to the 214th C of SEQ ID NO: 10.

In another embodiment, the CHv62.21 MAb comprises the heavy chain consisting of the amino acid sequence ranging from the 1st E to the $453^{rd}$ K of SEQ ID NO: 9 wherein the 1st E is modified to pyro-glutamate and the C-terminal residue $453^{rd}$ K is removed and the light chain consisting of the amino acid sequence ranging from the 1st D to the 214th C of SEQ ID NO: 10.

In another embodiment, the CHv62.21 MAb comprises the heavy chain consisting of the amino acid sequence ranging from the 1st E to the $453^{rd}$ K of SEQ ID NO: 9 wherein the C-terminal residue $453^{rd}$ K is removed and the light chain consisting of the amino acid sequence ranging from the 1st D to the 214th C of SEQ ID NO: 10.

In a further preferred embodiment of the invention, the FLT3 MAbs of the invention, and specifically, the MAb denoted CHv62.21 is modified with a non-natural amino acid ("nnAA") in the heavy chain. In a preferred embodiment, an amber codon is located at amino acid position 124 of SEQ ID NO: 11 for insertion of a nnAA denoted para-acetylphenylalanine (FIG. 3C). Modified CHv62.21 is denoted CHv62.21pAF for the purposes of this invention.

Accordingly, in a preferred embodiment of the invention, CHv62.21pAF comprises the following:

A heavy chain variable region consists of the amino acid sequence ranging from $1^{st}$ residue (E) to the $123^{th}$ residue (S) residue of SEQ ID NO: 11, and a light chain variable region consists of the amino acid sequence ranging from $1^{st}$ residue (D) to the $108^{th}$ residue (R) residue of SEQ ID NO: 10. The CDR1-3 (Kabat) of heavy chain variable region consists of the amino acid sequence ranging from 31-35, from 50-65, and from 95-102 of SEQ ID NO: 11 respectively, and the CDR1-3 (Kabat or Chothia) of the light chain variable region consists of the amino acid sequence ranging from 24-34, from 50-56, and from 89-97 of SEQ ID NO: 10 respectively (See, FIG. 3B, FIG. 3C and Table V).

A heavy chain consisting of the amino acid sequence ranging from $1^{st}$ residue (E) to the $453^{rd}$ residue (K) of SEQ ID NO: 11 with a nnAA of para-acetylphenylalanine inserted at residue 124 of SEQ ID NO: 11 and a light chain of CHv62.21 consisting of amino acid sequence ranging from $1^{st}$ residue (D) to the $214^{th}$ residue (C) of SEQ ID NO: 10. The sequences of which is set forth in FIGS. 2B and/or 2C and FIGS. 3B and/or 3C. In a preferred embodiment, CHv62.21pAF is conjugated to a cytotoxic agent.

In yet another embodiment, the FLT3 MAb of the invention is produced by the method of producing an antibody or antigen binding fragment comprising culturing a host cell to allow expression of antibody or antigen binding fragment, wherein the host cell is selected from the group consisting of the following (a) to (c):

(a) a host cell transfected with an expression vector comprising a polynucleotide comprising a base sequence encoding a heavy chain variable region consisting of the amino acid sequence ranging from the 1st E to the $123^{rd}$ S of SEQ ID NO: 11 and a polynucleotide comprising a base sequence encoding a light chain variable region comprising the amino acid sequence ranging from the 1st D to the 108th R SEQ ID NO: 10;

(b) a host cell transfected with an expression vector comprising a polynucleotide comprising a base sequence encoding a heavy chain variable region consisting of the amino acid sequence ranging from the 1st E to the $123^{rd}$ S of SEQ ID NO: 11 and an expression vector comprising a polynucleotide comprising a base sequence encoding a light chain variable region comprising the amino acid sequence ranging from the 1st D to the 108th R SEQ ID NO: 10; and (c) a host cell transfected with an expression vector comprising a polynucleotide comprising a base sequence encoding a heavy chain variable region consisting of the amino acid sequence ranging from the 1st E to the $123^{rd}$ S of SEQ ID NO: 11 and a host cell transfected with an expression vector comprising a polynucleotide comprising a base sequence encoding a light chain variable region comprising the amino acid sequence ranging from the 1st D to the 108th R of SEQ ID NO: 10.

In yet another embodiment, the FLT3 MAb of the invention is produced by the method of producing an antibody comprising culturing a host cell to allow expression of antibody, wherein the host cell is selected from the group consisting of the following (a) to (c):

(a) a host cell transformed with an expression vector comprising a polynucleotide comprising a base sequence encoding a heavy chain consisting of the amino acid sequence ranging from the 1st E to the $453^{rd}$ K of SEQ ID NO: 11 and a polynucleotide comprising a base sequence encoding a light chain consisting of the amino acid sequence ranging from the 1st D to the 214th C of SEQ ID NO: 10;

(b) a host cell transformed with an expression vector comprising a polynucleotide comprising a base sequence encoding a heavy chain consisting of the amino acid sequence ranging from the 1st E to the $453^{rd}$ K of SEQ ID NO: 11 and an expression vector comprising a polynucleotide comprising a base sequence encoding a light chain consisting of the amino acid sequence ranging from the 1st D to the 214th C of SEQ ID NO: 10; and (c) a host cell transformed with an expression vector comprising a polynucleotide comprising a base sequence encoding a heavy chain consisting of the amino acid sequence ranging from the 1st E to the 453rd K of SEQ ID NO: 11 and a host cell transformed with an expression vector comprising a polynucleotide comprising a base sequence encoding a light chain consisting of the amino acid sequence ranging from the 1st D to the 214th C of SEQ ID NO: 10;

In yet another embodiment, the FLT3 MAb of the invention is produced by the method of producing an antibody comprising culturing a host cell to allow expression of antibody, wherein the host cell is selected from the group consisting of the following (a) to (d):

(a) a host cell transformed with an expression vector comprising a polynucleotide comprising a base sequence encoding a heavy chain consisting of the amino acid sequence ranging from the 1st E to the $453^{rd}$ K of SEQ ID NO: 11 and a polynucleotide comprising a base sequence encoding a light chain consisting of the amino acid sequence ranging from the 1st D to the 214th C of SEQ ID NO: 10;

(b) a host cell transformed with an expression vector comprising a polynucleotide comprising a base sequence encoding a heavy chain consisting of the amino acid sequence ranging from the 1st E to the $453^{rd}$ K of SEQ ID NO: 11 and an expression vector comprising a polynucleotide comprising a base sequence encoding a light chain consisting of the amino acid sequence ranging from the 1st D to the 214th C of SEQ ID NO: 10;

(c) a host cell transformed with an expression vector comprising a polynucleotide comprising a base sequence encoding a heavy chain consisting of the amino acid sequence ranging from the 1st E to the 453rd K of SEQ ID NO: 11 and a host cell transformed with an expression vector comprising a polynucleotide comprising a base sequence encoding a light chain consisting of the amino acid sequence ranging from the 1st D to the 214th C of SEQ ID NO: 10; and (d) a host cell transformed with an expression vector comprising a polynucleotide comprising a base sequence encoding a heavy chain consisting of the amino acid sequence ranging from the $1^{st}$ E to the $452^{rd}$ G of SEQ ID NO: 11 wherein the $1^{st}$ E is modified to pyroglutamate and the light chain consisting of the amino acid sequence ranging from the $1^{st}$ D to the $214^{th}$ C of SEQ ID NO: 10.

In another embodiment, the heavy chain variable region of CHv62.21pAF MAb is selected from the group consisting of an amino acid sequence ranging from residue 1 (E) to residue 123 (S) of SEQ ID NO: 11 and an amino acid sequence ranging from residue 1 (E) to residue 123 (S) of SEQ ID NO: 11 wherein the N-terminal residue 1 (E) is converted to pyroglutamic acid.

In another embodiment, the heavy chain of CHv62.21pAF MAb is selected from the group consisting of an amino acid sequence ranging from residue 1 (E) to residue 453 (K) of SEQ ID NO: 11, an amino acid sequence ranging from residue 1 (E) to residue 453 (K) of SEQ ID NO: 11 wherein the N-terminal residue 1 (E) is converted to pyroglutamic acid, an amino acid sequence ranging from residue 1 (E) to residue 453 (K) of SEQ ID NO: 11 wherein the C-terminal residue 453 (K) is removed, and an amino acid sequence ranging from residue 1 (E) to residue 453 (K) of SEQ ID NO: 11 wherein the N-terminal residue 1 (E) is converted to pyroglutamic acid and the C-terminal residue 453 (K) is removed.

In another embodiment, the CHv62.21pAF MAb or antigen-binding fragment thereof is a recombinantly-produced mixture of proteins obtained by expression in a host cell, wherein the heavy chain variable region of the antibody or antigen-binding fragment thereof is selected from the group consisting of an amino acid sequence ranging from residue 1 (E) to residue 123 (S) of SEQ ID NO: 11 and an amino acid sequence residue 1 (E) to residue 123 (S) of SEQ ID NO: 11 wherein the N-terminal residue 1 (E) is converted to pyroglutamic acid.

In another embodiment, the CHv62.21pAF MAb is a recombinantly-produced mixture of proteins obtained by expression in a host cell, wherein the heavy chain is selected from the group consisting of an amino acid sequence ranging from residue 1 (E) to residue 453 (K) of SEQ ID NO: 11, an amino acid sequence ranging from residue 1 (E) to residue 453 (K) of SEQ ID NO: 11 wherein the N-terminal residue 1 (E) is converted to pyroglutamic acid, an amino acid sequence ranging from residue 1 (E) to residue 453 (K) of SEQ ID NO: 11 wherein the C-terminal residue 453 (K) is removed, and an amino acid sequence ranging from residue 1 (E) to residue 453 (K) of SEQ ID NO: 11 wherein the N-terminal residue 1 (E) is converted to pyroglutamic acid and the C-terminal residue 453 (K) is removed.

In another embodiment, the CHv62.21pAF MAb comprises the heavy chain consisting of the amino acid sequence ranging from the 1st E to the $453^{rd}$ K of SEQ ID NO: 11 and the light chain consisting of the amino acid sequence ranging from the 1st D to the 214th C of SEQ ID NO: 10.

In another embodiment, the CHv62.21pAF MAb comprises the heavy chain consisting of the amino acid sequence ranging from the 1st E to the 453$^{rd}$ K of SEQ ID NO: 11 wherein the 1st E is modified to pyro-glutamate and the light chain consisting of the amino acid sequence ranging from the 1st D to the 214th C of SEQ ID NO: 10.

In another embodiment, the CHv62.21pAF MAb comprises the heavy chain consisting of the amino acid sequence ranging from the 1st E to the 453$^{rd}$ K of SEQ ID NO: 11 wherein the 1st E is modified to pyro-glutamate and the C-terminal residue 453$^{rd}$ K is removed and the light chain consisting of the amino acid sequence ranging from the 1st D to the 214th C of SEQ ID NO: 10.

In another embodiment, the CHv62.21pAF MAb comprises the heavy chain consisting of the amino acid sequence ranging from the 1st E to the 453$^{rd}$ K of SEQ ID NO: 11 wherein the C-terminal residue 453$^{rd}$ K is removed and the light chain consisting of the amino acid sequence ranging from the 1st D to the 214th C of SEQ ID NO: 10.

The Chinese Hamster Ovary (CHO) cell producing the antibody designated CHv62.21pAF was sent (via Federal Express) to the American Type Culture Collection (ATCC), P.O. Box 1549, Manassas, Va. 20108 on 9 Dec. 2014 and assigned Accession number PTA-121836.

III.) Antibody-Drug Conjugates Generally

In another aspect, the invention provides antibody-drug conjugates (ADCs), comprising an antibody conjugated to a therapeutic agent. The therapeutic agent maybe a cytotoxic agent, a cytostatic agent, a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the ADCs. In one aspect, an ADC comprises any of the above FLT3 MAbs covalently attached or attached via oxime bond to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ZEVALIN® (ibritumomab tiuxetan, Biogen/Idec) which is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69).

Also, MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001).

Additionally, Anti-human FLT3 antibodies have been assessed earlier as potential therapeutics for myeloid leukemia. For example, IMC-EB10, an antibody against FLT3 was developed by Imclone. This antibody is a ligand blocker which inhibits FLT3 mediated activation of downstream kinases (MAPK, Akt and StatS). The antibody also inhibits proliferation of leukemic cells in vitro; and is known to act via antibody dependent cellular toxicity (ADCC). EB10 has caused prolonged survival of the leukemic xenografts when treated alone and in combination with methotrexate (See, WO2009/155015 and US2011/0008355). This antibody was also evaluated in human clinical trials (NCT00887926), but terminated due to lack of efficacy. See also, EB10 conjugated to MMAF was developed by ImClone (See, Proc Amer Assoc Cancer Res, Volume 46, 2005).

It is known in the art that agonistic antibodies developed against FLT3 can enhance the proliferation and/differentiation of primitive hematpoietic cells. (See, WO 95/27062)

In addition to biologics, numerous small molecule inhibitors have been developed and tested in human clinical trials. Most of these inhibitors target FLT3 and other kinases and thus are not specific to FLT3 kinase itself. In most cases, these inhibitors target FLT3-ITD and possibly FLT-TKD. Accordingly, none are available to target wild type FLT3 alone. The small molecule inhibitors that are known to have entered human clinical trials are:

Midostaurin or PKC-412 (Novartis), Quizartinib or AC220 (Ambit), Nexavar (Onyx/Bayer), AZD1152 or Barasertib (Astrazeneca), Crenolinib (Arog), Plexxicon (Daichii Sankyo), and ASP2215 (Astellas). Generally, most human clinical trials are still ongoing. In most cases, thrombocytopenia, neutropenia, anemia have been observed as side effects.

In addition, Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others.

Additionally, MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors.

Finally, the auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784).

The CD30 MAb conjugated to MMAE is now commercially available as ADCETRIS (Seattle Genetics, Bothell, Wash.). ADCETRIS (brentuximab vedotin) is a CD-30 directed antibody drug conjugate consisting of three components: 1) the chimeric IgG1 antibody denoted cAC10, specific for human CD30, 2) the microtubule disrupting agent MMAE, and 3) a protease-cleavable linker that covalently attaches MMAE to caC10. See, ADCENTRIS prescribing information.

Further, therapeutic agents including but not limited to chemotherapeutic agents useful in the generation of ADCs are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

III(A). Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2$OR)(U.S. Pat. No. 4,331,598); C-14-hydroxymethyl or acyloxymethyl ($CH_2$OH or $CH_2$OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

ADCs containing maytansinoids, methods of making same, and their therapeutic use are disclosed, for example, in U.S. Pat. Nos. 5,208,020; 5,416,064; 6,441,163 and European Patent EP 0 425 235 B 1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA. 1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

III(B). Auristatins and Dolastatins

In some embodiments, the ADC comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schrüder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

III(C). Calicheamicin

In other embodiments, the ADC comprises an antibody of the invention conjugated to one or more calicheamicin molecules. The calicheamicin families of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

III(D). Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 (published Oct. 28, 1993).

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{88}$, $Sm^{53}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

IV.) Antibody-Drug Conjugate Compounds which Bind FLT3

The present invention provides, inter alia, antibody-drug conjugate compounds for targeted delivery of therapeutic agents. The inventors have made the discovery that the antibody-drug conjugate compounds have potent cytotoxic and/or cytostatic activity against cells expressing FLT3.

Such antibody drug conjugates do not block binding of FL to FLT3, such that FL can signal through FLT3 even when antibody is bound. Such antibodies demonstrate cytotoxic activity that is not reduced in the presence of FL (where an anti-FLT3 antibody drug conjugate that does block FL binding to FLT3 exhibits reduced cytoxicity in the presence of FL. In preferred embodiments, the anti-FLT3 drug conjugates described herein do not substantially inhibit binding of FL to FLT3.

The antibody-drug conjugate compounds comprise an Antibody unit covalently linked to at least one Drug unit. The Drug units can be covalently linked directly to the Antibody unit or via a Linker unit (-LU-).

In some embodiments, the antibody drug conjugate compound has the following formula:

L-(LU-D)$_p$     (I)

or a pharmaceutically acceptable salt or solvate thereof; wherein:

L is the Antibody unit, e.g., FLT3 MAb of the present invention, such as CHv62.21 or CHv62.21pAF, and
(LU-D) is a Linker unit-Drug unit moiety, wherein:
LU- is a Linker unit, and
-D is a drug unit having cytostatic or cytotoxic activity against a target cell; and
p ranges from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, p is an integer. In other embodiments p is measured as an average drug to antibody ratio and can be an integer or a non-integer.

In some embodiments, the antibody drug conjugate compound has the following formula:

L-(A$_a$-W$_w$-Y$_y$-D)$_p$     (II)

or a pharmaceutically acceptable salt or solvate thereof, wherein:

L is the Antibody unit, e.g., FLT3 MAb, such as CHv62.21 or CHv62.21pAF; and
-A$_a$-W$_w$-Y$_y$- is a Linker unit (LU), wherein:
-A- is a Stretcher unit,
a is 0 or 1 or 2 or 3,
each —W— is independently an Amino Acid unit,
w is an integer ranging from 0 to 12,
—Y— is a self-immolative spacer unit,
y is 0, 1 or 2;

-D is a drug units having cytostatic or cytotoxic activity against the target cell; and p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined. In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise FLT3 MAbs of the invention as the Antibody unit, a drug, and optionally a linker that joins the drug and the binding agent. In a preferred embodiment, the Antibody is FLT3 MAb comprising heavy and light chain variable regions of an antibody designated CHv62.21 described above. In a more preferred embodiment, the Antibody is FLT3 MAb comprising heavy and light chain of an antibody designated CHv62.21pAF described above (See, Formula (I)).

A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the FLT3 MAb under appropriate conditions.

V.) Linker Units

Typically, the antibody-drug conjugate compounds comprise a Linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. The linker can also be cleaved by a cleaving agent that is present in the extracellular environment (e.g. in the vicinity to the cellular membrane or tissue space). The linker can be, e.g., a peptidyl linker that is cleaved by an extracellular peptidase or protease enzyme, including, but not limited to, a cathepsin family enzymes or matrix metalloproteinases). In some embodiments, the peptidyl linker is at least two amino acids long or at least three amino acids long. In a preferred embodiment, the peptidyl linker contains at least one aminooxy acid unit (Ambrx, Inc., La Jolla, Calif.). Cleaving agents can include those agents known in the art (see, e.g., Dubowchik and Walker, 1999, *Pharm. Therapeutics* 83:67-123 and U.S. Pat. No. 6,214,345). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., an oxime, hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm.* Therapeutics 83:67-123; Neville et al., 1989, *Biol. Chem.* 264:14653-14661.) Such linkers are relatively stable under neutral pH conditions, such as those in the blood, but are unstable or less stable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions known in the art. (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.). The linker can also be cleaved under reducing conditions found intra-cellularly (or extra-cellularly). For example, in a preferred embodiment, the specific linker N—O bond may be formally reduced and broken to result in a cleavage of the linker.

In yet other embodiments, the linker unit is not cleavable and the drug is released by antibody degradation. (See PCT Publication No. WO2012/166560 (Ambrx, Inc.) incorporated by reference herein in its entirety and for all purposes).

In other, non-mutually exclusive embodiments, the linker promotes cellular internalization as known in the art.

A variety of exemplary linkers that can be used with the present compositions and methods are described in WO 2004/010957, U.S. Publication No. 2006/0074008, U.S. Publication No. 20050238649, and U.S. Publication No. 2006/0024317 (each of which is incorporated by reference herein in its entirety and for all purposes).

In a preferred embodiment, the LU of the present invention is denoted AGL and is commonly known as 2-(aminooxy)acetic acid or $C_2H_5NO_3$.

VI.) The Stretcher Unit

The Stretcher unit (A), when present, is capable of linking an Antibody unit to an Amino Acid unit (—W—), if present, to a Spacer unit (—Y—), if present; or to a Drug unit (-D). Useful functional groups that can be present on a FLT3 MAb (e.g. CHv62.21 or CHv62.21pAF), either naturally or via chemical manipulation include, but are not limited to, keto, aldehyde, sulfhydryl, amino, hydroxyl, the anomeric hydroxyl group of a carbohydrate, and carboxyl. Suitable functional groups are keto, aldehyde, sulfhydryl, and amino. In one example, the keto group is on a non-natural amino acid (nnAA) incorporated into the Mab of the invention. In a further example, the aldehyde group is on a nnAA incorporated into the Mab of the invention. In another example, sulfhydryl groups can be generated by reduction of the intramolecular disulfide bonds of a FLT3 MAb. In another embodiment, sulfhydryl groups can be generated by reaction of an amino group of a lysine moiety of a FLT3 MAb with 2-iminothiolane (Traut's reagent) or other sulfhydryl generating reagents. In certain embodiments, the FLT3 MAb is a recombinant antibody and is engineered to carry one or more lysines. In certain other embodiments, the recombinant FLT3 MAb is engineered to carry additional sulfhydryl groups, e.g., additional cysteines.

In one embodiment, the Stretcher unit forms an oxime bond with a keto group of the Antibody unit. The keto group is present on a nnAA incorporated in the MAb.

It is to be understood from all the exemplary embodiments that even where not denoted expressly, from 1 to 20 drug moieties can be linked to an Antibody (p=1-20).

The Amino Acid Unit

The Amino Acid unit (—W—), when present, links the Stretcher unit to the Spacer unit if the Spacer unit is present, links the Stretcher unit to the Drug moiety if the Spacer unit is absent, and links the Antibody unit to the Drug unit if the Stretcher unit and Spacer unit are absent.

Ww- can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

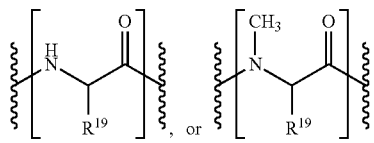

wherein R19 includes but is not limited to hydrogen, methyl, isopropyl, isobutyl, sec-butyl, benzyl, p-hydroxybenzyl, —CH2OH, —CH(OH)CH3, —CH2CH2SCH3, —CH2CONH2, —CH2COOH, —CH2CH2CONH2, —CH2CH2COOH, —(CH2)3NHC(=NH)NH2, —(CH2)3NH2, —(CH2)3NHCOCH3, —(CH2)3NHCHO, —(CH2)4NHC(=NH)NH2, —(CH2)4NH2, —(CH2)4NHCOCH3, —$(CH_2)_4$NHCHO, —$(CH_2)_3$NHCONH$_2$, —$(CH_2)_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl. For further reference, see (US2014/0072586 & WO2012/047724, which are fully incorporated by reference herein).

In certain embodiments, the Amino Acid unit can comprise natural amino acids. In other embodiments, the Amino Acid unit can comprise non-natural amino acids.

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline.

VII.) The Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent. Spacer units are of two general types: non self-immolative or self-immolative. Examples of possible spacers of the invention are known in the art. See, Toki et al., 2002, J. Org. Chem. 67:1866-1872 and Nature Biotechnology 21(7):778-784).

Other examples of self-immolative spacers include, but are not limited to, aromatic compounds that are electronically similar to the PAB group such as 2-aminoimidazol-5-methanol derivatives (Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury et al., 1984, J. Med. Chem. 27:1447) are also examples of self-immolative spacers.

VIII.) The Drug Unit

The Drug Unit (D) can be any therapeutic agent. For example, the Drug Unit may be a moiety that is cytotoxic, cytostatic or immunomodulatory (e.g., immunosuppressive) or chemotherapeutic agent. D is a Drug unit (moiety) having an atom that can form a bond with the Spacer unit (if present), with the Amino Acid unit (if present), with the Stretcher unit (if present) or with the Antibody unit. In some embodiments, the Drug unit D has a nitrogen atom that can form a bond with the Spacer unit (if used). As used herein, the terms "Drug unit" and "Drug moiety" are synonymous and used interchangeably.

Useful classes of cytotoxic or immunomodulatory agents include, for example, antitubulin agents, DNA minor groove binders, DNA replication inhibitors, and alkylating agents. In some embodiments, the Drug is an auristatin, such as auristatin E (also known in the art as a derivative of dolastatin-10) or a derivative thereof. Other typical auristatins include AFP, MMAF, and MMAE. The synthesis and structure of exemplary auristatins are described in U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

In some embodiments, the Drug Unit is a calicheamicin, camptothecin, a maytansinoid, or an anthracycline. In some embodiments the drug is a taxane, a topoisomerase inhibitor, a vinca alkaloid, or the like.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, and vinca alkaloids. Other cytotoxic agents include, for example, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug is an anti-tubulin agent. Examples of anti-tubulin agents include, auristatins, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent is a dolastatin. In certain embodiments, the cytotoxic or cytostatic agent is of the auristatin class.

In a further embodiment, Drug Units are novel dolaproine-dolaisoleuine peptide analogs. Thus, provided herein are compounds of Formula (I):

wherein
$R^1$ and $R^2$ are each independently —H or alkyl;
X is —O—, —$NR^z$—, —S—, or is absent;
  wherein $R^z$ is —H or alkyl;
$R^3$ is a group of the formula:

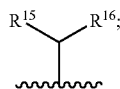

wherein $R^{15}$ and $R^{16}$ are each independently —H, —OH, —$NH_2$, —SH, —$N_3$, alkyl, alkenyl, alkynyl, -alkyl-OH, -alkyl-$NH_2$, -alkyl-SH, or -alkyl-$N_3$;
$R^4$ is a group of the formula:

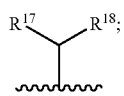

wherein $R^{17}$ and $R^{18}$ are each independently —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$
$R^5$ is sec-butyl or isobutyl;
$R^6$ is —H or alkyl;
$R^7$ and $R^8$ are each independently —H, alkyl, —$CO_2R^a$, $CONR^bR^c$, substituted or unsubstituted phenyl, or substituted or unsubstituted heterocyclic ring;
  wherein $R^a$ is —H or alkyl;
  $R^b$ and $R^c$ are each independently H or alkyl;
$R^9$ is —H or alkyl; or $R^9$ is taken together with $R^4$ and the atoms to which they are attached to form a substituted or unsubstituted heterocycloalkyl ring;
$R^{10}$ is —H or alkyl;
$R^{11}$ is —H or alkyl;
$R^{12}$ is —H or alkyl;
$R^{13}$ is —H or alkyl; and
$R^{14}$ is —H, —OH or alkyl;
provided that when X is absent and $R^5$, $R^{16}$, $R^{17}$ and $R^{18}$ are each methyl, then $R^8$ is not substituted or unsubstituted phenyl, or substituted or unsubstituted heterocyclic ring;
or a pharmaceutically acceptable salt thereof.

In some embodiments, $R^1$ and $R^2$ are each independently —H or alkyl, for example $C_{1-6}$ alkyl In some embodiments, $R^1$ and $R^2$ are each independently —H or methyl. In some

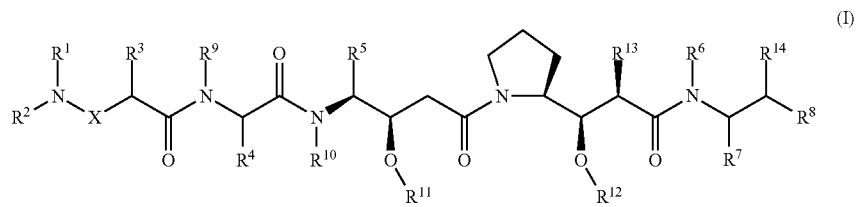

(I)

embodiments, $R^1$ and $R^2$ are each independently alkyl. In some embodiments, $R^1$ and $R^2$ are both methyl. In some embodiments, $R^1$ and $R^2$ are both —H.

In some embodiments, X is absent. In other embodiments, X is —O—. In some embodiments, $R^1$ and $R^2$ are each independently alkyl, and X is absent. In some embodiments, $R^1$ and $R^2$ are both methyl, and X is absent. In other embodiments, $R^1$ and $R^2$ are both —H, and X is —O—. In some embodiments, X is —$NR^z$—, wherein $R^z$ is —H or alkyl. In some embodiments, $R^z$ is —H. In some embodiments, X is $R^z$ is alkyl, for example $C_{1-6}$alkyl or methyl.

In certain embodiments, $R^3$ is

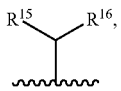

wherein $R^{15}$ and $R^{16}$ are each independently —H, —OH, —$NH_2$, —SH, —$N_3$, alkyl, alkenyl, alkynyl, -alkyl-OH, -alkyl-$NH_2$, -alkyl-SH, or -alkyl-$N_3$. In still other embodiments, $R^{15}$ and $R^{16}$ are each independently —H, alkyl, —$(CH_2)_{0-6}C\equiv CH$, —$(CH_2)_{0-6}CH=CH_2$, —$(CH_2)_{0-6}OH$, —$(CH_2)_{0-6}NH_2$, —$(CH_2)_{0-6}SH$, or —$(CH_2)_{0-6}N_3$. In some embodiments, $R^{15}$ and $R^{16}$ are each independently —H, —OH, or alkyl. In some embodiments, $R^{15}$ and $R^{16}$ are each independently —H, —OH, or methyl. In some embodiments, $R^5$ is —OH and $R^{16}$ is hydrogen. In some embodiments, $R^5$ is —OH and $R^{16}$ is methyl.

In certain embodiments, $R^3$ is in the R stereochemical configuration relative to the remainder of the molecule. In other embodiments, $R^3$ is in the S stereochemical configuration relative to the remainder of the molecule. In certain embodiments, the $R^3$ group itself contains one or more chiral centers, and those stereocenters are each independently in the R or S configuration.

In certain embodiments, $R^4$ is

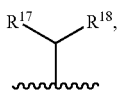

wherein $R^{17}$ and $R^{18}$ are each independently —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$. In other embodiments, $R^4$ is

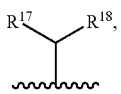

wherein $R^{17}$ is —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$, and $R^{18}$ is —H, —OH, —$NH_2$, —SH, —$N_3$, —$CO_2H$, alkenyl, alkynyl, -alkyl-OH, -alkyl-$NH_2$, -alkyl-SH, -alkyl-$N_3$ or -alkyl-$CO_2H$. In still other embodiments, $R^{17}$ and $R^{18}$ are each independently —H, alkyl, —$(CH_2)_{0-6}C\equiv CH$, —$(CH_2)_{0-6}CH=CH_2$, —$(CH_2)_{0-6}OH$, —$(CH_2)_{0-6}NH_2$, —$(CH_2)_{0-6}SH$, or —$(CH_2)_{0-6}N_3$. In some embodiments, $R^{17}$ and $R^{18}$ are each independently —H, —OH, —$NH_2$, —SH, —$N_3$, alkyl, -alkyl-$NH_2$, or -alkyl-$N_3$. In some embodiments, $R^{17}$ and $R^{18}$ are each independently —H, —OH, —$NH_2$, —SH, —$N_3$, —$CO_2H$, methyl, —$CH_2NH_2$, or —$CH_2N_3$.

In certain embodiments, $R^4$ is taken together with $R^9$ and the atoms to which they are attached to form a substituted or unsubstituted heterocycloalkyl ring. In certain embodiments, $R^4$ is taken together with $R^9$ and the atoms to which they are attached to form a 5- to 7-member heterocycloalkyl ring, which may be unsubstituted or substituted with one or more groups selected from —OH, —$NH_2$, —SH, and —$N_3$. In certain embodiments, the heterocycloalkyl ring is a pyrrolidine ring, which may be unsubstituted or substituted with one or more groups selected from —OH, —$NH_2$, —SH, and —$N_3$.

In certain embodiments, $R^4$ is in the R stereochemical configuration relative to the remainder of the molecule. In other embodiments, $R^4$ is in the S stereochemical configuration relative to the remainder of the molecule. In certain embodiments, the $R^4$ group itself contains one or more chiral centers, and those stereocenters are each independently in the R or S configuration.

In certain embodiments, $R^5$ is sec-butyl. In other embodiments, $R^5$ is isobutyl. In certain embodiments, $R^5$ is in the R stereochemical configuration relative to the remainder of the molecule. In other embodiments, $R^5$ is in the S stereochemical configuration relative to the remainder of the molecule. In some embodiments, the chiral center within the $R^5$ group is in the R configuration, and in other embodiments, that center is in the S configuration.

In certain embodiments, $R^6$ is —H. In other embodiments, $R^6$ is alkyl, for example $C_{1-8}$alkyl, $C_{1-4}$alkyl, methyl, or ethyl.

In some embodiments, $R^7$ and $R^8$ are each independently is —H, alkyl, —$CO_2R^a$ or —$CONR^bR^c$; wherein $R^a$ is —H or alkyl, for example $C_{1-6}$alkyl or methyl; and $R^b$ and $R^c$ are each independently —H or alkyl, for example $C_{1-6}$alkyl or methyl.

In certain embodiments, $R^7$ and $R^8$ are each independently is substituted or unsubstituted phenyl or substituted or unsubstituted heterocyclic ring, wherein the phenyl or heterocyclic ring may be substituted with one or more groups selected from halo, oxo, hydroxy, amino, alkyl, and alkoxy. In certain other embodiments, $R^7$ is unsubstituted 3- to 8-member heterocyclic ring. In certain other embodiments, $R^7$ is substituted 3- to 8-member heterocyclic ring. In certain other embodiments, $R^8$ is phenyl which is optionally substituted with halo.

In certain embodiments, $R^7$ is in the R stereochemical configuration relative to the remainder of the molecule. In other embodiments, $R^7$ is in the S stereochemical configuration relative to the remainder of the molecule.

In certain embodiments, $R^8$ is in the R stereochemical configuration relative to the remainder of the molecule. In other embodiments, $R^8$ is in the S stereochemical configuration relative to the remainder of the molecule.

In some embodiments, $R^7$ is —$CO_2R^a$—$CONR^bR^c$; tetrazolyl or thiazolyl, wherein $R^a$ is —H or alkyl, for example $C_{1-6}$alkyl or methyl; and $R^b$ and $R^c$ are each independently —H or alkyl, for example $C_{1-6}$alkyl or methyl; and $R^8$ is phenyl which is optionally substituted with halo.

In some embodiments, $R^9$ is —H. In other embodiments, $R^9$ is alkyl, for example $C_{1-8}$alkyl, $C_{1-4}$alkyl, methyl, or ethyl. In some embodiments, $R^9$ is —H or methyl. In some embodiments, $R^9$ is methyl.

In some embodiments, $R^{10}$ is —H. In other embodiments, $R^{10}$ is alkyl, for example $C_{1-8}$alkyl, $C_{1-4}$alkyl, methyl, or ethyl. In some embodiments, $R^{10}$ is —H or methyl. In some embodiments, $R^{10}$ is methyl.

In some embodiments, $R^{11}$ is —H. In other embodiments, $R^{11}$ is alkyl, for example $C_{1-8}$alkyl, $C_{1-4}$alkyl, methyl, or ethyl. In some embodiments, $R^{11}$ is —H or methyl. In some embodiments, $R^{11}$ is methyl.

In some embodiments, $R^{12}$ is —H. In other embodiments, $R^{12}$ is alkyl, for example $C_{1-8}$alkyl, $C_{1-4}$alkyl, methyl, or ethyl. In some embodiments, $R^{12}$ is —H or methyl. In some embodiments, $R^{12}$ is methyl.

In some embodiments, $R^{13}$ is —H. In other embodiments, $R^{13}$ is alkyl, for example $C_{1-8}$alkyl, $C_{1-4}$alkyl, methyl, or ethyl. In some embodiments, $R^{13}$ is —H or methyl. In some embodiments, $R^{13}$ is methyl.

In some embodiments, $R^{14}$ is —H. In some embodiments, $R^{14}$ is alkyl, for example $C_{1-6}$alkyl, methyl, or ethyl. In some embodiments, $R^{14}$ is —OH.

In certain embodiments, $R^{14}$ is in the R stereochemical configuration relative to the remainder of the molecule. In other embodiments, $R^{14}$ is in the S stereochemical configuration relative to the remainder of the molecule.

In some embodiments, $R^7$ is —$CO_2R^a$, wherein $R^a$ is —H or alkyl, for example $C_{1-6}$alkyl or methyl; $R^8$ is phenyl; and $R^{14}$ is —H. In some embodiments, $R^7$ is —$CONR^bR^c$, wherein $R^b$ and $R^c$ are each independently —H or alkyl, for example $C_{1-6}$alkyl or methyl; $R^8$ is phenyl; and $R^{14}$ is —H. In some embodiments, $R^7$ is alkyl, for example $C_{1-6}$alkyl or methyl; $R^8$ is phenyl; and $R^{14}$ is —OH. In some embodiments, $R^7$ is methyl, $R^8$ is phenyl, and $R^{14}$ is —OH. In some embodiments, $R^7$ and $R^{14}$ are both —H, and $R^8$ is pyridinyl, piperidinyl, unsubstituted phenyl, or phenyl substituted with halo, for example fluoro, chloro, or bromo. In some embodiments, $R^7$ is —$CO_2R^a$, wherein $R^a$ is —H or alkyl, for example $C_{1-6}$alkyl or methyl; $R^8$ is —H or alkyl, for example $C_{1-6}$alkyl or methyl; and $R^{14}$ is alkyl, for example $C_{1-6}$alkyl, methyl, or ethyl. In some embodiments, $R^7$ is —$CO_2R^a$, wherein $R^a$ is —H or alkyl, for example $C_{1-6}$alkyl or methyl; $R^8$ is —H or alkyl, for example $C_{1-6}$alkyl or methyl; and $R^{14}$ is —OH.

In certain embodiments,
$R^1$ and $R^2$ are each independently —H or $C_{1-6}$alkyl;
X is —O— or is absent;
$R^3$ is

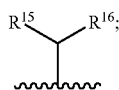

wherein $R^{15}$ and $R^{16}$ are each independently —H, —OH, or $C_{1-6}$alkyl;
$R^4$ is

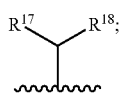

wherein $R^{17}$ is —OH, —$NH_2$, —SH, —$N_3$, —$CO_2H$, —$C_{1-6}$alkyl-$NH_2$, alkynyl, alkenyl, or —$C_{1-6}$alkyl-$N_3$; and $R^{18}$ is —H or $C_{1-6}$alkyl;
$R^5$ is sec-butyl;
$R^6$ is —H;
$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;
$R^8$ is —H, $C_{1-6}$alkyl, substituted or unsubstituted phenyl or substituted or unsubstituted heterocyclic ring;
$R^9$ is —H;
$R^{10}$, $R^{11}$, $R^{12}$, and $R^{13}$ are each independently $C_{1-6}$alkyl; and
$R^{14}$ is —H, $C_{1-6}$alkyl or —OH.

In certain embodiments,
$R^1$ and $R^2$ are each independently —H or methyl;
X is —O— or is absent;
$R^3$ is

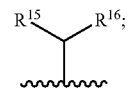

wherein $R^{15}$ and $R^{16}$ are each independently —H, —OH, or methyl;
$R^4$ is

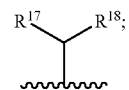

wherein $R^{17}$ is —OH, —$NH_2$, —SH, —$N_3$, —$CO_2H$, aminomethyl, alkynyl, alkenyl, or azidomethyl; and $R^{18}$ is —H or methyl;
$R^5$ is sec-butyl;
$R^6$ is —H;
$R^7$ is —H, methyl, —$CO_2R^a$, or —$CONR^bR^c$; wherein $R^a$ is —H or methyl; and $R^b$ and $R^c$ are each —H or methyl;
$R^8$ is —H, methyl, ethyl, pyridinyl, piperidinyl, unsubstituted phenyl, phenyl substituted with halo;
$R^9$ is —H;
$R^{10}$, $R^{11}$, $R^{12}$, and $R^{13}$ are each methyl; and
$R^{14}$ is —H, methyl or —OH.

In certain embodiments,
$R^1$ and $R^2$ are each independently —H or $C_{1-6}$alkyl;
X is absent;
$R^3$ is

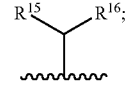

wherein $R^{15}$ and $R^{16}$ are each independently —H, —OH, or $C_{1-6}$alkyl;
$R^4$ is

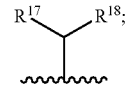

wherein $R^{17}$ is —$N_3$, and $R^{18}$ is —H or methyl;
$R^5$ is sec-butyl;
$R^6$ is —H;
$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;
$R^8$ is —H, $C_{1-6}$alkyl, substituted or unsubstituted phenyl or substituted or unsubstituted heterocyclic ring;
$R^9$ is —H;
$R^{10}$, $R^{11}$, $R^{12}$, and $R^{13}$ are each independently $C_{1-6}$alkyl; and
$R^{14}$ is —H, $C_{1-6}$alkyl or —OH.
In certain embodiments,
$R^1$ and $R^2$ are each independently —H or $C_{1-6}$alkyl;
X is —O—;
$R^3$ is

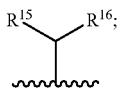

wherein $R^{15}$ and $R^{16}$ are each independently —H, —OH, or $C_{\text{-}6}$alkyl;
$R^4$ is

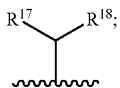

wherein $R^{17}$ is —$N_3$, and $R^1$ is —H or methyl;
$R^5$ is sec-butyl;
$R^6$ is —H;
$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;
$R^8$ is —H, $C_{1-6}$alkyl, substituted or unsubstituted phenyl or substituted or unsubstituted heterocyclic ring;
$R^9$ is —H;
$R^{10}$, $R^{11}$, $R^{12}$, and $R^{13}$ are each independently $C_{1-6}$alkyl; and
$R^{14}$ is —H, $C_{1-6}$alkyl or —OH.
In some embodiments of Formula (I), wherein,
$R^1$ and $R^2$ are each methyl;
X is absent;
$R^3$ is a group of the formula:

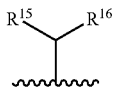

wherein $R^{15}$ and $R^{16}$ are each methyl;
$R^4$ is a group of the formula:

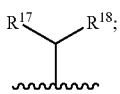

wherein $R^{17}$ is —$N_3$, —$NH_2$, —OH, —SH, and $R^{18}$ is —H or methyl;
$R^5$ is sec-butyl;
$R^6$ is —H;
$R^7$ is —$CO_2R^a$ or $CONR^bR^c$,
wherein $R^a$ is —H or $C_{1-6}$alkyl;
$R^b$ and $R^c$ are each independently H or $C_{1-6}$alkyl;
$R^8$ is phenyl;
$R^9$ is —H;
$R^{10}$, $R^{11}$, $R^{12}$, and $R^{13}$ are each independently methyl; and
$R^{14}$ is —H.
In some embodiments of Formula (I), wherein,
$R^1$ and $R^2$ are each —H;
X is —O—;
$R^3$ is a group of the formula:

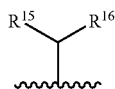

wherein $R^{15}$ and $R^{16}$ are each methyl;
$R^4$ is a group of the formula:

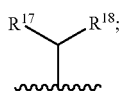

wherein $R^{17}$ is —$N_3$, and $R^{18}$ is —H or methyl;
$R^5$ is sec-butyl;
$R^6$ is —H;
$R^7$ is —$CO_2R^a$ or $CONR^bR^c$,
wherein $R^a$ is —H or $C_{1-6}$alkyl;
$R^b$ and $R^c$ are each independently H or $C_{1-6}$alkyl;
$R^8$ is phenyl;
$R^9$ is —H;
$R^{10}$, $R^{11}$, $R^{12}$, and $R^{13}$ are each independently methyl; and
$R^{14}$ is —H.
It is to be understood that any variable group definition provided herein can be used in combination with any other variable group definition provided herein, such that all possible combinations and permutations of variable groups provided herein, where chemically feasible, are contemplated.

In certain embodiments, compounds of Formula (I) are selected from the group consisting of:
(S)-methyl 2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoate;
(S)-methyl 2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoate;
(S)-2-(dimethylamino)-N—((S)-3-hydroxy-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-3-methylbutanamide;
(2S,3R)-2-((S)-2-(dimethylamino)-3-methylbutanamido)-3-hydroxy-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;
(2S)-2-(dimethylamino)-N-((2S)-3-hydroxy-1-(((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)(methyl)amino)-1-oxopropan-2-yl)-3-methylbutanamide;

(2S,3R)-2-((S)-2-(dimethylamino)-3-methylbutanamido)-3-hydroxy-N-((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)-N-methylbutanamide;

(S)-methyl 2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-3-amino-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)—N—((S)-3-amino-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-2-(dimethylamino)-3-methylbutanamide;

(S)-methyl 2-((2R,3R)-3-((S)-1-((3R,4S,5S)-4-((S)-3-azido-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((S)-2-(aminooxy)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N,3-dimethylbutanamide;

((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanoyl)-L-phenylalanine;

((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanoyl)-L-phenylalanine;

(S)-2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((2S,3R)-2-(dimethylamino)-3-hydroxybutanamido)-N,3-dimethylbutanamide;

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-hydroxypropanamido)-N,3-dimethylbutanamide;

(S)-methyl 2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoic acid;

(S)-methyl 2-((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-azido-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(2S,3S)-3-azido-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-azido-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2- methyl-3-oxopropyl)pyrrolidin-1-yl)-3-methoxy-5-methyl-1-oxoheptan-4-yl)-N-methylbutanamide;

(2S,3S)-3-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(S)-4-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(S)-4-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((S)-2-((S)-2-(dimethylamino)-3-methylbutanamido)-N-methylpent-4-ynamido)-3-methoxy-5-methylheptanoyl)pyrrolidin-2-yl)-3-methoxy-2-methylpropanoyl)-L-phenylalaninate;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-2-((S)-2-(dimethylamino)-3-methylbutanamido)-N-methylbutanamide;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;

(2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-valinate;

methyl ((2R,3R)-3-((S)-1-((3R,4S,5S)-4-((S)-6-amino-2-((S)-2-(dimethylamino)-3-methylbutanamido)-N-methylhexanamido)-3-methoxy-5-methylheptanoyl)pyrrolidin-2-yl)-3-methoxy-2-methylpropanoyl)-L-phenylalaninate;

methyl ((2R,3R)-3-((S)-1-((3R,4S,5S)-4-((2S,4S)-4-azido-1-(dimethyl-L-valyl)-N-methylpyrrolidine-2-carboxamido)-3-methoxy-5-methylheptanoyl)pyrrolidin-2-yl)-3-methoxy-2-methylpropanoyl)-L-phenylalaninate;

(S)-3-((S)-2-(dimethylamino)-3-methylbutanamido)-4-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-4-oxobutanoic acid;

(2S,3R)-2-((S)-2-(dimethylamino)-3-methylbutanamido)-3-hydroxy-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

methyl ((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)-L-serinate;

methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-isoleucinate;

(2S,3S)-3-amino-N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((S)-3-azido-N-methyl-2-((S)-3-methyl-2-(methylamino)butanamido)propanamido)-3-methoxy-5-methylheptanoyl)pyrrolidin-2-yl)-3-methoxy-2-methylpropanoyl)-L-phenylalaninate;

methyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide;

((2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N-methyl-2-((S)-3-methyl-2-(methylamino)butanamido)butanamide;

tert-butyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate;

((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalanine;

tert-butyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide;

(2S,3S)-3-azido-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5- methyl-1-oxoheptan-4-yl)-N-methyl-2-((S)-3-methyl-2-(methylamino)butanamido)butanamide;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;

tert-butyl ((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide; and (2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;

and pharmaceutically acceptable salts thereof.

Also provided herein are pharmaceutically acceptable salts of the compounds of Formula (I), preferably of those described above and the specific compounds exemplified herein, pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al. "Pharmaceutical Salts," *J. Pharm. Sci.* 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include acid addition salts such as sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, α-hydroxybutyrates, glycolates, tartrates, and mandelates, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

For treatment purposes, pharmaceutical compositions comprising compounds described herein may further comprise one or more pharmaceutically-acceptable excipients. A pharmaceutically-acceptable excipient is a substance that is non-toxic and otherwise biologically suitable for administration to a subject. Such excipients facilitate formulation and administration of a compound described herein and are compatible with the active ingredient. Examples of pharmaceutically-acceptable excipients include stabilizers, lubricants, surfactants, diluents, anti-oxidants, binders, coloring agents, emulsifiers, or taste-modifying agents. In preferred embodiments, pharmaceutical compositions are sterile compositions.

The pharmaceutical compositions described herein may be formulated as solutions, emulsions, suspensions, or dispersions in suitable pharmaceutical solvents or carriers, or as pills, tablets, lozenges, suppositories, powders for reconstitution, or capsules along with solid carriers according to conventional methods known in the art for preparation of various dosage forms. For topical applications, the compounds described herein are preferably formulated as creams or ointments or a similar vehicle suitable for topical administration. The pharmaceutical compositions and compounds described herein may be administered in the inventive methods by a suitable route of delivery, e.g., oral, nasal, parenteral, rectal, topical, ocular, or by inhalation.

The term "treat" or "treating" as used herein is intended to refer to administration of a compound described herein to a subject for the purpose of creating a therapeutic benefit. Treating includes reversing, ameliorating, alleviating, inhibiting the progress of, or lessening the severity of, a disease, disorder, or condition, or one or more symptoms of cancer. The term "subject" refers to a mammalian patient in need of such treatment, such as a human.

In treatment methods provided herein, "an effective amount" means an amount or dose sufficient to generally bring about the desired therapeutic benefit in subjects needing such treatment. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a subject, e.g. a human, which enhances or aids in the therapeutic effect of a second pharmaceutical agent. Effective amounts, including therapeutically effective amounts, or doses of the compounds described herein may be ascertained by routine methods, such as modeling, dose escalation or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose for the antibody drug conjugates disclosed herein is in the range of about 1 ug to 2 mg of active compound per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

The compounds described herein may be used in pharmaceutical compositions or methods in combination with additional active ingredients in the treatment of cancer. The additional active ingredients may be administered separately from a compound described herein or may be included with a compound described herein in a pharmaceutical composition provided herein. For example, additional active ingredients are those that are known or discovered to be effective in treating cancer, including those active against another target associated with cancer, such as but not limited to, Velcade, Rituximab, Methotrexate, Herceptin, Vincristine, Prednisone, Irinotecan, or the like, or a combination thereof. Such a combination may serve to increase efficacy, decrease one or more side effects, or decrease the required dose of a disclosed compound.

Compounds of Formula (I) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Each of the reactions depicted in Scheme A is preferably run at a temperature from about room temperature to the reflux temperature of the organic solvent used. Unless otherwise specified, the variables are as defined above in reference to Formula (I).

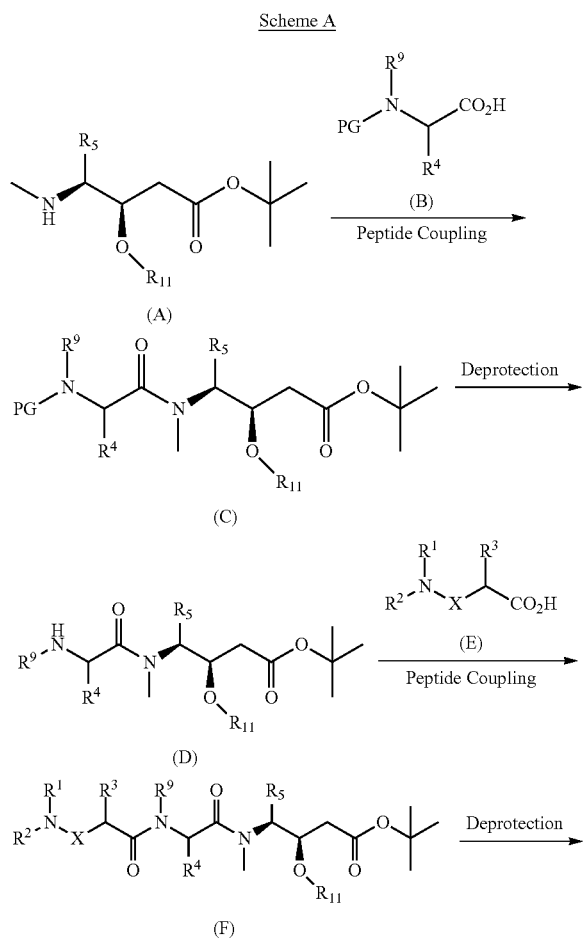

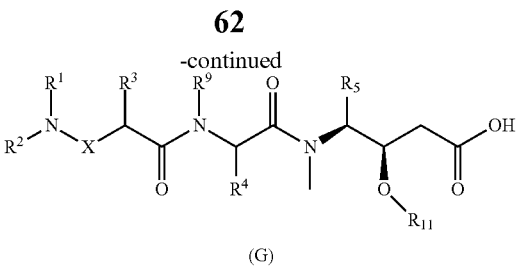

Referring to Scheme A, the preparation of compounds of Formula (I) begins with a protected acid form of dolaisoleuine (Dil) labeled (A) (see Pettit et al. (1994) *J. Org. Chem.* 59:1796-1800). Compound (A) is depicted with a tert-butyl ester protecting group, but one of skill in the art may select an appropriate replacement. Coupling with a nitrogen-protected valine or isoleucine derivative (B), where PG is a suitable amino protecting group such as a Boc (t-butoxycarbonyl) or fluorenylmethyloxycarbonyl (Fmoc) group, is effected under standard peptide coupling conditions. For example, reactions are run in the presence of diethyl cyanophosphonate (DEPC), PyBrOP, PyBOP, BOP, diisopropylcarbodiimide (DIC), dicyclohexylcarbodiimide (DCC), 1-(3-dimethylaminopropyl)-3-ethylcarbodiimide hydrochloride (EDCI), 1-hydroxybenzotriazole (HOBt), 1-hydroxy-7-aza-benzotriazole (HOAt), HBTU (O-benzotriazol-1-yl-N,N,N',N'-tetramethyluronium hexafluorophosphate), HATU (O-(7-azabenzotriazol-1-yl)-1,1,3,3-tetramethyluronium hexafluorophosphate), and the like, or a combination thereof. Reactions are typically run in the presence of a tertiary amine base, such as diisopropylethylamine. Suitable solvents include dichloromethane, N,N-dimethylformamide (DMF), dimethyl sulfoxide (DMSO), ethyl acetate and the like. The amino protecting group on resultant dipeptide (C) is removed by deprotection under suitable conditions. For example, where PG is a Boc group, compound (C) is treated with trifluoroacetic acid to form free amine (D). Where PG is an Fmoc group, compound (C) is treated with piperidine or diethylamine to yield compound (D). Compound (D) is then coupled to amino acid derivative (E), in protected form if necessary, under peptide coupling conditions as described above, to generate tripeptide (F). Treatment with acid removes the carboxy protecting group to provide free acid (G).

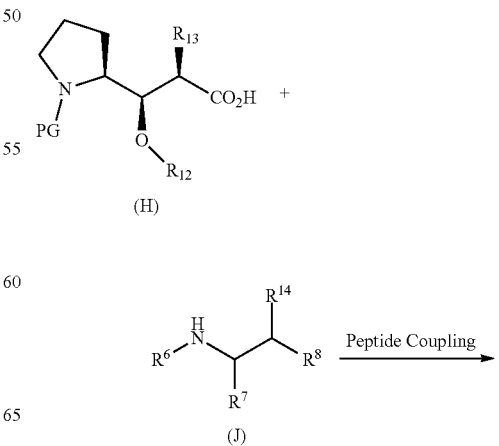

-continued

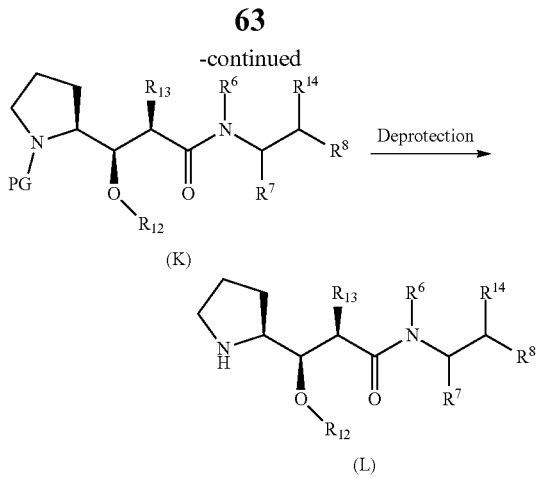

Referring to Scheme B, the amino-protected dolaproine (Dap) designated as (H) (see Pettit et al. (1994) *J. Org. Chem.* 59:6287-6295) is coupled with amine (J) (which is prepared using methods known to one in the art) under peptide coupling conditions as described above. Resulting dipeptide (K) is deprotected as discussed for Scheme A to provide compound (L).

Scheme C

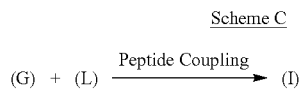

Referring to Scheme C, acid (G) and amine (L) are coupled under peptide coupling conditions as discussed above to provide compounds of Formula (I). Where the result of the reaction is a protected form of Formula (I), suitable deprotection conditions are employed to give the target compound.

Also provided herein is a pharmaceutical composition comprising an effective amount of at least one compound of Formula (I), or a pharmaceutically acceptable salt thereof, and a pharmaceutically acceptable excipient.

Also provided herein is a method of treating a subject suffering from or diagnosed with cancer, comprising administering to a subject in need of such treatment an effective amount of at least one compound of Formula (I), or a pharmaceutically acceptable salt thereof.

Also provided herein is use of at least one compound of Formula (I), or a pharmaceutically acceptable salt thereof, for treatment of cancer in a subject in need of such treatment.

Also provided herein is use of at least one compound of Formula (I), or a pharmaceutically acceptable salt thereof, in the manufacture of a medicament for treatment of cancer in a subject in need of such treatment.

Also provided herein is a kit containing at least one compound of Formula (I), or a pharmaceutically acceptable salt thereof, for use in treating cancer in a subject in need of such treatment, and instructions for use.

Also provided herein is an article of manufacture comprising at least one compound of Formula (I), or a pharmaceutically acceptable salt thereof, for use in treating cancer in a subject in need of such treatment.

Also provided herein are antibody drug conjugates (ADCs) wherein a compound of Formula (I) is conjugated to an Antibody.

Exemplary ADCs utilizing Formula (I) have the following structures wherein "L" or "mAb-s-" represents a FLT3 MAb designated CHv62.21 set forth herein.

Additionally, further exemplary ADCs utilizing Formula (I) have the following structures wherein "L" or "mAb-s-" represents a FLT3 MAb designated CHv62.21pAF set forth herein.

In a preferred embodiment, compounds of Formula (I) comprise Drug Units comprising the compound denoted (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide.

In a preferred embodiment, compounds of Formula (I) comprise Drug Units comprising the compound set forth below as Formula (II):

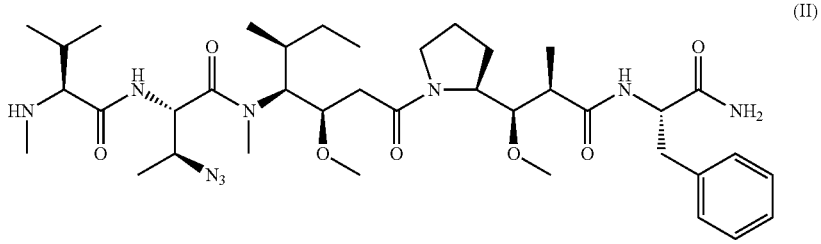 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@@H](NC)C(C)C)[C@H](C)N=[N+]=[N-]]

(II)

IX.) Drug Loading

Drug loading is represented by p and is the average number of Drug moieties per antibody in a molecule. Drug loading may range from 1 to 20 drug moieties (D) per antibody. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay. The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachements (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

X.) Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that a Antibody Drug conjugate is useful in the treatment of cancers.

Cell viability can be measured by determining in a cell the uptake of a dye such as neutral red, trypan blue, or ALA-MAR™ blue (see, e.g., Page et al., 1993, *Intl. J. Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Natl. Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures.

For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

In vivo, the effect of a FLT3 therapeutic composition can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

In one embodiment, the pharmaceutical composition of the present invention may comprise more than one species of ADC of the invention due to modification of CHv62.21 MAb or CHv62.21pAF MAb. For example, the present invention includes a pharmaceutical composition comprising the ADC of the invention, wherein the CHv62.21 MAb is an antibody lacking heavy chain C-terminal lysine, an antibody having N-terminal post-translational modification, an antibody lacking heavy chain C-terminal lysine and having N-terminal post-translational modification, and/or an antibody having heavy chain C-terminal lysine and not having N-terminal post-translational modification.

For example, a pharmaceutical composition of the present invention includes an pharmaceutical composition comprising two or more species of the ADC of the invention, wherein CHv62.21 MAb of the ADC is selected from the group of the following 1) to 4):

1) CHv62.21 MAb comprising a heavy chain consisting of the amino acid sequence ranging from residue 1 (E) to residue 453 (K) of SEQ ID NO: 9 and a light chain consisting of the amino acid sequence ranging from residue 1 (D) to residue 214 (C) of SEQ ID NO: 10;
2) CHv62.21 MAb comprising a heavy chain consisting of the amino acid sequence ranging from residue 1 (E) to residue 453 (K) of SEQ ID NO: 9 wherein the N-terminal residue 1 (E) is converted to pyroglutamic acid and a light chain consisting of the amino acid sequence ranging from residue 1 (D) to residue 214 (C) of SEQ ID NO: 10;
3) CHv62.21 MAb comprising a heavy chain consisting of the amino acid sequence ranging from residue 1 (Q) to residue 453 (K) of SEQ ID NO: 9 wherein the C-terminal residue 453 (K) is removed and a light chain consisting of the amino acid sequence ranging from residue 1 (D) to residue 214 (C) of SEQ ID NO: 10; and
4) CHv62.21 MAb comprising a heavy chain consisting of the amino acid sequence ranging from residue 1 (E) to residue 453 (K) of SEQ ID NO: 9 wherein the N-terminal residue 1 (E) is converted to pyroglutamic acid and the C-terminal residue 453 (K) is removed and a light chain consisting of the amino acid sequence ranging from residue 1 (D) to residue 214 (C) of SEQ ID NO: 10.

In one embodiment, a pharmaceutical composition of the present invention includes an pharmaceutical composition comprising CHv62.21 MAb comprising a heavy chain consisting of the amino acid sequence ranging from residue 1 (E) to residue 453 (K) of SEQ ID NO: 9 and a light chain consisting of the amino acid sequence ranging from residue 1 (D) to residue 214 (C) of SEQ ID NO: 10 and CHv62.21 MAb comprising a heavy chain consisting of the amino acid sequence ranging from residue 1 (Q) to residue 453 (K) of SEQ ID NO: 9 wherein the C-terminal residue 453 (K) is removed and a light chain consisting of the amino acid sequence ranging from residue 1 (D) to residue 214 (C) of SEQ ID NO: 10.

In one embodiment, a pharmaceutical composition of the present invention includes an pharmaceutical composition comprising CHv62.21 MAb comprising a heavy chain consisting of the amino acid sequence ranging from residue 1 (Q) to residue 453 (K) of SEQ ID NO: 9 wherein the C-terminal residue 453 (K) is removed and a light chain consisting of the amino acid sequence ranging from residue 1 (D) to residue 214 (C) of SEQ ID NO: 10 and CHv62.21 MAb comprising a heavy chain consisting of the amino acid sequence ranging from residue 1 (E) to residue 453 (K) of SEQ ID NO: 9 wherein the N-terminal residue 1 (E) is converted to pyroglutamic acid and the C-terminal residue 453 (K) is removed and a light chain consisting of the amino acid sequence ranging from residue 1 (D) to residue 214 (C) of SEQ ID NO: 10.

In a preferred embodiment, a pharmaceutical composition of the present invention includes an pharmaceutical composition comprising two or more species of the ADC of the invention, wherein CHv62.21pAF MAb of the ADC is selected from the group of the following 1) to 4):

1) CHv62.21pAF MAb comprising a heavy chain consisting of the amino acid sequence ranging from residue 1 (E) to residue 453 (K) of SEQ ID NO: 11 and a light chain consisting of the amino acid sequence ranging from residue 1 (D) to residue 214 (C) of SEQ ID NO: 10;
2) CHv62.21pAF MAb comprising a heavy chain consisting of the amino acid sequence ranging from residue 1 (E) to residue 453 (K) of SEQ ID NO: 11 wherein the N-terminal residue 1 (E) is converted to pyroglutamic acid and a light chain consisting of the amino acid sequence ranging from residue 1 (D) to residue 214 (C) of SEQ ID NO: 10;
3) CHv62.21pAF MAb comprising a heavy chain consisting of the amino acid sequence ranging from residue 1 (Q) to residue 453 (K) of SEQ ID NO: 11 wherein the C-terminal residue 443 (T) is removed and a light chain consisting of the amino acid sequence ranging from residue 1 (D) to residue 214 (C) of SEQ ID NO: 10; and
4) CHv62.21pAF MAb comprising a heavy chain consisting of the amino acid sequence ranging from residue 1 (E) to residue 453 (K) of SEQ ID NO: 11 wherein the N-terminal residue 1 (E) is converted to pyroglutamic acid and the C-terminal residue 443 (T) is removed and a light chain consisting of the amino acid sequence ranging from residue 1 (D) to residue 214 (C) of SEQ ID NO: 10.

In one embodiment, a pharmaceutical composition of the present invention includes an pharmaceutical composition comprising CHv62.21pAF MAb comprising a heavy chain consisting of the amino acid sequence ranging from residue 1 (E) to residue 453 (K) of SEQ ID NO: 11 and a light chain consisting of the amino acid sequence ranging from residue 1 (D) to residue 214 (C) of SEQ ID NO: 10 and CHv62.21pAF MAb comprising a heavy chain consisting of the amino acid sequence ranging from residue 1 (Q) to residue 453 (K) of SEQ ID NO: 11 wherein the C-terminal residue 443 (T) is removed and a light chain consisting of the amino acid sequence ranging from residue 1 (D) to residue 214 (C) of SEQ ID NO: 10.

In one embodiment, a pharmaceutical composition of the present invention includes an pharmaceutical composition comprising CHv62.21pAF MAb comprising a heavy chain consisting of the amino acid sequence ranging from residue 1 (Q) to residue 453 (K) of SEQ ID NO: 11 wherein the C-terminal residue 443 (T) is removed and a light chain consisting of the amino acid sequence ranging from residue 1 (D) to residue 214 (C) of SEQ ID NO: 10 and CHv62.21pAF MAb comprising a heavy chain consisting of the amino acid sequence ranging from residue 1 (E) to residue 453 (K) of SEQ ID NO: 11 wherein the N-terminal residue 1 (E) is converted to pyroglutamic acid and the C-terminal residue 443 (T) is removed and a light chain consisting of the amino acid sequence ranging from residue 1 (D) to residue 214 (C) of SEQ ID NO: 10.

XI.) Treatment of Cancer(s) Expressing FLT3

The identification of FLT3 as a protein that is normally expressed in a restricted set of tissues or cells, but which is also expressed in cancers such as those listed in Table I, opens a number of therapeutic approaches to the treatment of such cancers.

Of note, targeted antitumor therapies have been useful even when the targeted protein is expressed on normal tissues or cells, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensible, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a FLT3 protein are useful for patients suffering from a cancer that expresses FLT3 (such as, for example, those cancers set forth in Table I). These therapeutic approaches generally fall into three classes. The first class modulates FLT3 function as it relates to tumor cell growth leading to inhibition or retardation of tumor cell growth or inducing its killing. The second class comprises various methods for inhibiting the binding or association of a FLT3 protein with its binding partner or with other proteins. The third class comprises a variety of methods for inhibiting the transcription of a FLT3 gene or translation of FLT3 mRNA.

Accordingly, Cancer patients can be evaluated for the presence and level of FLT3 expression, preferably using immunohistochemical assessments of tumor tissue, quantitative FLT3 imaging, or other techniques that reliably indicate the presence and degree of FLT3 expression. Immunohistochemical analysis of tumor biopsies or surgical specimens is preferred for this purpose, if applicable. Methods for immunohistochemical analysis of tumor tissues are well known in the art.

XIII.) FLT3 as a Target for Antibody-Based Therapy

FLT3 is an attractive target for antibody-based therapeutic strategies. A number of antibody strategies are known in the art for targeting both extracellular and intracellular molecules (see, e.g., complement and ADCC mediated killing as well as the use of intrabodies). Because FLT3 is expressed by cancer cells of various lineages relative to corresponding normal cells, systemic administration of FLT3-immunoreactive compositions are prepared that exhibit excellent sensitivity without toxic, non-specific and/or non-target effects caused by binding of the immunoreactive composition to non-target organs and tissues. Antibodies specifically reactive with domains of FLT3 are useful to treat FLT3-expressing cancers systemically, preferably as antibody drug conjugates (i.e. ADCs) wherein the conjugate is with a toxin or therapeutic agent.

Those skilled in the art understand that antibodies can be used to specifically target and bind immunogenic molecules such as an immunogenic region of a FLT3 sequence shown in FIG. 1. In addition, skilled artisans understand that it is routine to conjugate antibodies to cytotoxic agents (see, e.g., Slevers et al. Blood 93:11 3678-3684 (Jun. 1, 1999)). When cytotoxic and/or therapeutic agents are delivered directly to cells, such as by conjugating them to antibodies specific for a molecule expressed by that cell (e.g. FLT3), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an mammal having a tumor a biologically effective amount of a conjugate comprising a selected cytotoxic and/or therapeutic agent linked to a targeting agent (e.g. a FLT3 MAb, preferably CHv62.21 or CHv62.21pAF) that binds to an antigen (e.g. FLT3) expressed, accessible to binding or localized on the cell surfaces. A typical embodiment is a method of delivering a cytotoxic and/or therapeutic agent to a cell expressing FLT3, comprising conjugating the cytotoxic agent to an antibody that immunospecifically binds to a FLT3 epitope, and, exposing the cell to the antibody drug conjugate (ADC). Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using FLT3 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals) respectively, while others involve co-administration of antibodies and other therapeutic agents, such as Herceptin™ (trastuzu MAb) with paclitaxel (Genentech, Inc.). In a preferred embodiment, the antibodies will be conjugated a cytotoxic agent, supra, preferably an aurastatin derivative designated MMAE (Seattle Genetics).

Although FLT3 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

FLT3 monoclonal antibodies that treat the cancers set forth in Table I include those that initiate a potent immune response against the tumor or those that are directly cytotoxic. In this regard, FLT3 monoclonal antibodies (MAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, FLT3 MAbs that exert a direct biological effect on tumor growth are useful to treat cancers that express FLT3. Mechanisms by which directly cytotoxic MAbs act include: inhibition of cell growth, modulation of cellular differentiation, modulation of tumor angiogenesis factor profiles, and the induction of apoptosis. The mechanism(s) by which a particular FLT3 MAb exerts an anti-tumor effect is evaluated using any number of in vitro assays that evaluate cell death such as ADCC, complement-mediated cell lysis, and so forth, as is generally known in the art.

Accordingly, preferred monoclonal antibodies used in the therapeutic methods of the invention are those that are either fully human and that bind specifically to the target FLT3 antigen with high affinity.

XIV.) FLT3 ADC Cocktails

Therapeutic methods of the invention contemplate the administration of single FLT3 ADCs as well as combinations, or cocktails, of different MAbs (i.e. FLT3 MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, FLT3 MAbs can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the FLT3 MAbs are administered in conjugated form.

FLT3 ADC formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the FLT3 ADC preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of FLT3 expression in the patient, the extent of circulating shed FLT3 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of FLT3 in a given sample (e.g. the levels of circulating FLT3 antigen and/or FLT3 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide FLT3 ADCs, which inhibit or retard the growth of tumor cells expressing FLT3. A further object of this invention is to provide methods to inhibit angiogenesis and other biological functions and thereby reduce tumor growth in mammals, preferably humans, using such FLT3 ADCs, and in particular using such FLT3 ADCs combined with other drugs or immunologically active treatments.

XV.) Combination Therapy

In one embodiment, there is synergy when tumors, including human tumors, are treated with FLT3 ADCs in conjunction with chemotherapeutic agents or radiation or combinations thereof. In other words, the inhibition of tumor growth by a FLT3 ADC is enhanced more than expected when combined with chemotherapeutic agents or radiation or combinations thereof. Synergy may be shown, for example, by greater inhibition of tumor growth with combined treatment than would be expected from a treatment of only FLT3 ADC or the additive effect of treatment with a FLT3 ADC and a chemotherapeutic agent or radiation. Preferably, synergy is demonstrated by remission of the cancer where remission is not expected from treatment either from a FLT3 ADC or with treatment using an additive combination of a FLT3 ADC and a chemotherapeutic agent or radiation.

The method for inhibiting growth of tumor cells using a FLT3 ADC and a combination of chemotherapy or radiation or both comprises administering the FLT3 ADC before, during, or after commencing chemotherapy or radiation therapy, as well as any combination thereof (i.e. before and during, before and after, during and after, or before, during, and after commencing the chemotherapy and/or radiation therapy). For example, the FLT3 ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the FLT3 ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a FLT3 ADC, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

XVI.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an antibody that is or can be detectably labeled. Kits can comprise a container comprising a Drug Unit. The kit can include all or part of the amino acid sequences in FIGS. 2A, 2B and/or 2C, or FIGS. 3A, 3B and/or 3C or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer of a tissue set forth in Table I.

The terms "kit" and "article of manufacture" can be used as synonyms.

In another embodiment of the invention, an article(s) of manufacture containing compositions, such as antibody(s), or antibody drug conjugates (ADCs) e.g., materials useful for the diagnosis, prognosis, prophylaxis and/or treatment of cancers of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In another embodiment a container comprises an antibody, binding fragment thereof or specific binding protein for use in evaluating protein expression of FLT3 in cells and tissues, or for relevant laboratory, prognostic, diagnostic, prophylactic and therapeutic purposes; indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding FLT3 or an antibody drug conjugate specifically binding to FLT3.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Further embodiments of the disclosure herein include the embodiments described in the following clauses:

Clause 1 is an embodiment of an antibody, wherein the antibody comprises a CDRH1 having the amino acid sequence of SEQ ID NO:23, a CDRH2 having the amino acid sequence of SEQ ID NO:29, a CDRH3 having the amino acid sequence of SEQ ID NO:32, a CDRL1 having the amino acid sequence of SEQ ID NO: 14, a CDRL2 having the amino acid sequence of SEQ ID NO: 17, and a CDRL3 having the amino acid sequence of SEQ ID NO:20. In an alternative embodiment, the antibody comprises the CDRs as determined by the Chothia method as shown in Table V. In another alternative embodiment, the antibody comprises the CDRs as determined by the Contact method as shown in Table V.

Clause 2 is a further embodiment, wherein the antibody is an antibody according to clause 1, and wherein the antibody comprises a heavy chain variable region consisting of the amino acid sequence ranging from $1^{st}$ E to the $123^{rd}$ S of SEQ ID NO: 11 and comprises a light chain variable region consisting of the amino acid sequence ranging from $1^{st}$ D to the $108^{th}$ R of SEQ ID NO: 10.

Clause 3 is a further embodiment, wherein the antibody is an antibody according to any one of the preceding clauses, and wherein the antibody comprises a heavy chain variable region consisting of the amino acid sequence of the heavy chain variable region of an antibody produced by a Chinese Hamster Ovary (CHO) cell deposited under ATCC Accession No. PTA-121831 and comprises a light chain variable region consisting of the amino acid sequence of the light chain of an antibody produced by a Chinese Hamster Ovary (CHO) deposited under ATCC. Accession No. PTA-121831; or wherein the antibody comprises a heavy chain variable region consisting of the amino acid sequence of the heavy chain variable region of an antibody produced by a Chinese Hamster Ovary (CHO) cell deposited under ATCC Accession No. PTA-121836 and comprises a light chain variable region consisting of the amino acid sequence of the light chain of an antibody produced by a Chinese Hamster Ovary (CHO) deposited under ATCC. Accession No. PTA-121836.

Clause 4 is a further embodiment, wherein the antibody is an antibody according to any one of the preceding clauses, and wherein the antibody comprises an Fc region that is an IgG subtype.

Clause 5 is a further embodiment, wherein the antibody is an antibody according to the preceding clause, and wherein the Fc region comprises a substitution of a non-natural amino acid at amino acid position 124 of the heavy chain, and wherein the non-natural amino acid is para-acetylphenylalanine (pAF).

Clause 6 is a further embodiment, wherein the antibody is an antibody according to any one of the preceding clauses, and wherein the antibody comprises a heavy chain consisting of the amino acid sequence of amino acid numbers 1 to 452 of SEQ ID NO: 11 and comprises a light chain consisting of the amino acid sequence ranging from the $1^{st}$ D to the 214th SEQ ID NO: 10. In an alternative embodiment of Clause 6, the antibody is an antibody according to clause 1 or clause 2, wherein the antibody comprises a heavy chain consisting of the amino acid sequence of amino acid numbers 1 to 452 of SEQ ID NO: 11 and comprises a light chain consisting of the amino acid sequence ranging from the $1^{st}$ D to the 214th SEQ ID NO: 10.

Clause 7 is a further embodiment, wherein the antibody is an antibody according to any one of the preceding clauses, and wherein the antibody comprises a heavy chain consisting of the amino acid sequence ranging from $1^{st}$ E to the $453^{rd}$ K of SEQ ID NO: 11 and comprises a light chain consisting of the amino acid sequence ranging from $1^{st}$ D to the $214^{th}$ C of SEQ ID NO: 10. In an alternative embodiment of Clause 7, the antibody is an antibody according to clause 1 or clause 2, wherein the antibody comprises a heavy chain consisting of the amino acid sequence ranging from $1^{st}$ E to the $453^{rd}$ K of SEQ ID NO: 11 and comprises a light chain consisting of the amino acid sequence ranging from $1^{st}$ D to the $214^{th}$ C of SEQ ID NO: 10.

Clause 8 is a further embodiment, wherein the antibody is an antibody according to any of the preceding clauses, and wherein the antibody comprises a heavy chain consisting of the amino acid sequence of the heavy chain of an antibody produced by a Chinese Hamster Ovary (CHO) cell deposited under American Type Culture Collection (ATCC) Accession No. PTA-121831, and comprises a light chain consisting of the amino acid sequence of the light chain of an antibody produced by a Chinese Hamster Ovary (CHO) cell deposited under ATCC Accession No. PTA-121831. An alternative embodiment of clause 8 is an antibody according to clause 5, wherein the antibody comprises a heavy chain consisting of the amino acid sequence of the heavy chain of an antibody produced by a Chinese Hamster Ovary (CHO) cell deposited under American Type Culture Collection (ATCC) Accession No. PTA-121831, and comprises a light chain consisting of the amino acid sequence of the light chain of an antibody produced by a Chinese Hamster Ovary (CHO) cell deposited under ATCC Accession No. PTA-121831.

Clause 9 is a further embodiment, wherein the antibody is an antibody of any of the preceding clauses, and wherein the antibody comprises a heavy chain consisting of the amino acid sequence of the heavy chain of an antibody produced by a Chinese Hamster Ovary (CHO) cell deposited under ATCC. Accession No. PTA-121836, and comprises a light chain consisting of the amino acid sequence of the light chain of an antibody produced by a Chinese Hamster Ovary (CHO) deposited under ATCC. Accession No. PTA-121836. An alternative embodiment of clause 9 is an antibody of any one of clauses 1 to 5, wherein the antibody comprises a heavy chain consisting of the amino acid sequence of the heavy chain of an antibody produced by a Chinese Hamster Ovary (CHO) cell deposited under ATCC. Accession No. PTA-121836, and comprises a light chain consisting of the amino acid sequence of the light chain of an antibody produced by a Chinese Hamster Ovary (CHO) deposited under ATCC. Accession No. PTA-121836.

Clause 10 is a further embodiment wherein the antibody is an antibody according to any one of the preceding clauses, and wherein the $1^{st}$ E of the heavy chain variable region or the heavy chain is substituted with pyroglutamate.

Clause 11 is a further embodiment wherein the antibody is an antibody according to any of clauses 1-5, and wherein the antibody comprises a heavy chain consisting of the amino acid sequence ranging from the $1^{st}$ E to the $452^{rd}$ G of SEQ ID NO: 11, and wherein the $1^{st}$ E of the heavy chain variable region or the heavy chain is modified to pyroglutamate, and wherein the antibody comprises a light chain consisting of the amino acid sequence ranging from the $1^{st}$ D to the $214^{th}$ C of SEQ ID NO: 10. An alternative embodiment of clause 11 is an antibody of any one of clauses 1 to 6, wherein the antibody comprises a heavy chain consisting of the amino acid sequence ranging from the $1^{st}$ E to the $452^{rd}$ G of SEQ ID NO: 11, and wherein the $1^{st}$ E of the heavy chain variable region or the heavy chain is modified to pyroglutamate, and wherein the antibody comprises a light chain consisting of the amino acid sequence ranging from the $1^{st}$ D to the 214w C of SEQ ID NO: 10.

Clause 12 is a further embodiment that is an antigen binding fragment comprising the CDRs of the antibodies according to any one of the preceding clauses, and wherein the antigen-binding fragment binds FLT-3.

Clause 13 is a further embodiment which is the antigen-binding fragment according to the preceding clause, wherein the antigen-binding fragment is selected from the group consisting of Fab, Fab', F(ab')$_2$, Fv, scFv, isolated VH, and isolated VL.

Clause 14 is an antibody comprising the antigen-binding fragment according to clause 12 or clause 13.

Clause 15 is a further embodiment which is an antibody which has 80%, 85%, 90%, 91%, 92%, 93%, 94%, 95%, 96%, 97%, 98%, or 99% sequence identity to the antibody according to any of the preceding clauses 1 to 10 or 14, and wherein the antibody comprises the CDRs of the antibody according to any of the preceding clauses.

Clause 16 is a further embodiment which is an antibody according to clause 15 that binds FLT3 with the same affinity as the corresponding antibody of clause 15, and does not substantially inhibit FL binding to FLT3.

Clause 17 is a further embodiment which is one or more isolated nucleic acids encoding the antibody according to any one of clauses 1 to 10 or 14.

Clause 18 is a further embodiment which is one or more isolated nucleic acids encoding the antibody or fragments of clauses 12 or 13.

Clause 19 is a further embodiment of the nucleic acids of clause 17 or 18 which has 80%, 85%, 90%, 91%, 92%, 93%, 94%, 95%, 96%, 97%, 98%, or 99% sequence identity to the nucleic acids of the corresponding clauses.

Clause 20 is a further embodiment which is one or more expression vectors comprising the one or more isolated nucleic acids according to clause 17 or clause 18 or clause 19. In one embodiment of clause 20, there is one expression vector that expresses the heavy and light chain of an antibody of any of the preceding clauses. In a further embodiment, the expression vector of clause 20 comprises two promoters. In an alternative embodiment, the expression vector of clause 20 comprises one promoter. In a different embodiment of clause 20, there are two expression vectors, one of which expresses the heavy chain, and the other of which expresses the light chain. In a further embodiment, each expression vector of clause 20 comprises the same promoter. In a still further embodiment, each expression vector of clause 20 comprises a different promoter.

Clause 21 is a further embodiment which is a recombinant host cell comprising the one or more expression vectors according to the preceding clause, clause 20.

Clause 22 is a further embodiment which is an antibody produced by culturing the recombinant host cell of the preceding clause, clause 21.

Clause 23 is a further embodiment which is an antibody drug conjugate comprising the antibody of the preceding clause, clause 22, and a therapeutic agent.

Clause 24 is an embodiment that is an antibody drug conjugate that comprises an antibody that binds FLT3 and a therapeutic agent, wherein the antibody drug conjugate does not substantially inhibit the binding of FLT3 to FLT3 ligand (FL).

Clause 25 is a further embodiment that is the antibody drug conjugate of clause 23 or clause 24, further comprising a linker joining the antibody and the therapeutic agent.

Clause 26 is a further embodiment, which is an antibody drug conjugate of clause 25, wherein the linker is a non-cleavable linker.

Clause 27 is a further embodiment which is the antibody drug conjugate of clause 26, wherein the linker is 2-(aminooxy)acetic acid.

Clause 28 is a further embodiment which is the antibody drug conjugate of any one of clauses 23 to 27, wherein the therapeutic agent is a cytotoxic or cytostatic agent.

Clause 29 is a further embodiment which is the antibody drug conjugate of any one of clauses 23 to 28, wherein the therapeutic agent is (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide.

Clause 30 is a further embodiment which is an antibody drug conjugate, wherein the antibody drug conjugate is any one of clauses 23 to 29, and wherein the antibody drug conjugate has the following formula:

Antibody-(Linker-therapeutic agent)p, wherein the linker is 2-(aminooxy)acetic acid, and wherein the therapeutic agent is (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide and wherein p is selected from the group consisting of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.

Clause 31 is a further embodiment which is an antibody drug conjugate of clause 30, wherein p is selected from the group consisting of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.

Clause 32 is a further embodiment which is an antibody drug conjugate of clause 31, wherein p is selected from the group consisting of 1.5, 1.6, 1.7, 1.8, 1.9, 2, 2.1, 2.2, 2.3, 2.4, 2.5.

Clause 33 is a further embodiment which is an antibody drug conjugate of clause 32, wherein p is selected from the group consisting of 1.8, 1.9, and 2.

Clause 34 is a further embodiment that is a pharmaceutical composition, wherein the pharmaceutical composition comprises a therapeutically effective amount of the antibody drug conjugate of any of clauses 23 to 33.

Clause 35 is a further embodiment which is the pharmaceutical composition of clause 34, for use in therapy.

Clause 36 is a further embodiment that is a pharmaceutical composition, wherein the pharmaceutical composition is according to the preceding clause, clause 35, wherein the use in therapy is the treatment of cancer.

Clause 37 is a further embodiment that is a pharmaceutical composition, wherein the pharmaceutical composition is according to any one of clauses 34 to 36, in combination with one or more anti-neoplastic agents.

Clause 38 is a further embodiment that is a method of treating cancer in a subject, wherein the method of treating cancer in a subject comprises administering to said subject a therapeutically effective amount of an antibody drug conjugate according to any of claims 23 to 33, or a pharmaceutical composition thereof. Another embodiment of clause 37 is an embodiment that is a method of treating cancer in a subject, wherein the method of treating cancer in a subject comprises administering to said subject a therapeutically effective amount of a pharmaceutical composition according to any one of claims 33 to 37.

Clause 39 is a further embodiment that is a pharmaceutical composition according to any one of clauses 33 to 37, or the method according to clause 38, wherein the cancer comprises one or more cells that express FLT3 at an increased level as compared to a non-cancerous cell.

EXAMPLES

Various aspects of the invention are further described and illustrated by way of the several examples that follow, none of which is intended to limit the scope of the invention.

Example 1

The FLT3 Antigen

FLT3, Fms like tyrosine kinase 3 receptor, also known as Flk2 (fetal liver kinase 2), STK1 (stem cell tyrosine kinase 1) and CD135, is a member of the type III receptor tyrosine kinases (RTKs). Human FLT3 encodes an RTK of 993 amino acids in length, which comprises membrane-bound receptor with five immunoglobulin-like extracellular domains and two intracellular tyrosine kinase domains (TKD) linked by a kinase-insert domain (Stirewalt D L et al; Nat Rev Cancer; 650-665(2003). Human FLT3 gene (Gene ID No.: 2322 (National Center for Biotechnology Information)) is located on chromosome 13q12 and share 85% amino acid sequence homology with mouse FLT3 (Rosnet O et al; Oncogene 8:173-179 (1993). FLT3 is expressed in normal myeloid and lymphoid progenitor cells and by the leukemic cells of 70-90% of AML patients (Carow, C. E et al; Blood 87: 1089-1096 (1996); Rosnet O et al; Leukemia 10:238-248 (1996) and also in ALL. FLT3 is known to be involved in the proliferation, differentiation and apoptosis of hematopoietic cells. Many hematopoietic cells produce FLT3 ligand (FLT3L), which promotes receptor dimerization and activation, thus inducing signaling cascade via PI3kinase and MAPK pathways (Stirewalt D L et al; Nat Rev Cancer; 650-665(2003). Approximately, 30% of AML patients harbor FLT3 internal-tandem duplication (ITD) mutations that drive constitutive activation of the receptors and downstream signaling cascade, associated with poor disease outcome (Gunawardane R N et al; Mom Cancer Ther 12:438-447 (2013). For exemplary embodiments of the FLT3 antigen, see FIG. 1.

Example 2

Generation of FLT3 Monoclonal Antibodies (MAbs)

In one embodiment, therapeutic Monoclonal Antibodies ("MAbs") to FLT3 comprise those that react with epitopes specific for FLT3 that would bind to FLT3 expressed on cells. Immunogens for generation of such MAbs include those designed to encode or contain the extracellular domains or the entire FLT3 protein sequence, regions predicted to contain functional motifs, and regions of FLT3 predicted to be antigenic by computer analysis of the amino acid sequence. Immunogens include peptides, recombinant proteins and cells (which endogenously express FLT3 or that have been engineered to express FLT3).

MAbs to FLT3 were generated using VelocImmune® technology (Regeneron, Tarrytown, N.Y.) wherein genetically engineered mice make antibodies that have fully human variable regions and mouse constant regions. The MAb designated v62-1b21 (also known as AGS62.21) was generated after immunizing VelocImmune® mice with recombinant human FLT3 protein. The FLT3 MAb, v62-1b21 specifically binds to Flt3 protein and Flt3 expressing cells (recombinant and endogenous).

After selection, v62-1b21 (naturally produced by a hybridoma cell line) was converted to a CHO expressed fully human native antibody by combining the human variable sequences from the VelocImmune® antibody (See, Example 3—Expression of CHv62.21 using Recombinant DNA Methods) but with human constant regions incorporating a non-natural amino acid at position 124 on the heavy chain, according to the ReCODE technology developed by Ambrx (La Jolla, Calif.) (See, Example 4—Expression of Human CHv62.21pAF Using Recombinant DNA Methods).

DNA coding sequences for v62-1b21 was determined after isolating mRNA from the v62-1b21 producing hybridoma cells. Anti-Flt3, v62-1b21 heavy and light chain variable nucleic acid sequences were derived from the hybridoma cells using the following protocol. v62-1b21 secreting hybridoma cells were lysed with Trizol reagent (Life Technologies, Gibco BRL). Total RNA was purified and first strand cDNA was generated from total RNA with oligo (dT)12-18 priming using the Gibco-BRL Superscript Pre-amplification system. First strand cDNA was then amplified using human immunoglobulin variable heavy chain primers, and human immunoglobulin variable light chain primers. PCR products were sequenced and the variable heavy and light chain regions determined.

The nucleic acid and amino acid sequences of the variable heavy and light chain regions are listed in FIGS. 2A and/or 2B and FIGS. 3A and/or 3B. Alignment of CHv62.21 MAb to human Ig germline is set forth in FIG. 4A-4B.

Example 3

Expression of CHv62.21 Using Recombinant DNA Methods

To express CHv62.21 MAb recombinantly in transfected cells, v62.21 hybridoma MAb variable heavy and light chain sequences were cloned upstream of the human heavy chain IgG and human light chain IgK constant regions respectively. The complete CHv62.21 MAb human heavy chain and light chain cassettes were cloned downstream of the CMV promoter/enhancer in a cloning vector. The recombinant CHv62.21 MAb expressing construct was transfected into CHO cells for stable expression in the Lonza GS system (Lonza, Basel, Switzerland). The CHv62.21 MAb secreted from recombinant CHO cells was purified and evaluated for binding to cell surface FLT3 by flow cytometry. Results show that the recombinant CHv62.21 antibody expressed in CHO cells binds to FLT3 on the cell surface.

Results further show that the recombinantly expressed CHv62.21 expressed in CHO cells binds FLT3 similarly to the v62.21 purified from hybridoma. The CHv62.21 MAb secreted from recombinant cells is also evaluated for binding to FLT3 recombinant protein by ELISA. Binding of CHv62.21 to FLT3 protein is identical between MAb material derived from CHO and from hybridoma cells.

The Chinese Hamster Ovary (CHO) cell producing an antibody designated CHv62.21 was sent (via Federal Express) to the American Type Culture Collection (ATCC), P.O. Box 1549, Manassas, Va. 20108 on 9 Dec. 2014 and assigned Accession number PTA-121831.

The nucleic acid and amino acid sequences of the variable heavy and light chain regions are listed in FIGS. 2A and/or 2B and FIGS. 3A and/or 3B.

As a result of experimental analysis, using methods known in the art (e.g. protease digestion, LCMS analysis, etc.), amino acid modification(s) of the CHv62.21 MAb derived from CHO cells, showed that the deletion of lysine at the C terminal of the heavy chain occurs in most of purified CHv62.21 MAb and pyroglutamylation at the N terminal of the heavy chain and deletion of lysine at the C terminal of the heavy chain occur in a part of purified CHv62.21 MAb.

Example 4

Expression of Human CHv62.21pAF Using Recombinant DNA Methods

To express CHv62.21pAF recombinantly in transfected cells, v62-1b21 hybridoma MAb variable heavy and light chain sequences were cloned upstream of the human heavy chain IgG and human light chain IgK constant regions respectively. The complete CHv62.21 MAb human heavy chain and light chain cassettes were cloned downstream of the CMV promoter/enhancer in a cloning vector. The recombinant CHv62.21 MAb expressing construct was then transfected into CHO pAFsupl-4E2 cells (Ambrx, La Jolla, Calif.), which stably express the amber suppressor tRNA and pAF-specific aminoacyl tRNA synthetase, for generation of stable clones. The stable clones produce CHv62.21pAF by incorporation of pAF into the MAb. The stable clones were subjected to gene amplification followed by subcloning. The CHv62.21pAF secreted from the stable subclone was purified and evaluated for binding to cell surface FLT3 by flow cytometry. Results show that the recombinant CHv62.21pAF antibody expressed from the CHO cells binds to FLT3 on the cell surface.

The Chinese Hamster Ovary (CHO) cell producing an antibody designated CHv62.21pAF was sent (via Federal Express) to the American Type Culture Collection (ATCC), P.O. Box 1549, Manassas, Va. 20108 on 9 Dec. 2014 and assigned Accession number PTA-121836.

The nucleic acid and amino acid sequences of the variable heavy and light chain regions are listed in FIGS. 2C and/or 2B and FIGS. 3C and/or 3B.

As a result of experimental analysis, using methods known in the art (e.g. protease digestion, LCMS analysis, etc.), amino acid modification(s) of the CHv62.21pAF MAb derived from CHO cells, showed that the deletion of lysine at the C terminal of the heavy chain occurs in most of purified CHv62.21 pAF MAb and pyroglutamylation at the N terminal of the heavy chain and deletion of lysine at the C terminal of the heavy chain occur in a part of purified CHv62.21 pAF MAb.

Example 5

Generation of Linker Unit AGL

In a preferred embodiment, the Linker Unit of the present invention, denoted AGL, is used to link a FLT3 MAb of the present invention, preferably CHv62.21pAF, with a Drug Unit of the present invention, preferably AGD-0182 is commonly known as 2-(aminooxy)acetic acid (Chem-Impex International, Inc., Wood Dale, Ill.).

In a further embodiment, the AGL Linker Unit of the present invention has the following formula:

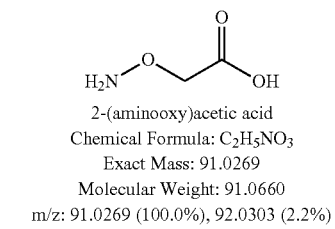

2-(aminooxy)acetic acid
Chemical Formula: $C_2H_5NO_3$
Exact Mass: 91.0269
Molecular Weight: 91.0660
m/z: 91.0269 (100.0%), 92.0303 (2.2%)

Example 6

Generation and Synthesis of AGD-0182 Drug Unit

The Drug Unit set forth in Formula (II) was generated using the following process. First, to a stirred 23° C. suspension of Boc-Dap-OH dicyclohexylamine (10.0 g, 21.3 mmol) and H-Phe-NH$_2$HCl salt (6.42 g, 32.0 mmol) in CH$_2$Cl$_2$ (20.0 mL) was added DIEA (11.0 g, 14.9 mL, 85.3 mmol) followed by the addition of DEPC (5.19 g, 4.80 mL, 0.032 mol). After 10 h, analysis by LCMS showed the reaction was complete. The crude reaction was washed with H₂O (25 mL×2), followed by brine (25 mL×2). The organic fraction was dried over a pad of magnesium sulfate, filtered and concentrated in vacuo. The crude orange oil was purified by flash chromatography (silica gel 40 μm, 60 Å, size) using 2% to 10% methanol in CH₂Cl₂ as the eluent. A total of 7.25 g of Boc-Dap-Phe-NH₂ (16.7 mmol, 78%) was obtained as a yellow oil. LCMS RT=1.28 min (Method B); ESI-MS m/z 434.19 [M+H]⁺.

Second, to a stirred 23° C. suspension of Boc-Dap-Phe-NH₂ (7.25 g, 16.7 mmol) in CH₂Cl₂ (10 mL) was added TFA (10 mL). After 5 h, analysis by LCMS showed the reaction was complete. The volatile organics were evaporated in vacuo to give crude product, which was used without further purification. A total of 6.00 g of H-Dap-Phe-NH₂ was obtained as an orange solid (13.4 mmol, 80%). LCMS RT=0.691 min (Method B); ESI-MS m/z 334.17 [M+H]⁺.

Then to a stirred 23° C. suspension of Fmoc-MeVal-Abu (3-N₃)-Dil-OH TFA salt (456 mg, 0.586 mmol) and H-Dap-Phe-NH₂ TFA salt (457 mg, 1.02 mmol) in DMF (10 mL) was added DIEA (0.350 g, 0.500 mL, 2.74 mmol) followed by the addition of HATU (0.520 g, 1.37 mmol). After 10 h, analysis by LCMS showed the reaction was complete. The crude reaction was purified by preparatory RP-HPLC with a Phenomenex Gemini NX-C18 10μ 110 Å column (150×30 mm) using 10% to 90% MeCN in 0.1% aqueous formic acid as the eluent. A total of 526 mg of Fmoc-MeVal-Abu(3-N₃)-Dil-Dap-Phe-NH₂ was obtained as the formic acid salt (0.513 mmol, 75%). LCMS RT=1.81 min (Method B); ESI-MS m/z 980.39 [M+H]⁺.

Finally, to a stirred 23° C. solution of Fmoc-MeVal-Abu (3-N₃)-Dil-Dap-Phe-NH₂ (525 mg, 0.513 mmol) in acetonitrile (10 mL) was added piperidine (5 mL). After 2 h, analysis by LCMS showed the reaction was complete. To the crude reaction solution was added hexanes (15 mL×3). The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 354 mg of the title compound was obtained as the TFA salt (0.406 mmol, 79%). LCMS RT=1.15 min (Method B); ESI-MS m/z 758.24 [M+H]⁺; HRMS m/z 758.4915 [C₃₈H₆₃N₉O₇+H]⁺.

The foregoing synthesis generated the following Drug Unit denoted (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide, which is set forth as Formula (II):

Example 7

Synthesis of Drug Linker AGL and AGD-0182 Drug Unit

Synthesis of the AGL Linker Unit and the AGD-0182 Drug Unit was completed in the following manner.

Method A is described using the following procedures and protocols:

0-0.50 min: isocratic 80 water/10 acetonitrile/10 1% formic acid in water; 0.50-3.50 min: linear gradient 80 water/10 acetonitrile/10 1% formic acid in water to 0 water/90 acetonitrile/10 1% formic acid in water; 3.50-3.99 min isocratic 0 water/90 acetonitrile/10 1% formic acid in water; 3.99-4.00 min linear gradient 0 water/90 acetonitrile/ 10 1% formic acid in water to 80 water/10 acetonitrile/10 1% formic acid in water.

Method B is described using the following procedures and protocols:

0-0.50 min: isocratic 85 water/5 acetonitrile/10 1% formic acid in water; 0.50-1.60 min: linear gradient 85 water/5 acetonitrile/10 1% formic acid in water to 0 water/98 acetonitrile/2 1% formic acid in water; 1.60-1.80 min isocratic 0 water/98 acetonitrile/2 1% formic acid in water; 1.80-1.90 min linear gradient 0 water/98 acetonitrile/2 1% formic acid in water to 85 water/5 acetonitrile/10 1% formic acid in water; 1.90-2.00 min isocratic 85 water/5 acetonitrile/10 1% formic acid in water.

Using the above methods, the synthesis is as follows:

To a stirred 23° C. suspension of Boc-Dap-OH dicyclohexylamine (10.0 g, 21.3 mmol) and H-Phe-NH₂HCl salt (6.42 g, 32.0 mmol) in CH₂Cl₂ (20.0 mL) was added DIEA (11.0 g, 14.9 mL, 85.3 mmol) followed by the addition of DEPC (5.19 g, 4.80 mL, 0.032 mol). After 10 h, analysis by LCMS showed the reaction was complete. The crude reaction was washed with H₂O (25 mL×2), followed by brine (25 mL×2). The organic fraction was dried over a pad of magnesium sulfate, filtered and concentrated in vacuo. The crude orange oil was purified by flash chromatography (silica gel 40 μm, 60 Å, size) using 2% to 10% methanol in CH₂Cl₂ as the eluent. A total of 7.25 g of Boc-Dap-Phe-NH₂ (16.7 mmol, 78%) was obtained as a yellow oil. LCMS RT=1.28 min (Method B); ESI-MS m/z 434.19 [M+H]⁺.

To a stirred 23° C. suspension of Boc-Dap-Phe-NH₂ (7.25 g, 16.7 mmol) in CH₂Cl₂ (10 mL) was added TFA (10 mL). After 5 h, analysis by LCMS showed the reaction was complete. The volatile organics were evaporated in vacuo to give crude product, which was used without further purification. A total of 6.00 g of H-Dap-Phe-NH₂ was obtained as an orange solid (13.4 mmol, 80%). LCMS RT=0.691 min (Method B); ESI-MS m/z 334.17 [M+H]⁺.

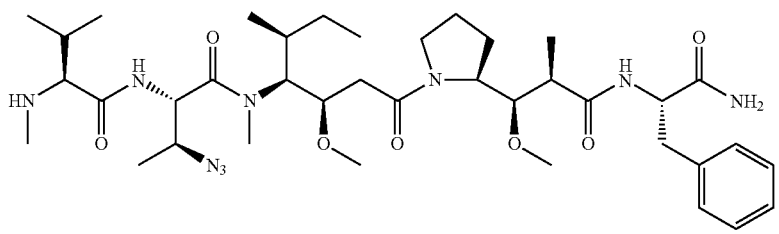

(II)

To a stirred 23° C. suspension of Fmoc-MeVal-Abu(3-N₃)-Dil-OH TFA salt (456 mg, 0.586 mmol) and H-Dap-Phe-NH₂ TFA salt (457 mg, 1.02 mmol) in DMF (10 mL) was added DIEA (0.350 g, 0.500 mL, 2.74 mmol) followed by the addition of HATU (0.520 g, 1.37 mmol). After 10 h, analysis by LCMS showed the reaction was complete. The crude reaction was purified by preparatory RP-HPLC with a Phenomenex Gemini NX-C18 10µ 110 Å column (150×30 mm) using 10% to 90% MeCN in 0.1% aqueous formic acid as the eluent. A total of 526 mg of Fmoc-MeVal-Abu(3-N₃)-Dil-Dap-Phe-NH₂ was obtained as the formic acid salt (0.513 mmol, 75%). LCMS RT=1.81 min (Method B); ESI-MS m/z 980.39 [M+H]⁺.

To a stirred 23° C. solution of Fmoc-MeVal-Abu(3-N₃)-Dil-Dap-Phe-NH₂ (525 mg, 0.513 mmol) in acetonitrile (10 mL) was added piperidine (5 mL). After 2 h, analysis by LCMS showed the reaction was complete. To the crude reaction solution was added hexanes (15 mL×3). The acetonitrile layer was concentrated in vacuo. The crude oil was purified by preparatory RP-HPLC with a Phenomenex Gemini NX-C18 10µ 110 Å column (150×30 mm) using 5% to 95% MeCN in 0.1% aqueous TFA as the eluent. A total of 354 mg of the resulting compound (MeVal-Abu(3-N₃)-Dil-Dap-Phe-NH₂) was obtained as the TFA salt (0.406 mmol, 79%). LCMS RT=1.15 min (Method B); ESI-MS m/z 758.24 [M+H]⁺; HRMS m/z 758.4915 [C₃₈H₆₃N₉O₇+H]⁺.

To a stirred 23° C. solution of MeVal-Abu(3-N₃)-Dil-Dap-Phe-NH₂ (2.0 g, 2.64 mmol) and Boc-Aoa (0.53 g, 2.77 mmol) in DMF (7.0 mL) and DCM (15.0 mL) was added HATU (1.05 g, 2.77 mmol), followed by the addition of DIPEA (0.51 mL, 2.92 mmol). After 1 h, the reaction mixture was concentrated in vacuo to yield a crude DMF solution which was further diluted with 150 mL of EtOAc. The crude reaction mixture was washed with 100 mL of Sat. NaHCO₃, followed by 100 mL of brine. The organic fraction was dried over a pad of magnesium sulfate, filtered and concentrated in vacuo. The crude Boc-Aoa-MeVal-Abu(3-N₃)-Dil-Dap-Phe-NH₂ was purified by flash chromatography (silica gel 40 µm, 60 Å, size) using 0% to 5% methanol in CH₂Cl₂ as the eluent. A total of 2.13 g of Boc-Aoa-MeVal-Abu(3-N₃)-Dil-Dap-Phe-NH₂ (2.29 mmol, 87%) was obtained as a beige-colored solid. LCMS RT=1.46 min (Method A); ESI-MS m/z 931.46 [M+H]⁺.

To a stirred 23° C. solution of Boc-Aoa-MeVal-Abu(3-N₃)-Dil-Dap-Phe-NH₂ (2.1 g, 2.26 mmol) in dioxane (15.0 mL) was added 4 M HCl in dioxane (10.0 mL, 40.0 mmol). After 0.5 h, the reaction mixture was concentrated in vacuo to yield a crude pale-yellow oil. The crude pale-yellow oil from was dissolved in 6 mL of methanol and was slowly added (dropwise) to vigorously stirred 150 mL solution of EtOAc. A white precipitate was obtained from the solution. The white precipitate from was collected by filtration, and the supernatant was concentrated to a solid. Both the white precipitate and the concentrated supernatant were purified in several portions by preparatory RP-HPLC with a Phenomenex Gemini 10µ, C18 110 Å column (150×30 mm) using 5% to 95% MeCN in 0.001 M hydrochloric acid as the eluent.

The resulting product fractions were combined, concentrated, and dried in vacuo for 18 h to yield a white-colored solid. A total of 1.31 g of AGL-0182-30*HCl (1.51 mmol, 67%) was obtained. LCMS RT=1.16 min (Method A); ESI-MS m/z 831.27 [M+H]⁺. (See, generally Table IV).

In a preferred embodiment, AGL-0182-30 has the following formula:

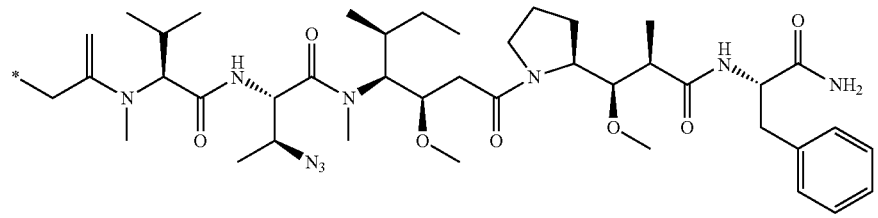 [SMILES: *CC(=C)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(N)=O)OC)[C@H](C)N=[N+]=[N-])C(C)C]

Example 8

Antibody Drug Conjugation of CHv62.21pAF MAb

The CHv62.21pAF Mab was conjugated to a dolaisoluine-dolaproine containing peptide designated AGL-0182-30 using an alkoxyamine linker described herein to create the antibody drug conjugate (ADC) of the invention designated CHv62.21pAF-AGL-0182-30 using the following protocols.

The synthesis of the AGL-0182-30 drug linker was accomplished using the methods described in Example 7 entitled "Synthesis of Drug Linker AGL and AGD-0182 Drug Unit".

Next, the antibody drug conjugate (ADC) of the invention designated cHv62.21pAF-AGL-0182-30 was made using the following protocols.

Briefly, 215.5 mL of the CHv62.21pAF Mab at a concentration of 17.17 mg/mL formulated in 50 mM citrate buffer containing 500 mM NaCl at a final pH of 4.0 is added to 9.7 mL of 50 mM citrate buffer containing 500 mM NaCl at a final pH of 4.0, 9.1 mL of 1.35 M acetic hydrazide (dissolved in water), 7.26 mL of DMSO, and 5.08 mL of a 50 mM solution of AGL-0182-30 (dissolved in DMSO). Conjugation is allowed to proceed at 28° C. for 16-24 hours. Excess AGL-0182-30 and other small molecule reaction components are removed by ultrafiltration/diafiltration with 12 diavolumes of 20 mM Histidine pH 6.0 containing 5% trehalose.

The resulting antibody drug conjugate (ADC) is designated CHv62.21pAF-AGL-0182-30 and has the following formula:

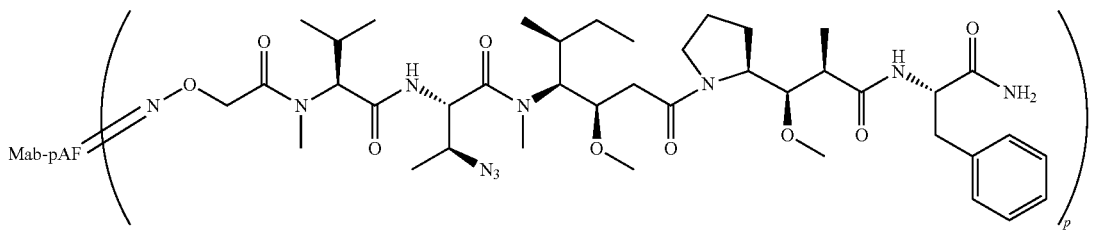

Wherein the Mab is CHv62.21pAF and p is from 1.8 to 2.0. The average p value of the antibody drug conjugate set forth in this Example was approximately 1.9 by Mass Spec analysis. In one embodiment of the present invention, the p value is between 1.5 and 2.5.

The resulting ADC of the present invention incorporates a nnAA into the antibody component of the ADC whereby the Drug Linker is conjugated via oxime bond and is used for the therapeutic treatment of the cancers set forth in Table I.

Example 9

Characterization of CHv62.21 MAb

MAbs that bind FLT3 were generated using the procedures set forth in the example entitled "Generation of FLT3 Monoclonal Antibodies (MAbs)" and were screened, identified, and characterized using a combination of assays known in the art.

A. FACS Binding

CHv62.21 was tested for binding to AML and B-ALL cell lines grown in vitro. (See, FIGS. 15A-15M). Briefly, CHv62.21 and an isotype matched control antibody were biotinylated using NHS LC biotin. In vitro, exponentially grown cancer cell lines were used for all experiments. Cells were harvested by and washed by centrifugation. Cells were Fc blocked to reduce non-specific binding. Antibodies were diluted to 10 ug/ml final concentration and co-incubated with cells at 4° C. for 1 hour. At the end of the incubation, cells were washed and incubated with secondary detection Streptavidin-PE antibody at a final 1:200 (2.5 ug/ml) dilution for 1 hour at 4° C. After washing un-bound secondary antibody, cells were analyzed by FACS and geometric mean fluorescence was determined and reported. Fluorescence ratio was calculated as follows: Geo mean cHv62.21/Geo mean isotype control=MFR, a measure of fold expression above isotype control.

Geometric Mean values and Mean Florescence ratios (MFR) values were obtained (Table VI) and histograms are shown (FIGS. 15A-15M). The results show that the CHv62.21 binds several human cancer cell lines expressing AML and B-ALL.

B. ADCC Activity

CHv62.21 and CHv62.21pAF was tested for ADCC activity in vitro. Briefly, the naked and ADC anti-FLT3 monoclonal antibodies, CHv62.21 and CHv62.21pAF were tested for their ability to mediate antibody dependent cytotoxicity activity (ADCC) using the target cell lines EOL-1 and SEM in the presence of the effector cells, normal human PBMCs using the CytoTox 96® Non-Radioactive Cytotoxicity Assay (Promega, G1780).

One (1) day prior to performing the assay, three (3) vials of the effector cells, normal human PBMC (Hemacare, Donor ID: 1888), were thawed, washed and plated into T-175 cell culture flasks in RPMI-1640 supplemented with 10% heat inactivated fetal bovine serum. The flasks were stored in an incubator at 37° C. 5% CO2 overnight. The next day, the PBMCs were harvested from the culture flasks using 0.25% Trypsin-EDTA (Gibco) and washed and seeded at a concentration of 1.0e6 cells/well in assay buffer (RPMI1640+0.1% FBS). The target cells SEM and EOL-1 along with the positive control cell line, Raji were harvested, washed and seeded at a concentration of 2.0e5 cells/well using assay buffer.

The test samples were each diluted to a final concentration of 2.5 ug/mL in assay buffer. Equal volumes of target cells, test sample, and effector cells were added to wells of a 96-well round bottom plate in triplicate. The plate was gently centrifuged and incubated for 4 hours in a humidified 37° C. incubator. After the four (4) hour incubation, the assay plates were centrifuged and a volume of 50 µL of the supernatant was harvested and transferred to a fresh 96-well plate. The activity of lactate dehydrogenase in the supernatant was determined by using the colorimetric LDH Detection Kit; CytoTox 96® Non-Radioactive Cytotoxicity Assay (Promega) with absorbance readings taken at 490 nm.

The data was analyzed by first subtracting the average of absorbance values of the Culture Medium Background wells from all absorbance values of Experimental, Effector spontaneous, Target spontaneous and Target maximum wells. Next, the average of the corrected absorbance readings was normalized and ADCC activity was calculated by using the following formula:

$$ADCC(\%) = \frac{\text{Experimental} - \text{Effector Spontaneous} - \text{Target Spontaneous}}{\text{Target Maximum} - \text{Target Spontaneous}} \times 100$$

Figure 7:
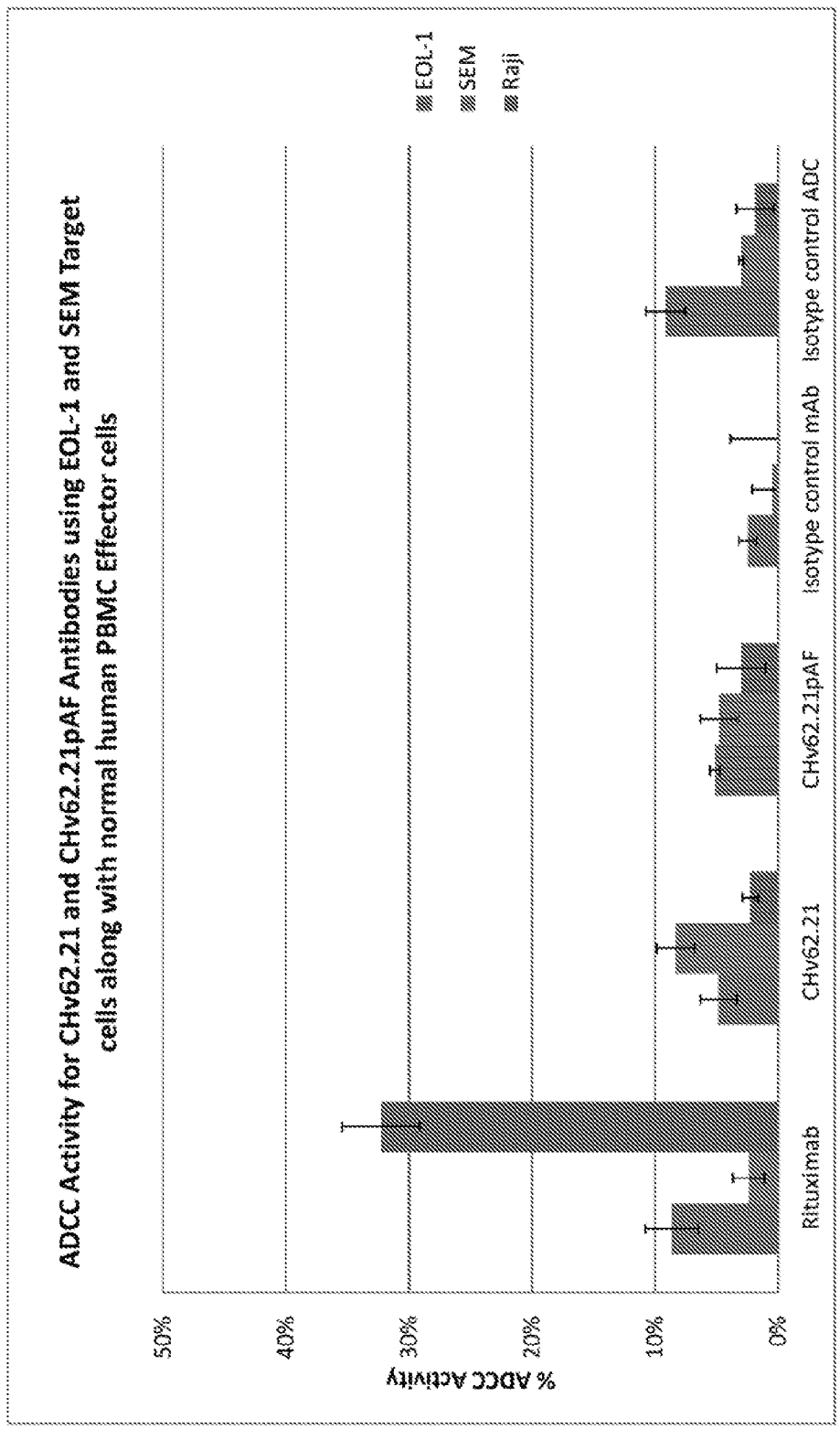
FIG. 7. CHv62.21 and CHv62.21pAF does not Mediate Antibody Dependent Cytotoxicity Activity (ADCC) in vitro EOL-1, SEM, and Raji (left to right in the figure). Assay details: 1) E:T=100:1; 2) Antibody concentration=2.5 µg/mL; 3) Incubation time: 4H; 4) Isotype control mAb & ADC: AGS91.1-L363-pAF, AGS91.88-pAF-AGSL-0182-30; 5) Positive control: Rituximab targeting Raji cells.

The results in FIG. 7 show that CHv62.21 and CHv62.21pAF MAbs do not show ADCC activity. However, the positive control, Rituximab confirms ADCC activity in Raji cell line.

Example 10

CHv62.21pAF-AGL-0182-30 Inhibit Growth of Tumors In Vivo

The significant expression of FLT3 in tumor cells, together with its restrictive expression in normal cells makes FLT3 a good target for antibody therapy and similarly, therapy via ADC. Thus, the therapeutic efficacy of CHv62.21pAF-AGL-0182-30 in human ALL, AML, and B-LL cancer xenograft mouse models is evaluated.

Antibody drug conjugate efficacy on tumor growth and metastasis formation is studied in mouse cancer xenograft models (e.g. subcutaneous and orthotopically).

Subcutaneous (s.c.) tumors are generated by injection of $5 \times 10^4$-$10^6$ cancer cells mixed at a 1:1 dilution with Matrigel (Collaborative Research) in the right flank of male SCID mice. To test ADC efficacy on tumor formation, i.e. ADC injections are started on the same day as tumor-cell injections. As a control, mice are injected with either purified human IgG or PBS; or a purified MAb that recognizes an irrelevant antigen not expressed in human cells. In preliminary studies, no difference is found between control IgG or PBS on tumor growth. Tumor sizes are determined by caliper measurements, and the tumor volume is calculated as width$^2 \times$Length/2, wherein width is the smallest dimension and length is the largest dimension. Mice with subcutaneous tumors greater than 1.5 cm in diameter are sacrificed.

An advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

CHv62.21pAF-AGL-0182-30 ADC inhibits formation in cancer cell line(s) denoted MV4-11 subcutaneous established cancer xenografts. These results indicate the utility of CHv62.21pAF-AGL-0182-30 in the treatment of local and advanced stages of cancer and preferably those cancers set forth in Table I.

FLT3 ADCs:

Monoclonal antibodies were raised against FLT3 as described in the Example entitled "Generation of FLT3 Monoclonal Antibodies (MAbs)." Further the MAbs are conjugated to a toxin as described in the Example entitled "Antibody Drug Conjugation of CHv62.21pAF MAb" to form CHv62.21pAF-AGL-0182-30. The CHv62.21pAF and CHv62.21pAF-AGL-0182-30 is characterized by FACS, and other methods known in the art to determine its capacity to bind FLT3.

Cell Lines and Xenografts:

The cells are maintained in DMEM, supplemented with L-glutamine and 10% FBS, as known in the art. The MV4-11 xenografts are maintained by serial propogation in SCID mice.

Efficacy and Dose Titration of CHv62.21pAF-AGL-0182-30 in the Subcutaneously Established Xenograft Model of Human B Myelomonocytic Leukemia Cell Line MV4-11 Implanted in CB17/SCID Mice.

In this experiment, Human B myelomonocytic leukemia MV4-11 cells ($3.0 \times 10^6$ cells per mouse) were injected into the flanks of individual SCID mice and tumors were allowed to grow. When the average tumor volumes reached a predetermined size (200 mm$^3$), animals were tumor-size matched and randomized into treatment and control groups with similar mean tumor size and variation in each group using Study Director Software (v.2.1; Studylog Systems, Inc., South San Francisco, Calif.). All the study mice were pre-loaded with Fc blocker (mLYS-1c3.1-hIgG1) at 20 mg/kg by intraperitoneal injection in the afternoon before the day of drug administration.

CHv62.21pAF-AGL-0182-30 was dosed at 3 different dosing levels (0.5, 1.0, and 2.0 mg/kg) as single bolus by intravenous injection. 20 mM Histidine/5% Trehalose, pH 6.0 and 91.1-AGL-0182-30 were used as the vehicle and ADC controls, respectively. All agents were administered based on the individual body weight of each animal obtained immediately prior to each dosing. Tumor growth in each group was monitored twice weekly using caliper measurements until study termination. A statistical analysis of the tumor volume data for the last day before animal sacrifice was performed using the Kruskal-Wallis test. Pairwise comparisons were made using Tukey's test procedures (2-sided) to protect the experiment-wise error rate.

This study evaluated the efficacy of CHv62.21pAF-AGL-0182-30 and compared it to its ADC control (91.1-AGL-0182-30) in the MV4-11 human B myelomonocytic leukemia xenograft model subcutaneously established in CB17/SCID mice. CHv62.21pAF-AGL-0182-30 was administered at 3 different dosing levels (0.5, 1.0, and 2.0 mg/kg) as a single dose by intravenous (i.v.) bolus injection. 91.1-AGL-0182-30 was dosed at 2 mg/kg by i.v. as the ADC control. And 20 mM Histidine/5% Trehalose, pH 6.0 was used as the vehicle control.

The results indicated no statistic difference between the treatments of the vehicle and ACD controls (p>0.9999). CHv62.21pAF-AGL-0182-30 at 2.0 mg/kg statistically significantly regressed the tumor by 100% (p<0.0001), when compared to the starting tumor size at the commencement of dosing. Compared to the vehicle control, CHv62.21pAF-AGL-0182-30 at 1.0 mg/kg statistically significantly inhibited tumor growth by 78.1% (p<0.0001). CHv62.21pAF-AGL-0182-30 did not show any efficacy in this model at the dose of 0.5 mg/kg (p=0.5344). (FIG. 5).

Efficacy of CHv62.21pAF-AGL-0182-30 (ADC) and CHv62.21pAF (Naked Antibody) in the Subcutaneously Established Xenograft Model of Human B Myelomonocytic Leukemia Cell Line MV4-11 Implanted in CB17 SCID Mice.

In another experiment, Human B myelomonocytic leukemia MV4-11 cells ($3.0 \times 10^6$ cells per mouse) were injected into the flanks of individual SCID mice and tumors were allowed to grow. When the average tumor volumes reached a predetermined size (200 mm$^3$), animals were tumor-size matched and randomized into treatment and control groups with similar mean tumor size and variation in each group using Study Director Software (v.2.1; Studylog Systems, Inc., South San Francisco, Calif.). All the study mice were pre-loaded with Fc blocker (mLYS-1c3.1-hIgG1) at 20 mg/kg by intraperitoneal injection in the afternoon before the day of drug administration. CHv62.21pAF-AGL-0182-30 and the ADC control (91.1-AGL-0182-30) were dosed at 1 mg/kg as single bolus by intravenous injection. AGS62P (a.k.a. CHv62.21pAF) and the naked antibody control (91.1-pAF) were dosed at 2 mg/kg as single bolus by intravenous injection. All agents were administered based on the individual body weight of each animal obtained immediately prior to each dosing. Tumor growth in each group was monitored twice weekly using caliper measurements until study termination. A statistical analysis of the tumor volume data for the last day before animal sacrifice was performed using the Kruskal-Wallis test. Pairwise comparisons were made using Tukey's test procedures (2-sided) to protect the experiment-wise error rate.

This study evaluated efficacy of CHv62.21pAF-AGL-0182-30 (ADC) and CHv62.21pAF (naked antibody).

Figure 6:
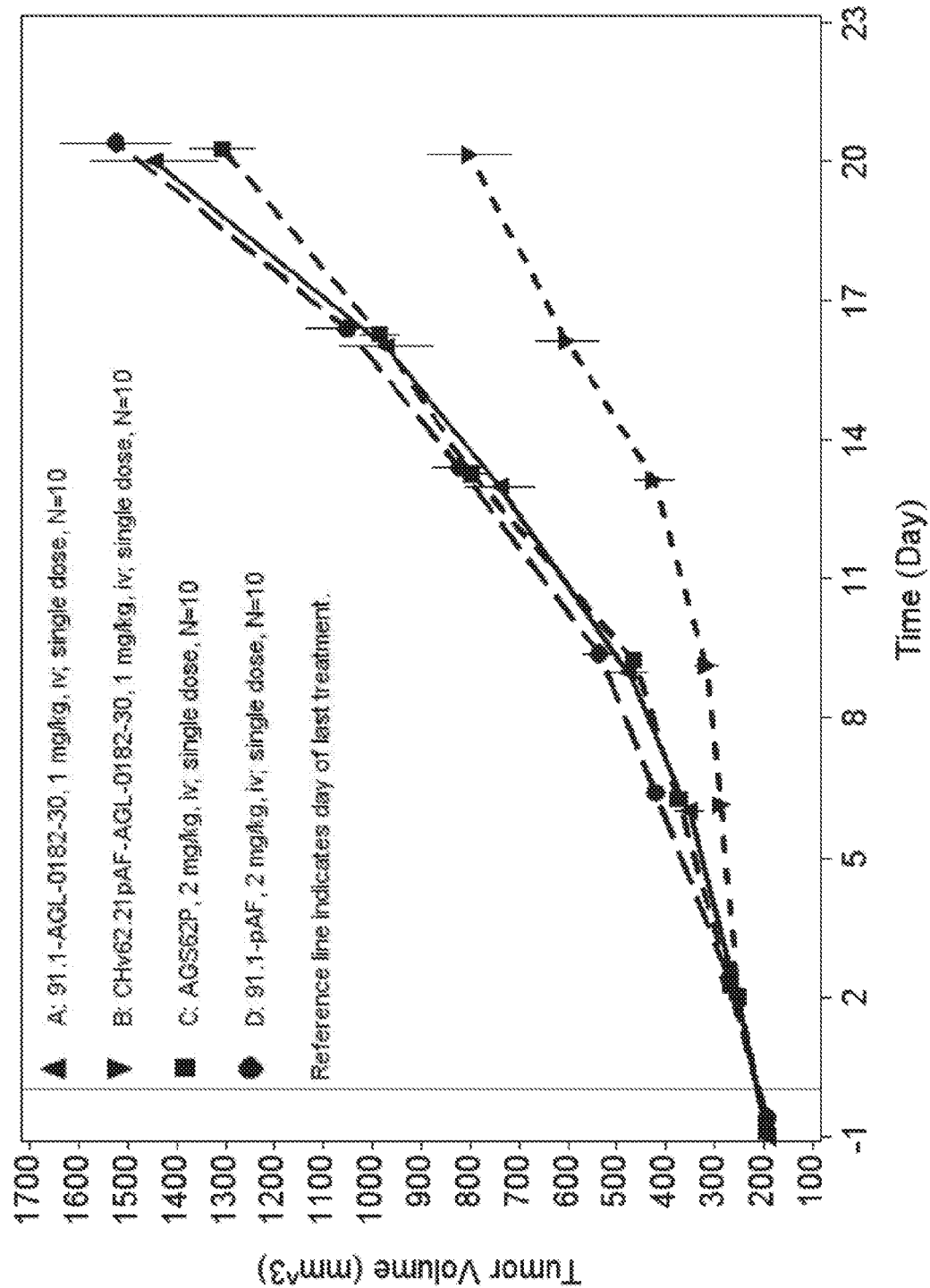
FIG. 6. Efficacy Study of CHv62.21pAF-AGL-0182-30 (ADC) and CHv62.21pAF (AGS62P) (naked antibody) in subcutaneously established xenograft model of human B myelomonocytic leukemia cell line MV4-11 implanted in CB17 SCID mice.

The results show that compared to the ADC control (91.1-AGL-0182.30), CHv62.21pAF-AGL-0182-30 at 1.0 mg/kg as a single dose by intravenous injection statistically significantly inhibited tumor growth by 51.4% (p=0.0010). Compared to the naked antibody control (91.1-pAF), CHv62.21pAF at 2.0 mg/kg as a single dose by intravenous injection showed no statistically different (p=0.6570). Furthermore, the results indicated CHv62.21pAF-AGL-0182-30 at 1.0 mg/kg statistically significantly inhibited tumor growth by 54.3%, when compared to CHv62.21pAF at 2.0 mg/kg (p=0.0134). (FIG. 6).

Efficacy of CHv62.21pAF-AGL-0182-30 (ADC) and CHv62.21pAF (Naked Antibody) in the Subcutaneously Established Xenograft Model of Human B Myelomonocytic Leukemia Cell Line MV4-11 Implanted in CB17 SCID Mice.

In another experiment, Human B myelomonocytic leukemia MV4-11 cells ($3.0 \times 10^6$ cells per mouse) were injected into the flanks of individual SCID mice and tumors were allowed to grow. When the average tumor volumes reached a predetermined size (200 mm$^3$), animals were tumor-size matched and randomized into treatment and control groups with similar mean tumor size and variation in each group using Study Director Software (v.2.1; Studylog Systems, Inc., South San Francisco, Calif.). All the study mice were pre-loaded with Fc blocker (mLYS-1c3.1-hIgG1) at 20 mg/kg by intraperitoneal injection in the afternoon before the day of drug administration. CHv62.21pAF-AGL-0182-30 and the ADC control (91.1-AGL-0182-30) were dosed at 2 mg/kg QW for 2 weeks by intravenous injection. AGS62P (a.k.a. CHv62.21pAF) and the naked antibody control (91.1-pAF) were dosed at 2 mg/kg QW for weeks by intravenous injection. All agents were administered based on the individual body weight of each animal obtained immediately prior to each dosing. Tumor growth in each group was monitored twice weekly using caliper measurements until study termination. A statistical analysis of the tumor volume data for the last day before animal sacrifice was performed using the Kruskal-Wallis test. Pairwise comparisons were made using Tukey's test procedures (2-sided) to protect the experiment-wise error rate.

This study evaluated efficacy of CHv62.21pAF-AGL-0182-30 (ADC) and Chv62.21pAF (naked antibody) using a multiple dose regiment over a 2 week timeframe.

Figure 13:
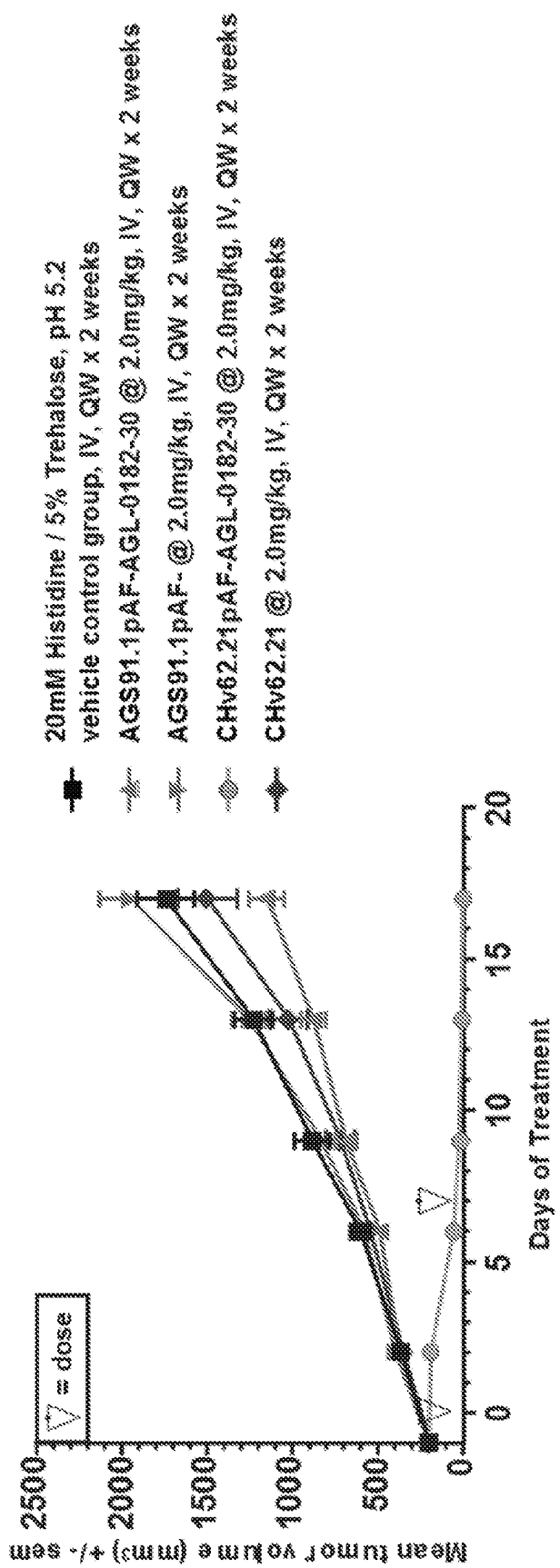
FIG. 13. Efficacy Study of CHv62.21pAF-AGL-0182-30 (ADC) and CHv62.21pAF (naked antibody) in the subcutaneously established xenograft model of human B myelomonocytic leukemia cell line MV4-11 implanted in CB17 SCID mice using multiple dose regime.

The results show that compared to the ADC control (91.1-AGL-0182.30), CHv62.21pAF-AGL-0182-30 at 2.0 mg/kg as a multiple dose by intravenous injection statistically significantly inhibited tumor growth with 100% tumor regression at day 17 (p=0.0001). Compared to the naked antibody control (91.1-pAF), CHv62.21pAF at 2.0 mg/kg as a multiple dose by intravenous injection showed no statistically different. (FIG. 13).

Efficacy of CHv62.21pAF-AGL-0182-30 in the Subcutaneously Established SEM-Xcl Xenograft Model in CB17 SCID Mice.

In another experiment, human Acute Lymphoblastic Leukemia SEM-xcl cells ($1.0 \times 10^6$ cells per mouse) were injected into the flanks of individual SCID mice and tumors were allowed to grow. When the average tumor volumes reached a predetermined size (200 mm3), animals were tumor-size matched and randomized into treatment and control groups with similar mean tumor size and variation in each group using Study Director Software (v.2.1; Studylog Systems, Inc., South San Francisco, Calif.).

CHv62.21pAF-AGL-0182-30 was dosed at 5.0 mg/kg, 2.0 mg/kg, or 1.0 mg/kg as a single bolus dose on day 0 by intravenous injection. Control ADC, AGS91.1-pAF-AGL-0182-30, was dosed at 5.0 mg/kg using the same route and dosing schedule. 20 mM histidine/5% trehalose, pH 5.2 was used as the vehicle. All agents were administered based on the individual body weight of each animal obtained immediately prior to each dosing. Tumor growth in each group was monitored twice weekly using caliper measurements until study termination. A statistical analysis of the tumor volume data for the last day before animal sacrifice was performed using the Kruskal-Wallis test. Pairwise comparisons were made using Tukey's test procedures (2-sided) to protect the experiment-wise error rate.

Figure 14:
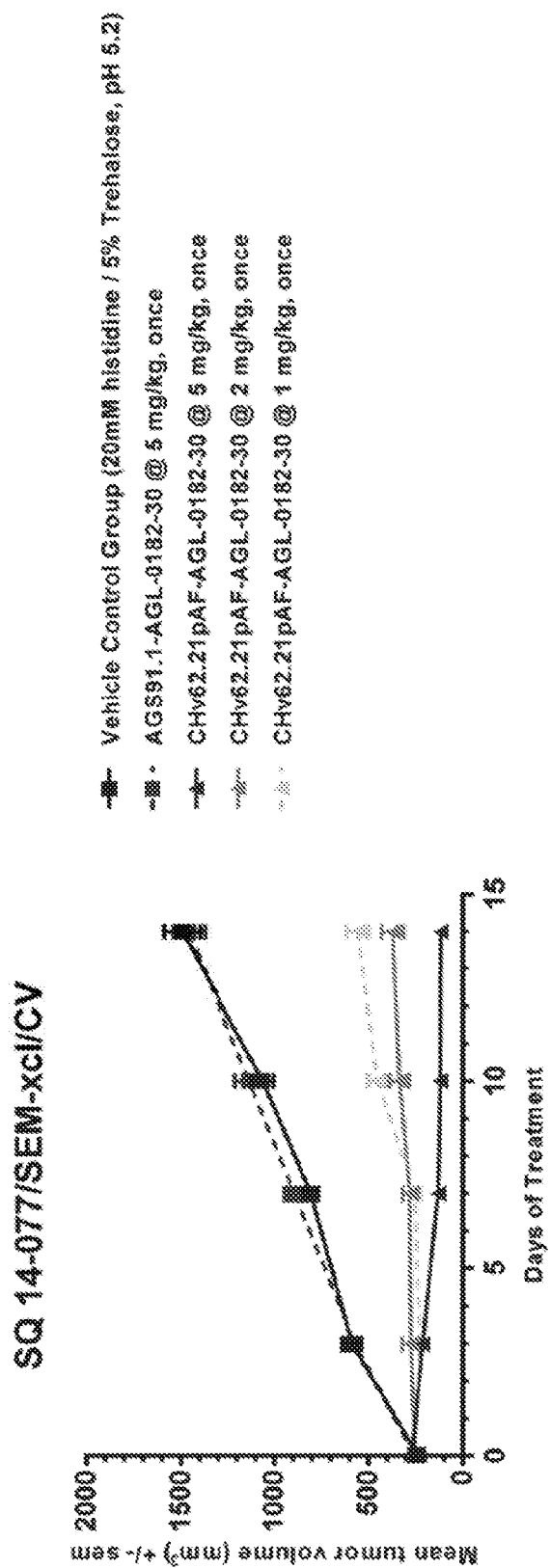
FIG. 14. Efficacy of CHv62.21pAF-AGL-0182-30 in the subcutaneously established SEM-xcl xenograft model.
Figure 15B:
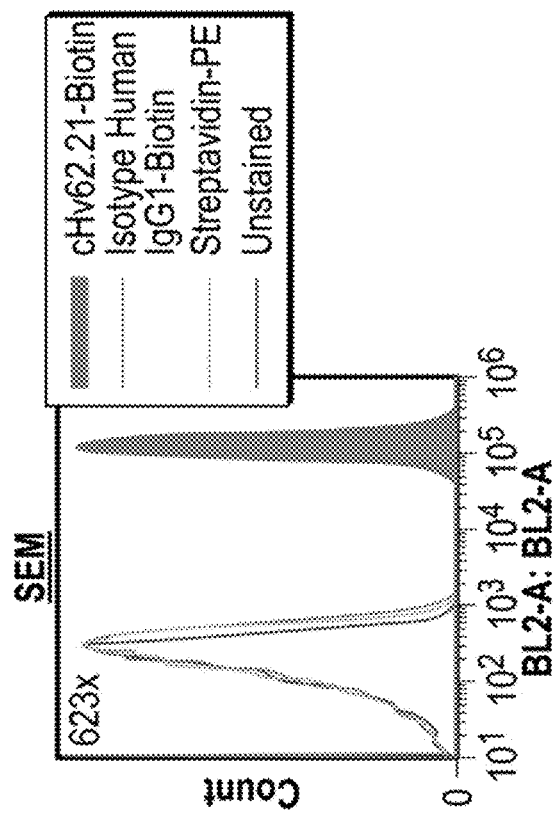
FIGS. 15A-15M. Histograms showing results of FACS binding per cell line.
Figure 15D:
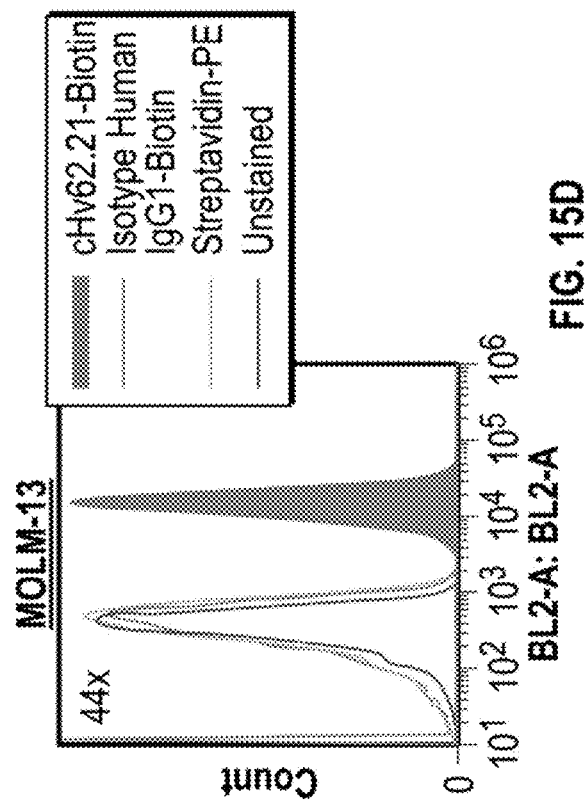
Figure 15A:
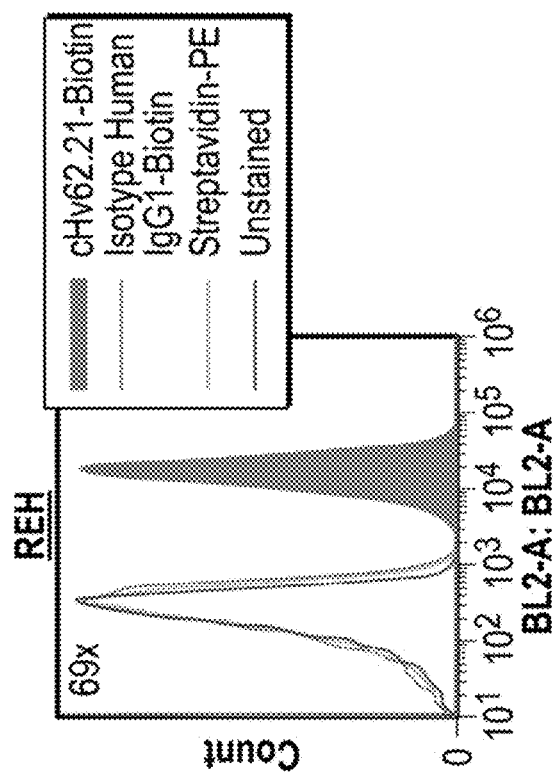
Figure 15C:
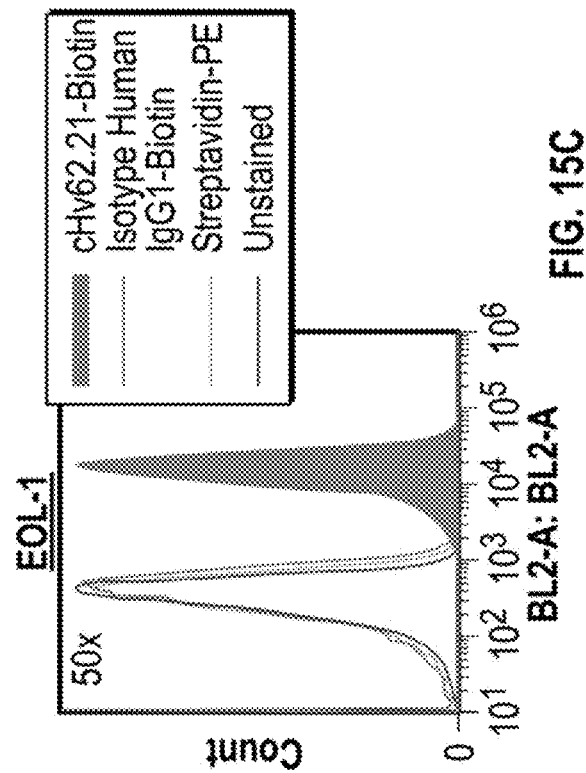
Figure 15E:
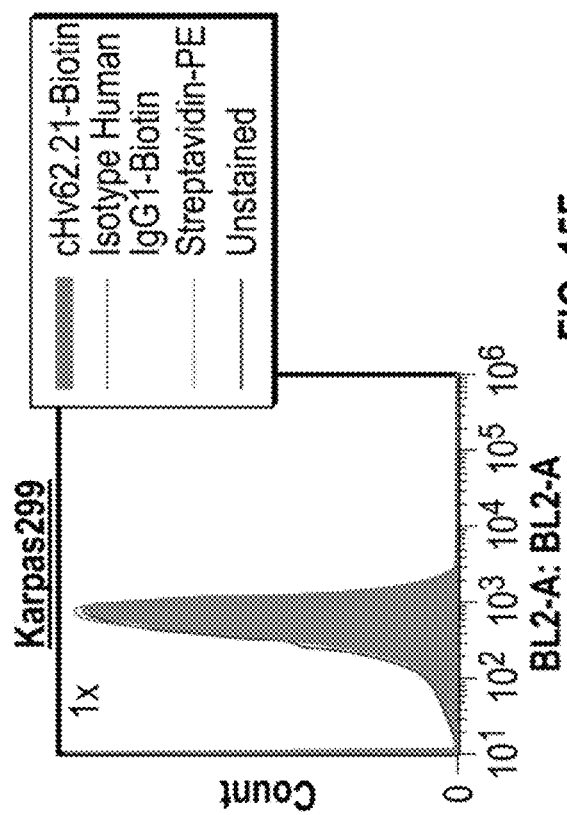
Figure 15F:
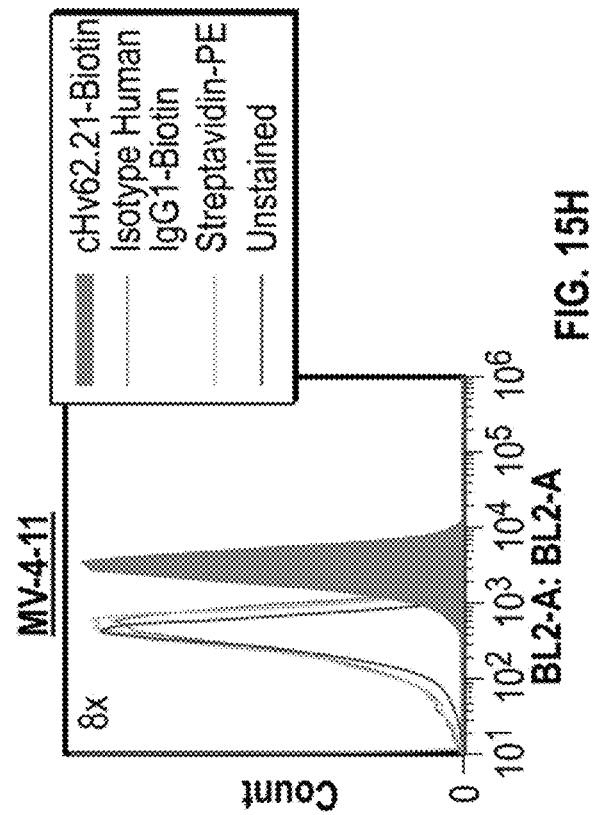
Figure 15G:
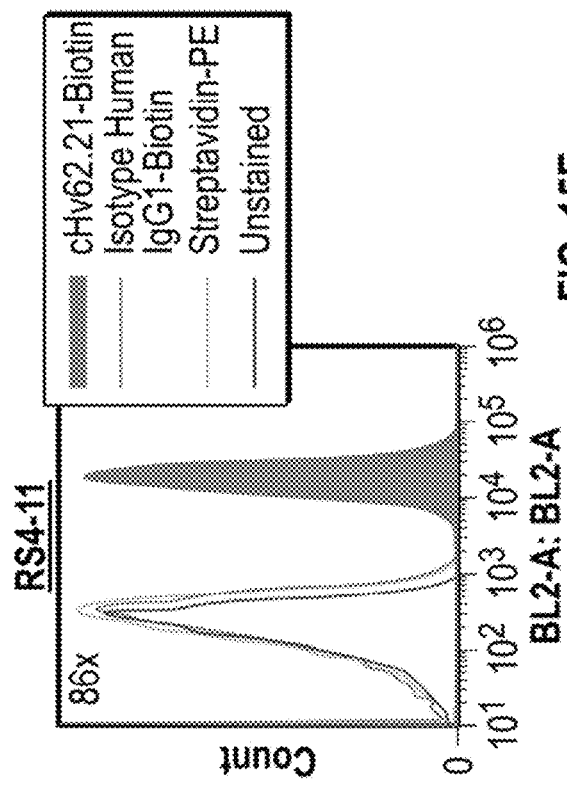
Figure 15H:
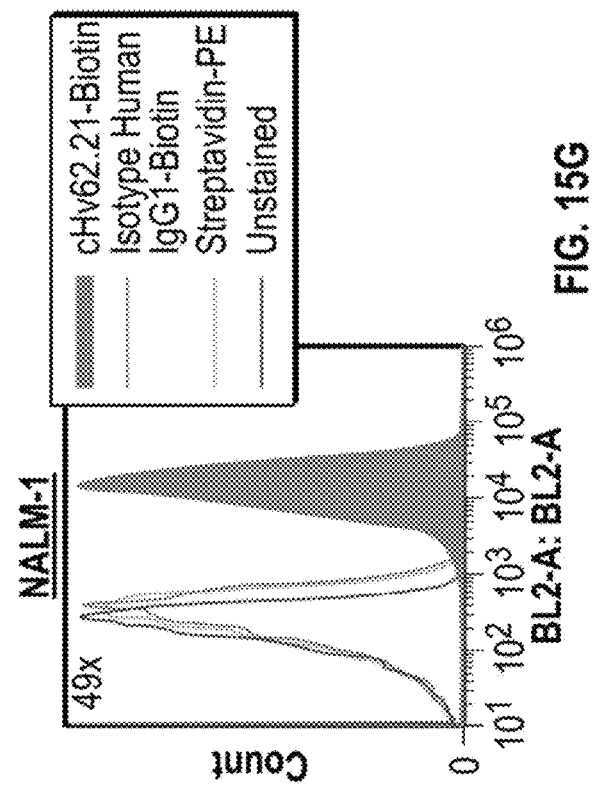
Figure 15I:
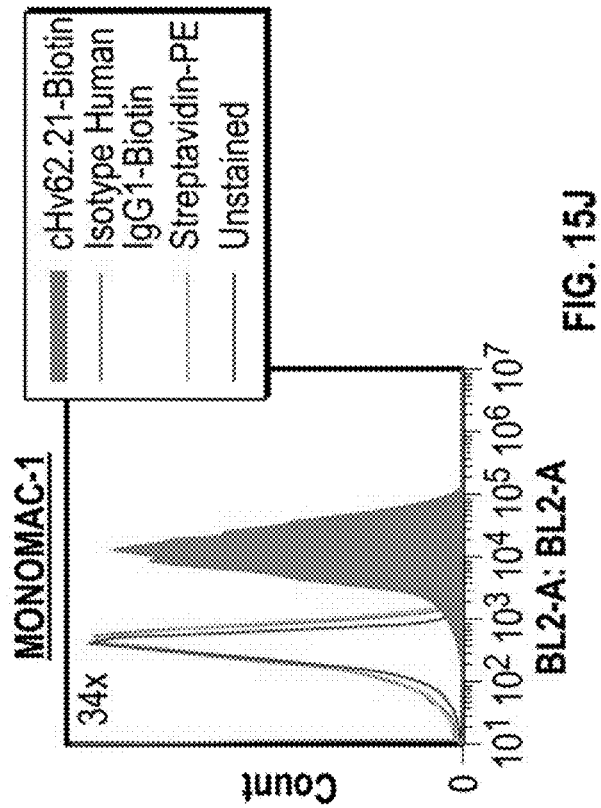
Figure 15J:
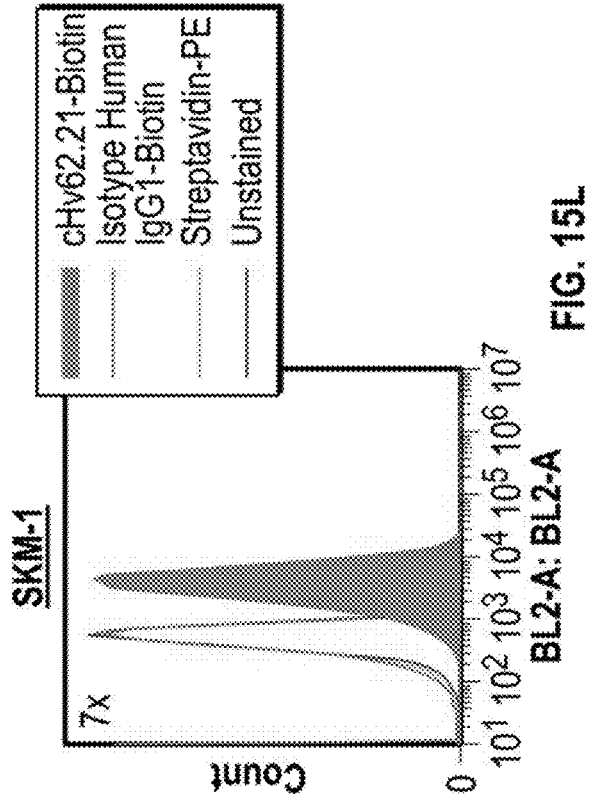
Figure 15K:
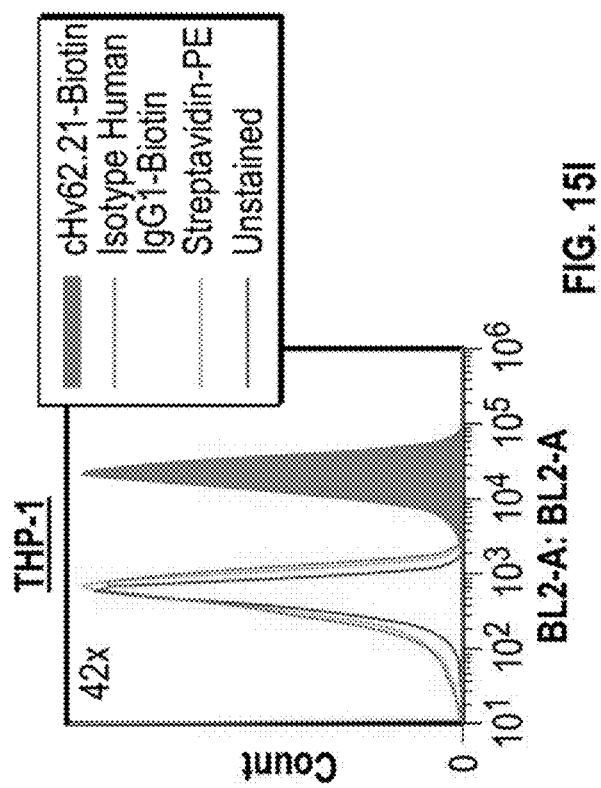
Figure 15L:
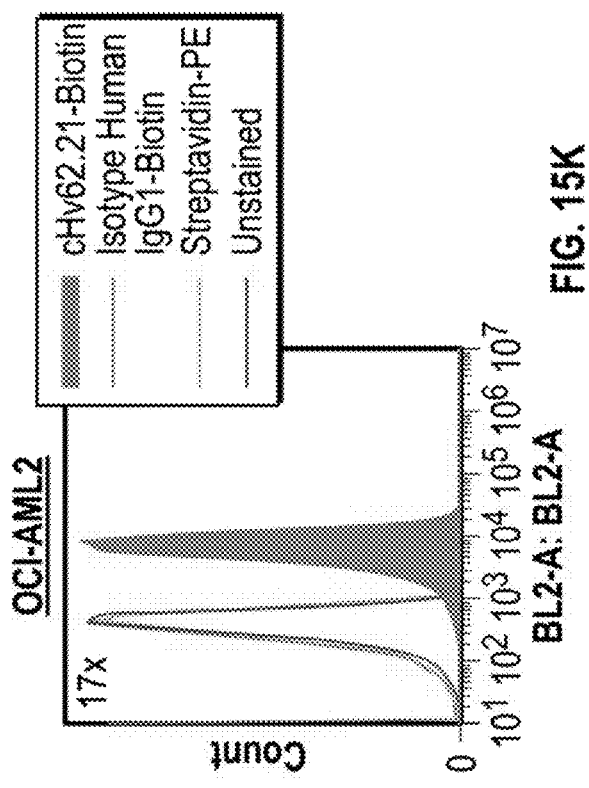
Figure 15M:
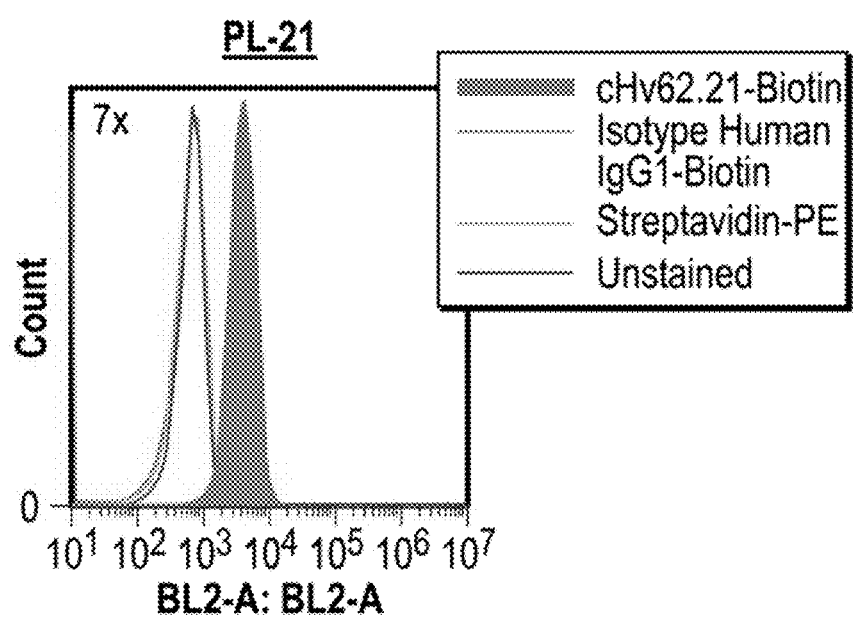

The results show that CHv62.21pAF-AGL-0182-30 at all three dosage levels (5.0, 2.0 and 1.0 mg/kg) demonstrated potent anti-tumor activity when compared to the control ADC, AGS91.1-pAF-AGL-0182-30, or to the vehicle control (p<0.0001), resulting in more than 75% tumor growth inhibitions in general. Moreover, when dosed at 5.0 mg/kg, CHv62.21pAF-AGL-0182-30 significantly regressed the tumor by 57.3% when compared to its initial starting tumor volume. Statistically significant difference in efficacy between 5.0 mg/kg and 2.0 mg/kg or 1.0 mg/kg was observed. (FIG. 14).

Conclusion

In summary, FIGS. 5, 6, 13 and 14 show that the FLT3 ADC entitled CHv62.21pAF-AGL-0182-30 significantly inhibited the growth of tumors cells that express FLT3 when compared to control ADCs and naked antibodies that bind FLT3. Thus, the CHv62.21pAF-AGL-0182-30 can be used for therapeutic purposes to treat and manage cancers set forth in Table I.

Example 11

Human Clinical Trials for the Treatment and Diagnosis of Human Carcinomas Through Use of FLT3 ADCs FLT3 ADCs are used in accordance with the present invention which specifically bind to FLT3, and are used in the treatment of certain tumors, preferably those listed in Table I. In connection with each of these indications, two clinical approaches are successfully pursued.

I.) Adjunctive therapy: In adjunctive therapy, patients are treated with FLT3 ADCs in combination with a chemotherapeutic or anti-neoplastic agent and/or radiation therapy or a combination thereof. Primary cancer targets, such as those listed in Table I, are treated under standard protocols by the addition of FLT3 ADCs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. FLT3 ADCs are utilized in several adjunctive clinical trials in combination with the chemotherapeutic or anti-neoplastic agents.

II.) Monotherapy: In connection with the use of the FLT3 ADCs in monotherapy of tumors, the FLT3 ADCs are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and/or ADC and the particular therapeutic or prophylactic effect to be achieved, and (b) the limitations inherent in the art of compounding such an active compound for the treatment of sensitivity in individuals.

An exemplary, non limiting range for a therapeutically effective amount of an FLT3 ADC administered in combination according to the invention is about 0.5 to about 10 mg/kg, about 1 to about 5 mg/kg, at least 1 mg/kg, at least 2 mg/kg, at least 3 mg/kg, or at least 4 mg/kg. Other exemplary non-limiting ranges are for example about 0.5 to about 5 mg/kg, or for example about 0.8 to about 5 mg/kg, or for example about 1 to about 7.5 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of FLT3 ADCs in connection with adjunctive therapy or monotherapy. Trials initially demonstrate safety and thereafter confirm efficacy in repeat doses. Trials are open label comparing standard chemotherapy with standard therapy plus FLT3 ADCs. As will be appreciated, one non-limiting criteria that can be utilized in connection with enrollment of patients is FLT3 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAMA response); and, (iii) toxicity to normal cells that express FLT3. Standard tests and follow-up are utilized to monitor each of these safety concerns. FLT3 ADCs are found to be safe upon human administration.

Example 12

Detection of FLT3 Protein in Normal and Cancer Patient Derived Specimens

The detection of FLT3 protein in cancer using anti-FLT3 antibodies was assessed in PBMC samples from peripheral blood of patients with Acute Lymphocytic Leukemia in the Myeloid (AML) cell populations.

A. FACS Binding Materials and Methods

In this experiment, samples were incubated with a cocktail of CD45, CD33, CD34, CD3, CD20, CD38 and either anti-Flt3-Biotin or Isotype-Biotin mAbs. Secondary detection for biotinylated mAbs was Streptavidin-PE. Fluorescence minus one (FMO) control cocktails were prepared with Streptavidin-PE (SAv-PE) detection reagent and were used for gating cell populations. An LSRII flow cytometer (BD Biosciences) was used for acquisition of data.

Lymphocytes were gated on CD45+ population from which four distinct populations were identified, CD33+/3−/20− (Myeloid blasts), CD33+/3−/34+/38− (Stem Cells), CD33−/3+(T cells) and CD33−/20+(B cells). Analysis was done with Flowjo software version 9.5.4 (Tri-Star, Ashland, Oreg.). Fluorescent values are reported as Geometric mean (MFI).

B. Results

Figure 16A:
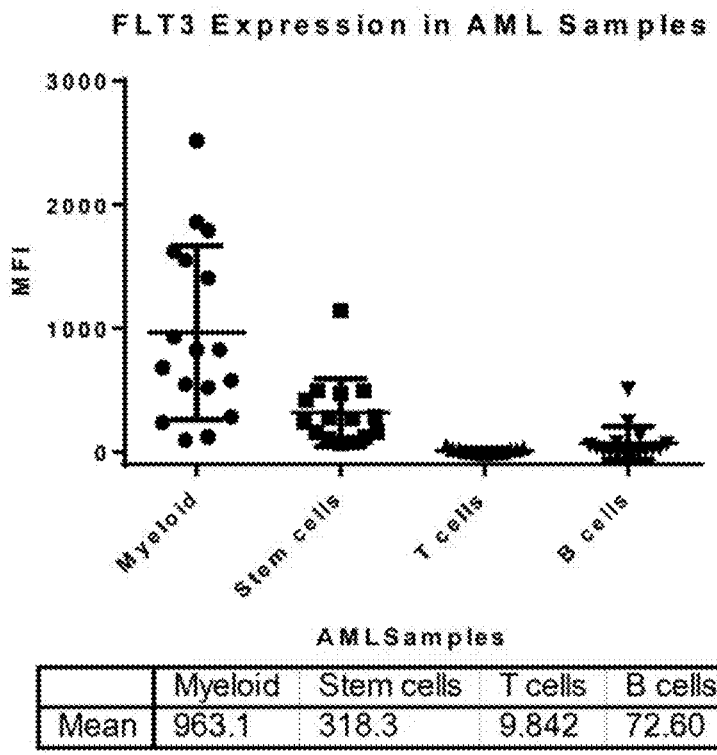
Figure 16B:
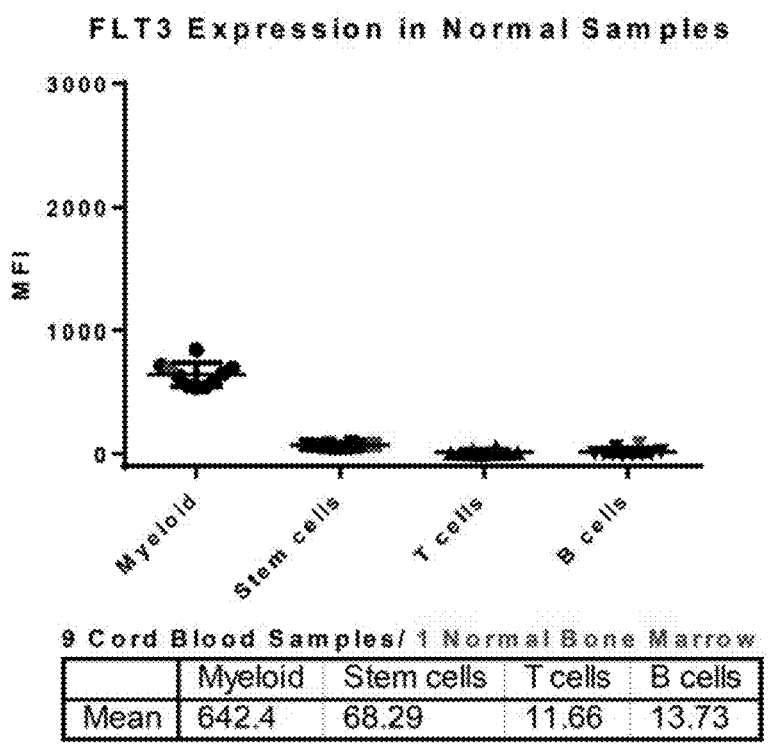

The results set forth in FIGS. 16A-16B for AML patient samples shows that anti-FLT3 MAb binds to the Myeloid, Stem Cells, T and B cell populations of all samples tested.

Furthermore, as shown in FIGS. 16A-16B, the MFIR distribution plots for all samples tested show moderate variability in the Myeloid, stem cell and B cell populations, while T cells had less variability in MFIR. Mean MFIR for Myeloid blasts was around 963.1, while mean MFIR for stem cells was 318.2, while mean MFIR for T cells was 9.842, while MFIR for B-cells was 72.60 in AML. Mean MFIR for normal samples was 642.4 in Myeloid, 68.29 for stem cells, 11.66 for T-cells, and 13.73 for B-cells.

The totality of the results set forth in FIGS. 16A-16B show that the anti-FLT3 MAbs, such as the CHv62.21 MAb and Chv62.21pAF MAb of the invention can detect FLT3 protein overexpressed in AML.

Example 13

In Vitro Cell Cytotoxicity Mediated by CHv62.21pAF and CHv62.21pAF-AGL-0182-30

The ability of FLT3 antibody (CHv62.21pAF) and FLT3 ADC (CHv62.21pAF-AGL-0182-30) to mediate FLT3 dependent cytotoxicity was evaluated using the human leukemia MV-4-11 and MOLM-13 cell lines, which endogenously express FLT3 and the human leukemia cell line, Karpas299, which does not express FLT3.

Briefly, The MV-4-11, MOLM-13, and Karpas299 cells were seeded in 50 µl of complete media, at a density of 1500, 2000, and 3000 cells/well, respectively, onto 96 well plates and placed in a tissue culture incubator at 37 degrees C.; 5% CO2. The next day, cells were Fc blocked at a volume of 25 µl per well to reduce non-specific binding and a 4× stock solution of cHv62.21pAF-AGL-0182-30, isotype control antibody conjugated to AGD-0182 (91.1pAF-AGL-0182-30), cHv62.21pAF, and isotype control antibody (91.1pAF) were prepared in complete media and 25 µl of the serial dilutions of the ADCs and antibodies were added to the appropriate wells. The cells were treated with cHv62.21pAF-AGL-0182-30, 91.1pAF-AGL-0182-30, cHv62.21pAF, and 91.1pAF for 5 days in a tissue culture incubator at 37 degrees C.; 5% CO2. At the end of the incubation period, 20 µl of Presto Blue was added to each well and incubated for 2 hours. The plates were read using a BioTek Synergy $H_4$ plate reader using 540 Excitation and 590 Emission wavelengths.

Figure 17A:
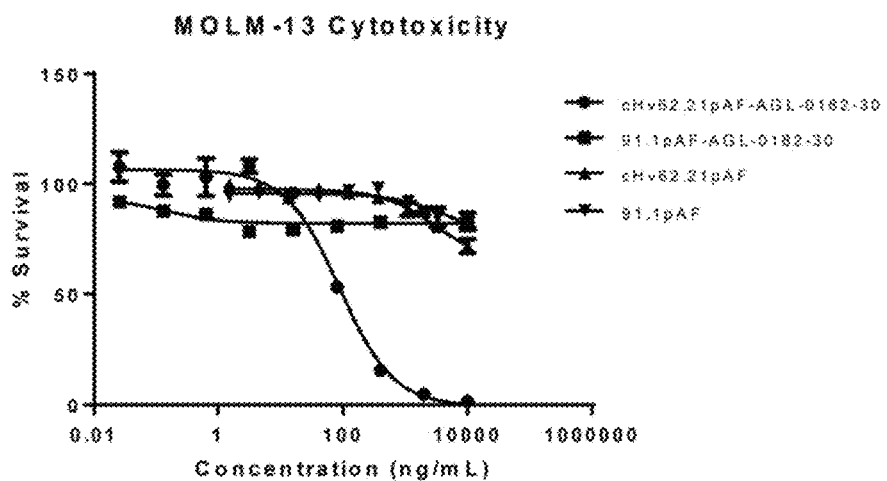
FIGS. 17A-17C. Evaluation of the In-vitro cytotoxicity of cHv62.21pAF-AGL-0182-30 and cHv62.21pAF on MOLM-13, MV-4-11 & Karpas299 cells.
Figure 17B:
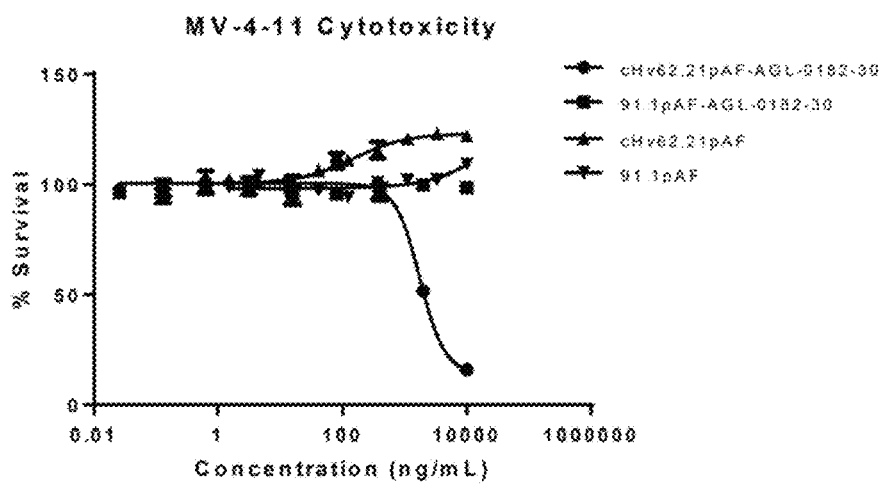
Figure 17C:
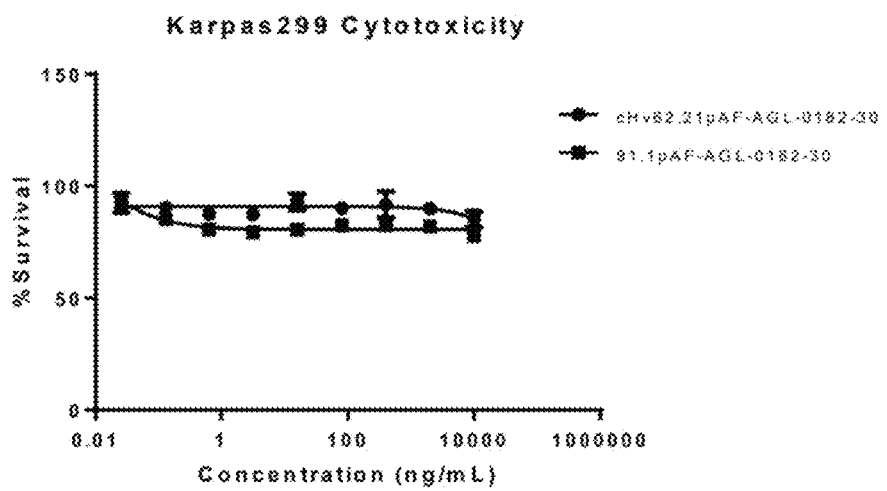

The results in FIGS. 17A-17C show that the anti-FLT3 ADC (CHv62.21pAF-AGL-0182-30) can selectively induce the cytotoxicity of the FLT3 expressing MOLM-13 and MV-4-11 cell lines while it is unable to induce the cytotoxicity of the FLT3 non-expressing Karpas299 cell line. The anti-FLT3 antibody (CHv62.21pAF) does not induce cytotoxicity in MOLM-13 and MV-4-11 cell lines. Thus, these data demonstrate that the FLT3 MAb CHv62.21pAF alone does not induce the cytotoxicity of the cells. Rather, only the FLT3 ADC CHv62.21pAF-AGL-0182-30 can selectively kill FLT3 expressing MOLM-13 and MV-4-11 cells while it has no effect on the non-FLT3 expressing Karpas299 cells.

Example 14

Advantages of CHv62.21pAF Over Prior Art FLT3 MAbs

The CHv62.21pAF MAb of the invention presents several advantages over other MAbs which bind FLT3. Especially when viewed in light of the therapeutic utility of the ADC of the invention. For example, the prior art teaches that after AML patients have been treated with chemotherapy there is an increase in expression of plasma FLT3 ligand ("FL"). See, Takashi, et. al., Blood vol. 117(12) (March 2011). Further, it has been shown that increased FL significantly reduces activity of FLT inhibitors. Id. EB10 conjugated with Monomethyl auristatin F (EB10-MMAF) has been reported as the ADC comprising anti-human FLT3 antibody. (See, Proc Amer Assoc Cancer Res, Volume 46, 2005). The EB10 has been shown to block FL. See, U.S. Pat. No. 8,071,099 (Imclone). Accordingly, an object of the present invention is to engineer MAbs which bind FLT3 antigen, but do not bind FL.

In one experiment, the CHv62.21 MAb of the invention was confirmed to not block FL. Briefly, Recombinant human FLT3-Fc was purchased from R and D Systems. This protein was immobilized onto the surface of activated Luminex microspheres using standard sulfo-NHS/EDC chemistry according to the procedure provided by Luminex. A His-tagged version of the protein, along with several other proteins were conjugated to Luminex microspheres, and served as controls in this procedure.

In addition, FLT3 ligand was also purchased from R and D Systems. The ligand was biotinylated using Thermo Scientific EZ-Link Sulfo-NHS-LC-Biotin, No-Weigh Formula according to the manufacturer's recommendations. After two (2) hours of reacting the protein with Sulfo-NHS-LC-Biotin, unincorporated biotin was removed by dialysis against DPBS.

The ability of FLT3 immobilized onto the surface of the microspheres to bind to its biotinylated ligand was assessed by reacting the microspheres with various concentrations of biotinylated ligand, prepared in buffer containing PBS, 2% BSA, 0.05% Tween 20, and 0.1% sodium azide, for 120 minutes at RT with gentle shaking. At the end of the incubation, the microspheres were aspirated and washed. Biotinylated FLT3 ligand bound to its immobilized receptor was detected with Streptavidin-R-Phycoerythrin (Moss, Inc.). The fluorescence associated with the microspheres was measured with the Luminex instrument. This assessment revealed that a concentration of 5 ng/mL biotinylated FLT3 ligand was sufficient to generate a robust signal, but did not saturate the FLT3 associated with the microspheres.

Finally, to assess the ability of the FLT3 antibodies to potentially block ligand, mixtures were prepared containing biotinylated FLT3 ligand at 5 ng/mL, plus the various antibodies under investigation at 10 µg/mL. These mixtures were applied to the FLT3 immobilized onto the microspheres and incubated for 60 minutes. At the end of the incubation, the microspheres were aspirated and washed. Biotinylated FLT3 ligand bound to its immobilized receptor was detected with Streptavidin-R-Phycoerythrin (Moss, Inc.). The fluorescence associated with the microspheres was measured with the Luminex instrument. Antibodies with the capability to block ligand were observed by reduction in MFI (median fluorescence intensity).

Figure 8:
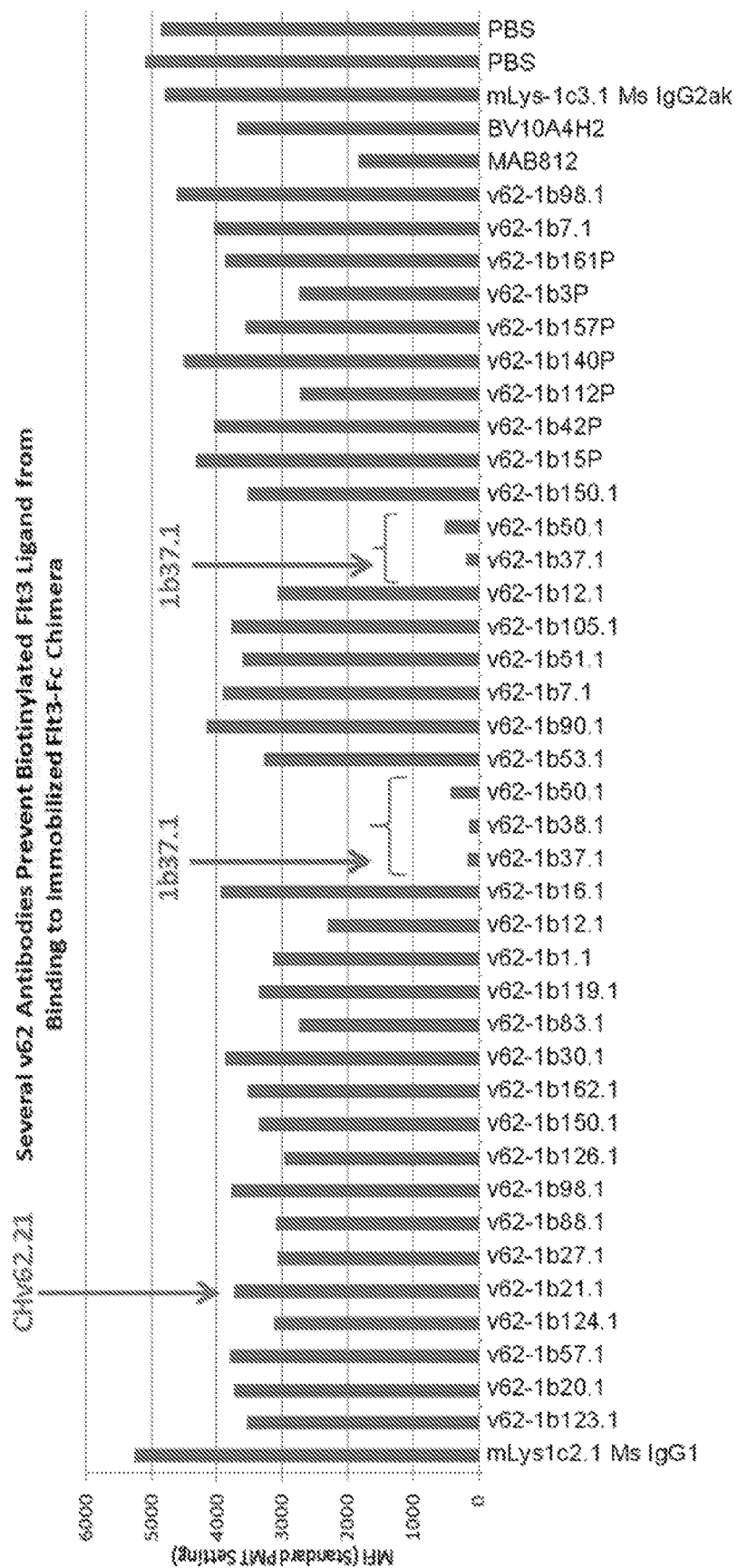
FIG. 8. CHv62.21 Shows Non-Ligand Blocking Activity. FLT3 ligand blocker Mab (1b37.1) which is compared with CHv62.21 in a ligand binding assay confirms CHv62.21 Mab is a non ligand blocker.

The results of FIG. 8 confirm that FLT3 MAb CHv62.21 is a non FL blocker and another FLT3 Mab denoted v62-1b37.1 (Table VII) is a FL blocker, similar to the prior art FLT3 MAb denoted EB10 (See, U.S. Pat. No. 8,071,099).

The ability of FLT3 antibodies (CHv62.21 and v62-1b37.1) to mediate the effect of human FLT3 ligand was evaluated using the human leukemia EOL-1 cell line, which endogenously expresses FLT3. Isotype control antibody (mLys-1c3.1) was also used. The EOL-1 cells were seeded in 50 µl of complete media, at a density of 2000 cells per well onto 96 well plates and placed in a tissue culture incubator at 37° C.; 5% CO2. The next day, cells were treated with 50, 10 or 5 ng/mL of human FLT3 ligand (in 25 µl of complete media) and 10, 1, 0.1 and 0 µg/mL of test antibody (in 25 µl of complete media). Media alone was used as the untreated control. The cells were treated for 5 days in a tissue culture incubator at 37° C.; 5% CO2. At the end of the incubation period, 100 µl of Cell Titer Glo was added to each well and incubated for 30 minutes, shaking, at room temperature. The plates were read using a BioTek Synergy $H_4$ plate reader using Luminescence and graphed using Graphpad Prism software.

Figure 9:
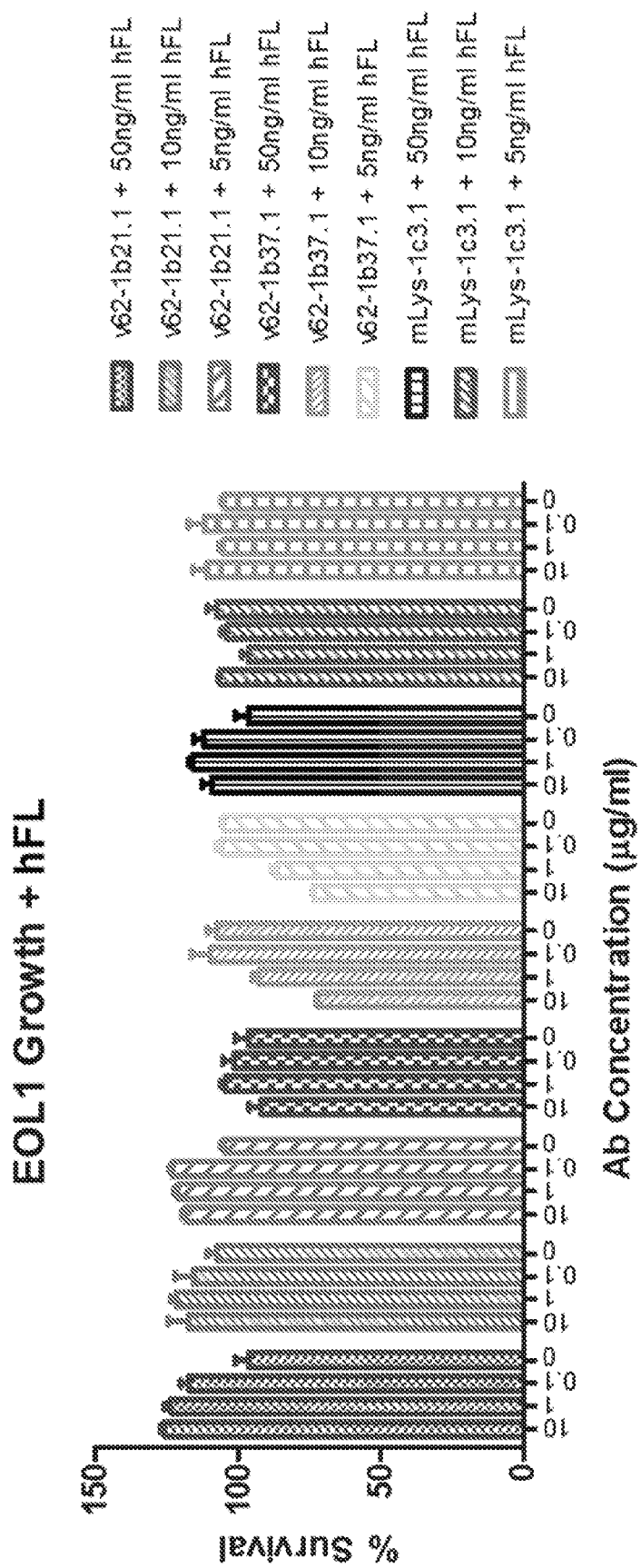
FIG. 9. CHv62.21 Does not Interfere with FL Mediated Cell Proliferation.

The results in FIG. 9, show that the v62-1b37.1 inhibits growth at high concentrations in the presence of FLT3 ligand, but CHv62.21 does not have any effect on growth. Human FLT3 ligand alone has no effect on growth of the EOL-1 cell line.

Based on the teachings that FL concentration in plasma was increased after chemotherapy for cancer treatment (See, Takashi et. al., supra), it was shown that advantages exist when FLT3 MAbs of the invention do not block FL. To confirm this point, it was shown that while the cytotoxic activity of a ligand blocking MAb is reduced in the presence of FL the cytotoxic activity of a non ligand blocking Mab is not reduced in the presence of FL.

The ability of FLT3 ADCs (cHv62.21pAF-AGL-0182-30 and v62-1b21.1-AGL-0129-08) to mediate FLT3 dependent cytotoxicity in the absence and presence of human FLT3 ligand (hFL) was evaluated using the human leukemia RS-4-11 cell line, which endogenously expresses FLT3.

Briefly, The RS-4-11 cells were seeded in 50 µl of complete media at a density of 3000 cells per well onto 96 well plates and placed in a tissue culture incubator at 37° C.; 5% CO2. The next day, the ADCs were prepared in complete media at 10 µg/mL and serially diluted 1:5 for a total of 9 points. 25 µl of the serial dilutions of the ADCs were added to the appropriate wells with and without human FLT3 ligand (100 ng/mL added 25 µl per well). The cells were treated with v62-1b21.1-AGL-0129-08 (Table VIII, See, WO2015/183978, Agensys, Inc.) and v62-1b37.1-AGL-0129-08 with and without human FLT3 ligand for 5 days in a tissue culture incubator at 37° C.; 5% CO2. At the end of the incubation period, 20 µl of Presto Blue was added to each well and incubated for 2 hours. The plates were read using a BioTek Synergy H4 plate reader using 540 Excitation and 590 Emission wavelengths and graphed using Graphpad Prism software.

The results in FIGS. 10(A) and 10(B) show that the anti-FLT3 ADCs (v62-1b21.1-AGL-0129-08 and v62-1b37.1-AGL-0129-08) can induce cytotoxicity of the FLT3 expressing RS-4-11 cell line. The anti-FLT3 ADC, v62-1b21.1-AGL-0129-08, has a similar level of cytotoxicity in the presence and absence of human FLT3 ligand. However, the cytotoxic activity of the anti-FLT3 ADC, v62-1b37.1-AGL-0129-08, is reduced in the presence of human FLT3 ligand compared to ADC treatment without ligand.

In another experiment, The ability of anti-FLT3 antibodies, CHv62.21 and v62-1b37.1, to bind to FLT3 expressed on the surface of human leukemia MOLM-13 cell line was evaluated in the presence of human FLT3 Ligand (hFL). Isotype control antibody, AGS91.1-pAF, was used as a negative control.

Briefly, The MOLM-13 cells were seeded at a density of 50,000 cells per well onto round-bottom 96 well plates. The plates were washed one time with 150 μl per well of PBS. The cells were Fc blocked (20 μg/mL) at a volume of 50 μl per well in FACS buffer (PBS+2% FBS+0.1% sodium azide) to reduce non-specific binding. Cells were incubated at 4° C. for 15 minutes. Human FLT3 Ligand was added to appropriate wells at 100 ng/mL and serially diluted 1:2 across the plate for a total of 11 points. Cells were incubated for 30 minutes at 4° C. prior to adding biotinylated FLT3 antibodies. After incubation, the biotinylated anti-FLT3 antibodies and isotype control antibody were prepared in FACS buffer at 10 μg/mL and 1 μg/mL and 25 μl was added to wells and incubated for 1 hour at 4° C. Cells were washed two times with FACS buffer and Streptavidin-PE (Jackson immune) was added 100 μl per well and incubated for 1 hour at 4° C. Cells were washed two times with FACS buffer and read on the Attune Cytometer (Life technologies) and analyzed in FlowJo (Tree Star) software.

Figures 11A, 11B:
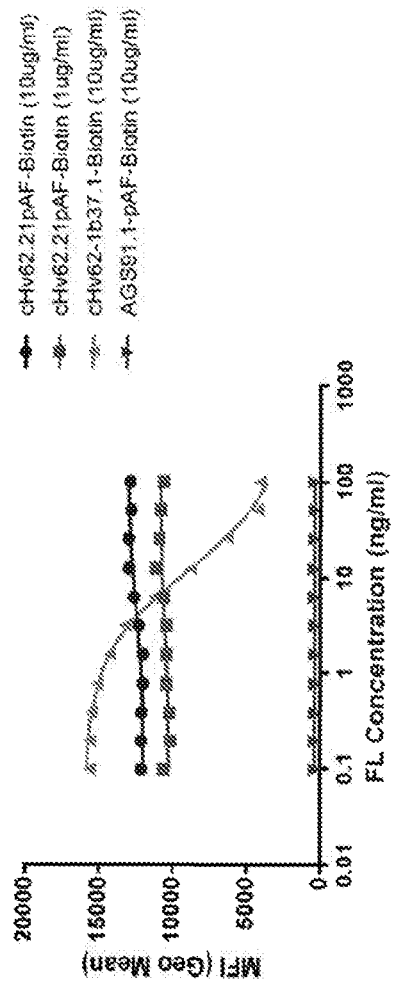
FIG. 11(A). Evaluation of the binding of biotinylated CHv62.21pAF and v62-1b37.1 in the presence of human FLT3 Ligand on MOLM-13 cells.
FIG. 11(B). Evaluation of the In-vitro cytotoxicity of CHv62.21pAF-AGL-0182-30 with and without human FLT3 Ligand on MOLM-13 cells.

The results in FIG. 11(A) show that the human FLT3 Ligand does not interfere with anti-FLT3 antibody, AGS62P, binding to MOLM-13 cells. However, human FLT3 Ligand does interfere with the binding of anti-FLT3 antibody, cHv62-1b37.1, to MOLM-13 cells in a dose-dependent manner.

Finally, The ability of FLT3 ADC, AGS62P1, to mediate FLT3 dependent cytotoxicity in the absence and presence of human FLT3 ligand (hFL) was evaluated using the human leukemia MOLM-13 cell line, which endogenously expresses FLT3. Isotype control ADC, AGS91.1.88-pAF-AGL-0182-30 was used as a negative control.

Briefly, The MOLM-13 cells were seeded in 50 μl of complete media at a density of 2000 cells per well onto 96 well plates and placed in a tissue culture incubator at 37° C.; 5% CO2. The next day, cells were Fc blocked at a volume of 25 μl per well to reduce non-specific binding. The ADCs were prepared in complete media for a final concentration of 10 μg/mL and serially diluted 1:5 for a total of 9 points. 12.5 μl of the serial dilutions of the ADCs were added to the appropriate wells with and without human FLT3 ligand (100 ng/mL added 12.5 μl per well). The cells were treated with AGS62P1 and AGS91.1.88-pAF-AGL-0182-30 with and without human FLT3 ligand for 5 days in a tissue culture incubator at 37° C.; 5% CO2. At the end of the incubation period, 20 μl of Presto Blue was added to each well and incubated for 2 hours. The plates were read using a BioTek Synergy H$_4$ plate reader using 540 Excitation and 590 Emission wavelengths and graphed using Graphpad Prism software.

The result in FIG. 11(B) show that the human FLT3 Ligand does not interfere with anti-FLT3 ADC (CHv62.21pAF-AGL-0182-30) mediated cytotoxicity in MOLM-13 cells.

Thus, while FLT3 MAbs may be used in a therapeutic context, not all FLT3 MAbs are the same. The results in FIGS. 8-11 show that FLT3 MAbs which do not bind FL present prominent advantages over FLT3 MAbs which are shown to bind FL. Further, in light of the therapeutic utility of an ADC of the invention, the results show that an ADC comprising a non-ligand blocker FLT3 Mab, such as CHv62.21pAF-AGL-0182-30 retains anti-tumor effects compared to ADC comprising a ligand blocker FLT3 Mabs in the presence of FL. One of ordinary skill in the art understands that the presence of FL is known to increase after chemotherapeutic treatments. In addition, it is known that elevated presence of FL has been shown to decrease activity of FLT3 inhibitors. Accordingly the results in FIGS. 8-11 suggests that an ADC comprising a non-ligand blocker FLT3 Mab have a better therapeutic index and anti-tumor effects when compared to an ADC comprising a ligand blocker FLT3 Mab in cancer patients.

Example 15

Stability Test of CHv62.21pAF-AGL-0182-30

The stability of FLT3 ADC CHv62.21pAF-AGL-0182-30 and another FLT3 ADC using another cytotoxic compound denoted AGL-0301-20 (See, WO2014/043403, Agensys, Inc.) was evaluated in vitro. In this experiment, human serum (Millipore) was spiked with 0.4 mg/mL of each ADC and phosphate pH 7.3 at a final concentration of 50 mM and incubated in a humidified incubator at 37° C. 100 μL aliquots were collected and frozen at −80C at 5 minutes, 3 hours, 25.25 hours, 51.25 hours, and 171.2 hours. After all samples were collected, ELISA was performed to quantify the antibody and drug components of each ADC.

Figures 12, 12A:
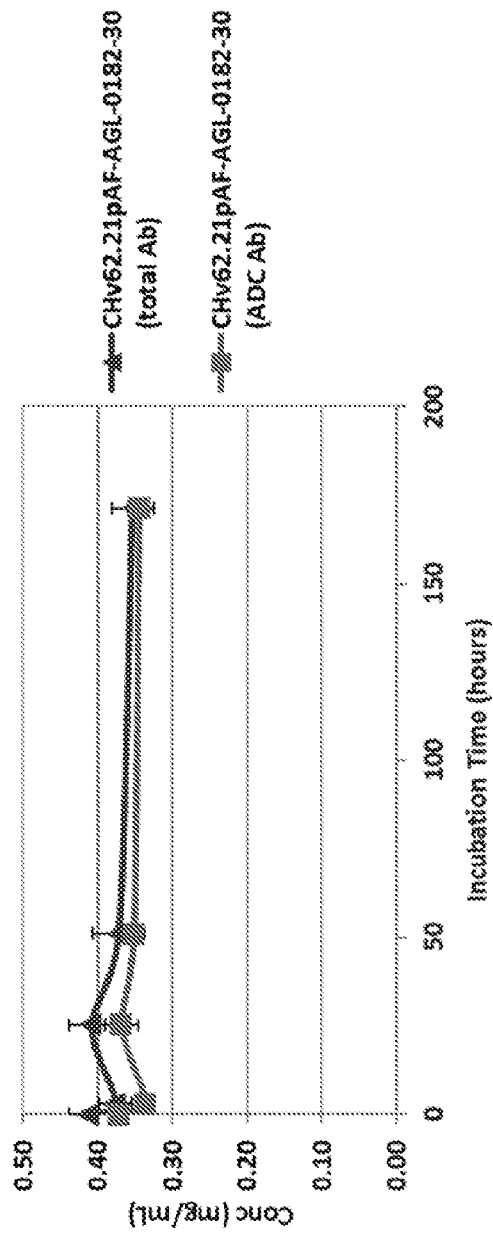
FIG. 12. In vitro Stability of CHv62.21pAF-AGL-0182-30.
FIG. 12(A). Evaluation of Stability of CHv62.21pAF-AGL-0182-30 in Human Serum.

The results show that CHv62.21pAF-AGL-0182-30 drug antibody linkage is stable over the time course of the experiment FIG. 12(A). However, FIG. 12(B) shows that the drug-antibody linkage for v62-1b21-AGL-0301-20 is labile, resulting in significant de-conugation over the time course of the experiment.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues/Cells that express FLT3 when malignant.

Acute Myeloid Leukemia ("AML");
Acute Lymphoblastic Leukemia ("ALL")
B-cell Lymphoblastic Leukemia;
Precursor B-cell Lymphblastic Leukemia.

TABLE II

Amino Acid Abbreviations

| SINGLE LETTER | THREE LETTER | FULL NAME |
| --- | --- | --- |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix
(block substitution matrix). The higher the value,
the more likely a substitution is found in related, natural proteins.

| A | C | D | E | F | G | H | I | K | L | M | N | P | Q | R | S | T | V | W | Y | . |
| --- | --- | --- | --- | --- | --- | --- | --- | --- | --- | --- | --- | --- | --- | --- | --- | --- | --- | --- | --- | --- |
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV

General Method for Synthesis of AGL-0182-30

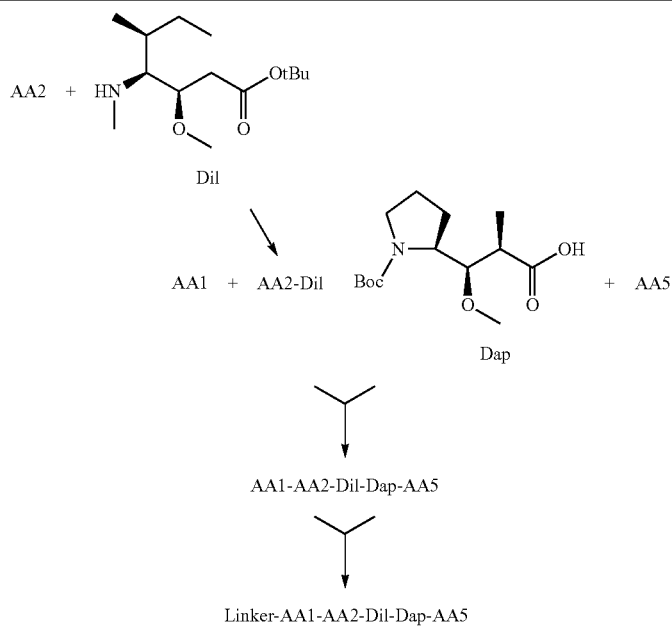

General Merthod for Synthesis of AGL-0182-30
Where AA1 = Amino acid 1
AA2 = Amino acid 2
AA5 = Amino acid 5
Dil = Dolaisoleuine
Dap = Dolaproine
Linker = Aminooxyacetyl

TABLE V

Positions CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

| CDR | Kabat | Chothia | Contact |
|---|---|---|---|
| CDR-L1 | L24-L34<br>RASQGIRNDLG<br>(SEQ ID NO: 14) | L24-L34<br>RASQGIRNDLG<br>(SEQ ID NO: 15) | L30-L36<br>RNDLGWY<br>(SEQ ID NO: 16) |
| CDR-L2 | L50-L56<br>AASSLQS<br>(SEQ ID NO: 17) | L50-L56<br>AASSLQS<br>(SEQ ID NO: 18) | L46-L55<br>RLIYAASSLQ<br>(SEQ ID NO: 19) |
| CDR-L3 | L89-L97<br>LQHNGFPYT<br>(SEQ ID NO: 20) | L89-L97<br>LQHNGFPYT<br>(SEQ ID NO: 21) | L89-L96<br>LQHNGFPYT<br>(SEQ ID NO: 22) |
| CDR-H1* | H31-H35<br>GYSIN<br>(SEQ ID NO: 23) | H26-H32<br>GFTFSGY<br>(SEQ ID NO: 24) | H30-H35<br>SGYSIN<br>(SEQ ID NO: 25) |
| CDR-H1** | H31-H35<br>GYSIN<br>(SEQ ID NO: 26) | H26-H32<br>GFTFSGY<br>(SEQ ID NO: 27) | H30-H35<br>SGYSIN<br>(SEQ ID NO: 28) |
| CDR-H2 | H50-H65<br>SISSSSNYIYYADSVKG<br>(SEQ ID NO: 29) | H52-H56<br>SSSSN<br>(SEQ ID NO: 30) | H47-H58<br>WVSSISSSSNYI<br>(SEQ ID NO: 31) |

TABLE V-continued

Positions CDR-L1, CDR-L2, CDR-L3 and CDR-H1, CDR-H2, CDR-H3 as identified by the Kabat, Chothia, and Contact schemes, respectively. For CDR-H1, residue numbering is given listed using both the Kabat and Chothia numbering schemes.

| CDR | Kabat | Chothia | Contact |
| --- | --- | --- | --- |
| CDR-H3 | H95-H102<br>EGFIAGTTFDAFDI<br>(SEQ ID NO: 32) | H95-H102<br>EGFIAGTTFDAFDI<br>(SEQ ID NO: 33) | H93-H101<br>AREGFIAGTTFDAFD<br>(SEQ ID NO: 34) |

*Kabat Numbering
**Chothia Numbering

TABLE VI

Table of Geometric Mean values and Mean Florescence ratio (MFR) values in FACS assay.

| Cell Line | Cancer Type | Source | Unstained | Secondary Detection | Isotype | cHv62-1b21.1 | MFR |
| --- | --- | --- | --- | --- | --- | --- | --- |
| Karpas-299 | ALCL | DSMZ | 623 | 596 | 569 | 634 | 1 |
| REH | ALL | ATCC | 220 | 236 | 235 | 16200 | 69 |
| EOL-1 | AML | Sigma/HPA | 282 | 292 | 281 | 14000 | 50 |
| MOLM-13 | AML | DSMZ | 303 | 313 | 320 | 14000 | 44 |
| MONOMAC-1 | AML | Creative Bioarray | 315 | 348 | 338 | 11400 | 34 |
| MV-4-11 | AML | ATCC | 344 | 355 | 366 | 2875 | 8 |
| OCI-AML2 | AML | DSMZ | 343 | 337 | 329 | 5646 | 17 |
| PL-21 | AML | DSMZ | 598 | 584 | 570 | 3715 | 7 |
| SKM-1 | AML | DSMZ | 465 | 449 | 445 | 3208 | 7 |
| THP-1 | AML | ATCC | 486 | 475 | 474 | 19700 | 42 |
| RS4; 11 | B-ALL | ATCC | 184 | 213 | 213 | 18400 | 86 |
| SEM | B-ALL | DSMZ | 181 | 207 | 212 | 132000 | 623 |
| NALM-1 | CML | ATCC | 197 | 254 | 262 | 12900 | 49 |

TABLE VII

Antibody Sequence of v62-1b37.1.

The amino acid sequence of v62-1b37.1 heavy chain..
(SEQ ID NO: 12)

```
  1    EVQLVESGGGVVRPGGSLRLSCAASGFTFDDYGMSWVRQAPGKGLEWVSG
 51    INWNGGSTGYADSVKGRFTISRDDAKNSLYLQKNSLRAEDTALYHCARDG
101    YTYGPFDNWGQGTLVTVSSASTKGPSVFPLAPSSKSTSGGTAALGCLVKD
151    YFPEPVTVSWNSGALTSGVHTFPAVLQSSGLYSLSSVVTVPSSSLGTQTY
201    ICNVNHKPSNTKVDKKVEPKSCDKTHTCPPCPAPELLGGPSVFLFPPKPK
251    DTLMISRTPEVTCVVVDVSHEDPEVKFNWYVDGVEVHNAKTKPREEQYNS
301    TYRVVSVLTVLHQDWLNGKEYKCKVSNKALPAPIEKTISKAKGQPREPQV
351    YTLPPSREEMTKNQVSLTCLVKGFYPSDIAVEWESNGQPENNYKTTPPVL
401    DSDGSFFLYSKLTVDKSRWQQGNVFSCSVMHEALHNHYTQKSLSLSPGK
```

The amino acid sequence of v62-1b37.1 light chain..
(SEQ IS NO: 13)

```
  1    DIQMTQSPSSLSASVGDRVTITCRASQGIRNDLGWYQQKPGKAPKRLIYA
 51    ASSLQSGVPSRFSGSGSGTEFTLTISSLQPEDFATYYCLQHNSYPYTFGQ
101    GTKLEIKRTVAAPSVFIFPPSDEQLKSGTASVVCLLNNFYPREAKVQWKV
```

TABLE VII-continued

Antibody Sequence of v62-1b37.1.

151  DNALQSGNSQESVTEQDSKDSTYSLSSTLTLSKADYEKHKVYACEVTHQG

201  LSSPVTKSFNRGEC

TABLE VIII

Chemical composition of AGL-0129-08.

0129-08 means (S)-methyl 2-((2R,3R)-3-((S)-1-((3R,4S,5S)-4-((2S,3S)-3-azido-2-((S)-2-(dimethyl-amino)-3-methylbutanamido)-N-methylbutanamido)-3-methoxy-5-methylheptanoyl)pyrrolidin-2-yl)-3-methoxy-2-methylpropanamido)-3-phenylpropanoate

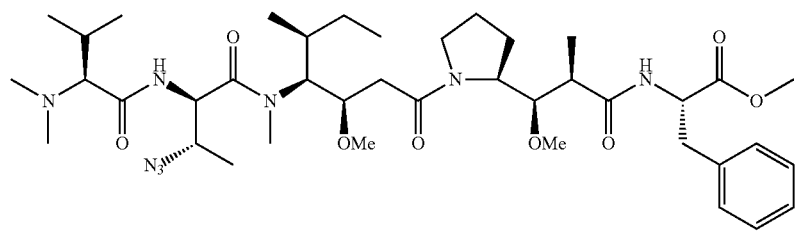 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](NC(=O)[C@H](C(C)C)N(C)C)[C@H](C)N=[N+]=[N-]]

The invention claimed is:

1. An antibody or antigen binding fragment thereof that binds to FLT-3 comprising a CDRH1 having the amino acid sequence of SEQ ID NO:23, a CDRH2 having the amino acid sequence of SEQ ID NO:29, a CDRH3 having the amino acid sequence of SEQ ID NO:32, a CDRL1 having the amino acid sequence of SEQ ID NO: 14, a CDRL2 having the amino acid sequence of SEQ ID NO: 17, and a CDRL3 having the amino acid sequence of SEQ ID NO:20,
   wherein the antigen binding fragment is selected from a group consisting of Fab, Fab', F(ab')2, Fv, and scFv;
   wherein the antibody comprises an Fc region that is an IgG subtype; and
   wherein, optionally, the antibody comprises an Fc region that comprises a substitution of a non-natural amino acid at amino acid position 124 of the heavy chain, and wherein the non-natural amino acid is para-acetylphenylalanine (pAF).

2. The antibody according to claim 1, wherein the antibody comprises:
   (i) a heavy chain variable region consisting of the amino acid sequence ranging from 1st amino acid to the 123rd amino acid of SEQ ID NO: 11 and a light chain variable region consisting of the amino acid sequence ranging from 1st amino acid to the 108th amino acid of SEQ ID NO: 10;
   (ii) a heavy chain consisting of the amino acid sequence ranging from 1st amino acid to the 452nd amino acid of SEQ ID NO: 11 and a light chain consisting of the amino acid sequence ranging from the 1st amino acid to the 214th amino acid of SEQ ID NO: 10;
   (iii) heavy chain consisting of the amino acid sequence ranging from 1st amino acid to the 453rd amino acid of SEQ ID NO: 11 and a light chain consisting of the amino acid sequence ranging from 1st amino acid to the 214th amino acid of SEQ ID NO: 10;
   (iv) a heavy chain, wherein the 2nd amino acid to the 452rd amino acid of the heavy chain consists of the amino acid sequence ranging from the 2nd amino acid to the 452rd amino acid of SEQ ID NO: 11, and wherein the 1st amino acid of the heavy chain is pyroglutamate, and a light chain consisting of the amino acid sequence ranging from the 1st amino acid to the 214th amino acid of SEQ ID NO: 10;
   (v) a heavy chain variable region consisting of the amino acid sequence of the heavy chain variable region of an antibody produced by a Chinese Hamster Ovary (CHO) cell deposited under ATCC Accession No. PTA-121831 and a light chain variable region consisting of the amino acid sequence of the light chain of an antibody produced by a Chinese Hamster Ovary (CHO) deposited under ATCC. Accession No. PTA-121831; or
   (vi) a heavy chain consisting of the amino acid sequence of the heavy chain of an antibody produced by a Chinese Hamster Ovary (CHO) cell deposited under ATCC. Accession No. PTA-121836, and a light chain consisting of the amino acid sequence of the light chain of an antibody produced by a Chinese Hamster Ovary (CHO) deposited under ATCC. Accession No. PTA-121836.

3. One or more isolated nucleic acids encoding the antibody or the antigen-binding fragment according to claim 1.

4. One or more expression vectors comprising the one or more isolated nucleic acids according to claim 3.

5. A recombinant host cell comprising the one or more expression vectors according to claim 4.

6. An antibody or an antigen-binding fragment produced by culturing the recombinant host cell according to claim 5.

7. An antibody drug conjugate comprising the antibody or the antigen-binding fragment according to claim 1 conjugated to a therapeutic agent via a linker,
  (i) wherein, optionally, the antibody or the antigen-binding fragment binds FLT3 but doe not substantially inhibit the binding of FLT3 to FLT3 ligand (FL);
  (ii) wherein, optionally, the linker is a non-cleavable linker, which is optionally 2-(aminooxy) acetic acid;
  (iii) wherein, optionally, the therapeutic agent is (2S, 3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide; and
  (iv) wherein, optionally, the antibody drug conjugate has the following formula:

Antibody-(Linker-therapeutic agent)p, wherein the linker is 2-(aminooxy)acetic acid, wherein the therapeutic agent is (2S,3 S)—N-((3R,4S,5 S) -1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide and, and wherein p is selected from the group consisting of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.

8. A pharmaceutical composition comprising a therapeutically effective amount of the antibody drug conjugate according to claim 7,
  (i) wherein, optionally, the pharmaceutical composition is for use in therapy including treatment of cancer, wherein, optionally,
    (a) the cancer comprises one or more cells that express FLT3 at an increased level as compared to a non-cancerous cell; or
    (b) the cancer is selected from the group consisting of Acute Myeloid leukemia (AML), Acute Lymphoblastic leukemia (ALL), B-cell Lymphoblastic leukemia, and Precursor B-cell Lymphoblastic leukemia, and
  (ii) wherein, optionally, the pharmaceutical composition further comprises one or more anti-neoplastic agents.

9. A method of treating cancer in a subject, comprising administering to said subject a therapeutically effective amount of the antibody drug conjugate according to claim 7, wherein, optionally, the subject is a human subject; and wherein, optionally, the cancer is selected from the group consisting of Acute Myeloid leukemia (AML), Acute Lymphoblastic leukemia (ALL), B-cell Lymphoblastic leukemia, and Precursor B-cell Lymphoblastic leukemia.

10. A method of treating cancer in a subject, comprising administering to said subject a therapeutically effective amount of the pharmaceutical composition according to claim 8, wherein, optionally, the subject is a human subject; and wherein, optionally, the cancer is selected from the group consisting of Acute Myeloid leukemia (AML), Acute Lymphoblastic leukemia (ALL), B-cell Lymphoblastic leukemia, and Precursor B-cell Lymphoblastic leukemia.

11. One or more isolated nucleic acids encoding the antibody or the antigen-binding fragment according to claim 2.

12. An antibody drug conjugate comprising the antibody or the antigen-binding fragment according to claim 2 conjugated to a therapeutic agent via a linker,
  (i) wherein, optionally, the antibody or the antigen-binding fragment binds FLT3 but does not substantially inhibit the binding of FLT3 to FLT3 ligand (FL);
  (ii) wherein, optionally, the linker is a non-cleavable linker, which is optionally 2-(aminooxy) acetic acid;
  (iii) wherein, optionally, the therapeutic agent is (2S, 3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide; and
  (iv) wherein, optionally, the antibody drug conjugate has the following formula:

Antibody-(Linker-therapeutic agent)p, wherein the linker is 2-(aminooxy)acetic acid, wherein the therapeutic agent is (2S,3 S)-N-((3R,4S,5 S) -1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamideand, and wherein p is selected from the group consisting of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.

13. An antibody drug conjugate comprising the antibody or the antigen-binding fragment according to claim 6 conjugated to a therapeutic agent via a linker,
  (i) wherein, optionally, the antibody or the antigen-binding fragment binds FLT3 but does not substantially inhibit the binding of FLT3 to FLT3 ligand (FL);
  (ii) wherein, optionally, the linker is a non-cleavable linker, which is optionally 2-(aminooxy) acetic acid;
  (iii) wherein, optionally, the therapeutic agent is (2S,3 S)N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide; and
  (iv) wherein, optionally, the antibody drug conjugate has the following formula:

Antibody-(Linker-therapeutic agent)p, wherein the linker is 2-(aminooxy)acetic acid, wherein the therapeutic agent is (2S,3S)-N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide and, and wherein p is selected from the group consisting of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.

* * * * *